(12) United States Patent
Hedgeland et al.

(10) Patent No.: US 12,178,489 B2
(45) Date of Patent: *Dec. 31, 2024

(54) SYSTEMS AND METHODS FOR INTRAMEDULLARY NAIL IMPLANTATION

(71) Applicant: GLOBUS MEDICAL, INC., Audubon, PA (US)

(72) Inventors: Mark Hedgeland, Eagleville, PA (US); Mark Rossney, Downingtown, PA (US); David R. Jansen, Glenmoore, PA (US)

(73) Assignee: Globus Medical, Inc., Audubon, PA (US)

( * ) Notice: Subject to any disclaimer, the term of this patent is extended or adjusted under 35 U.S.C. 154(b) by 678 days.

This patent is subject to a terminal disclaimer.

(21) Appl. No.: 17/336,844

(22) Filed: Jun. 2, 2021

(65) Prior Publication Data

US 2021/0353349 A1 Nov. 18, 2021

Related U.S. Application Data

(63) Continuation of application No. 16/431,849, filed on Jun. 5, 2019, now Pat. No. 11,045,242, which is a continuation-in-part of application No. 16/153,873, filed on Oct. 8, 2018, now Pat. No. 10,751,096, which is a continuation-in-part of application No. 15/441,457, filed on Feb. 24, 2017, now Pat. No. 10,307,197, which is a continuation-in-part of application No. 15/423,773, filed on Feb. 3, 2017, now Pat. No. 10,251,691, which is a continuation-in-part of application No. 15/272,850, filed on Sep. 22, 2016, now Pat. No. 10,299,847.

(51) Int. Cl.
*A61B 17/88* (2006.01)
*A61B 17/92* (2006.01)
*A61B 17/90* (2006.01)

(52) U.S. Cl.
CPC ........ *A61B 17/8872* (2013.01); *A61B 17/921* (2013.01); *A61B 17/90* (2021.08)

(58) Field of Classification Search
CPC ............ A61B 17/8872; A61B 17/8886; A61B 17/8888; A61B 17/8891; A61B 17/921; A61B 2017/90
USPC .............................. 606/64, 98, 104, 323, 328
See application file for complete search history.

(56) References Cited

U.S. PATENT DOCUMENTS

| 4,667,664 | A | | 5/1987 | Taylor et al. |
| 4,913,137 | A | * | 4/1990 | Azer ................. A61B 17/7233 606/65 |
| 4,952,213 | A | | 8/1990 | Bowman et al. |

(Continued)

FOREIGN PATENT DOCUMENTS

| CN | 201524132 U | 7/2010 |
| DE | 3722852 A1 | 1/1989 |

(Continued)

*Primary Examiner* — Eduardo C Robert
*Assistant Examiner* — David C Comstock

(57) ABSTRACT

Intramedullary nails, aiming guide assemblies, and methods. The aiming guide assembly can include an aiming guide having a collet and a connection bolt configured to engage a connection bolt driver. The connection bolt may be self-retaining and engage with the connection bolt driver in a manner to prevent unintentional disengagement.

20 Claims, 52 Drawing Sheets

(56) References Cited

U.S. PATENT DOCUMENTS

| | | | |
|---|---|---|---|
| 5,034,013 A | 7/1991 | Kyle et al. | |
| 5,167,663 A | 12/1992 | Brumfield | |
| 5,167,666 A | 12/1992 | Mattbeck et al. | |
| 5,207,682 A * | 5/1993 | Cripe | A61B 17/1753 606/98 |
| 5,312,406 A | 5/1994 | Brumfield | |
| 5,354,300 A | 10/1994 | Goble et al. | |
| 5,433,720 A | 7/1995 | Faccioli et al. | |
| 5,549,610 A | 8/1996 | Russell et al. | |
| 5,613,971 A | 3/1997 | Lower et al. | |
| 5,728,128 A | 3/1998 | Crickenberger et al. | |
| 6,120,504 A | 9/2000 | Brumback et al. | |
| 7,476,225 B2 | 1/2009 | Cole | |
| 7,686,808 B2 | 3/2010 | Orbay et al. | |
| 7,780,667 B2 | 8/2010 | Watanabe et al. | |
| 7,799,030 B2 | 9/2010 | Watanabe et al. | |
| 7,914,532 B2 | 3/2011 | Shaver et al. | |
| 7,927,336 B2 | 4/2011 | Rasmussen | |
| 8,083,742 B2 | 12/2011 | Martin | |
| 8,241,286 B2 | 8/2012 | Metzinger et al. | |
| 8,328,805 B2 | 12/2012 | Cole | |
| 8,360,970 B2 | 1/2013 | Mangiardi | |
| 8,449,544 B2 | 5/2013 | Grusin | |
| 8,518,040 B2 | 8/2013 | Schlienger et al. | |
| 8,591,513 B2 | 11/2013 | Overes et al. | |
| 8,685,034 B2 * | 4/2014 | Giersch | A61B 17/1725 606/86 R |
| 8,715,283 B2 | 5/2014 | Brumfield et al. | |
| 8,790,343 B2 | 7/2014 | McClellan et al. | |
| 8,834,469 B2 | 9/2014 | Watanabe et al. | |
| 8,932,301 B2 | 1/2015 | Metzinger et al. | |
| 8,961,518 B2 | 2/2015 | Taylor et al. | |
| 9,101,432 B2 | 8/2015 | Limouze et al. | |
| 9,138,278 B2 | 9/2015 | Van Osten, III | |
| 9,155,582 B2 | 10/2015 | Felder et al. | |
| 10,022,135 B2 | 7/2018 | O'Reilly et al. | |
| 10,507,048 B2 | 12/2019 | Overes et al. | |
| 10,905,477 B2 | 2/2021 | Lueth et al. | |
| 11,045,242 B2 * | 6/2021 | Hedgeland | A61B 17/1721 |
| 2002/0029041 A1 | 3/2002 | Hover et al. | |
| 2006/0111716 A1 | 5/2006 | Schlienger et al. | |
| 2008/0021474 A1 * | 1/2008 | Bonutti | A61B 17/0401 606/28 |
| 2008/0077142 A1 * | 3/2008 | James | A61B 17/72 606/281 |
| 2009/0318926 A1 | 12/2009 | Christie | |
| 2011/0054474 A1 | 3/2011 | Metzinger et al. | |
| 2011/0054550 A1 | 3/2011 | Metzinger et al. | |
| 2011/0077693 A1 | 3/2011 | Yu | |
| 2013/0190570 A1 | 7/2013 | Hirsch et al. | |
| 2013/0282016 A1 | 10/2013 | Volpi et al. | |
| 2013/0317502 A1 | 11/2013 | Overes | |
| 2013/0325076 A1 | 12/2013 | Palmer et al. | |
| 2014/0243838 A1 | 8/2014 | Feibel et al. | |
| 2014/0276828 A1 | 9/2014 | Howling et al. | |
| 2014/0309648 A1 | 10/2014 | Matityahu | |
| 2015/0038967 A1 | 2/2015 | Khong et al. | |
| 2015/0265323 A1 | 9/2015 | Sems et al. | |
| 2015/0305791 A1 | 10/2015 | Purohit | |
| 2016/0089189 A1 | 3/2016 | Buscaglia et al. | |
| 2017/0202566 A1 * | 7/2017 | Luo | A61B 17/1725 |

FOREIGN PATENT DOCUMENTS

| | | |
|---|---|---|
| DE | 4240277 A1 | 6/1993 |
| DE | 4445692 A1 | 5/1996 |
| DE | 202006005629 U1 | 6/2006 |
| EP | 2606836 A1 | 6/2013 |
| EP | 3636175 A3 | 7/2020 |
| EP | 3747375 A1 | 12/2020 |
| JP | 02224653 A | 9/1990 |
| JP | 1996-505550 A | 6/1996 |
| JP | H08505550 A | 6/1996 |
| JP | 2007125386 A | 5/2007 |
| JP | 2007275571 A | 10/2007 |
| JP | 2008531088 A | 8/2008 |
| JP | 2011-500215 A | 1/2011 |
| JP | 2011206125 A | 10/2011 |
| JP | 2013502992 A | 1/2013 |
| JP | 2015504729 A | 2/2015 |
| JP | 2017-515554 A | 6/2017 |
| JP | 2018-149297 A | 9/2018 |
| JP | 2018149273 A | 9/2018 |
| JP | 2020-127742 A | 8/2020 |
| JP | 2021-000440 A | 1/2021 |
| WO | 9415556 A1 | 7/1994 |
| WO | 2006091625 A2 | 8/2006 |
| WO | 2012103335 A1 | 8/2012 |
| WO | 2012103354 A1 | 8/2012 |
| WO | 2013092402 A1 | 6/2013 |
| WO | 2014168184 A1 | 10/2014 |
| WO | 2016039775 A1 | 3/2016 |

* cited by examiner

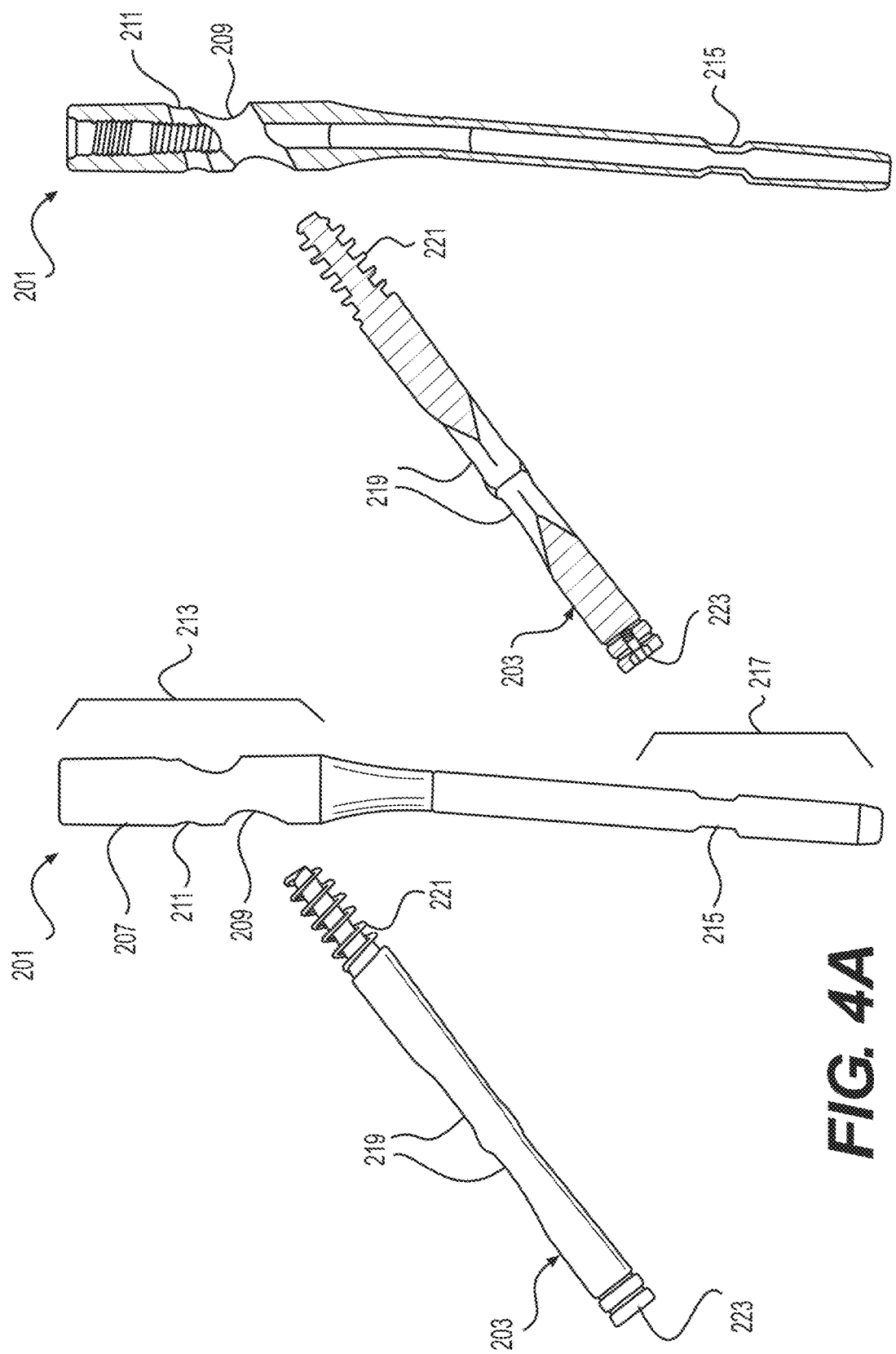

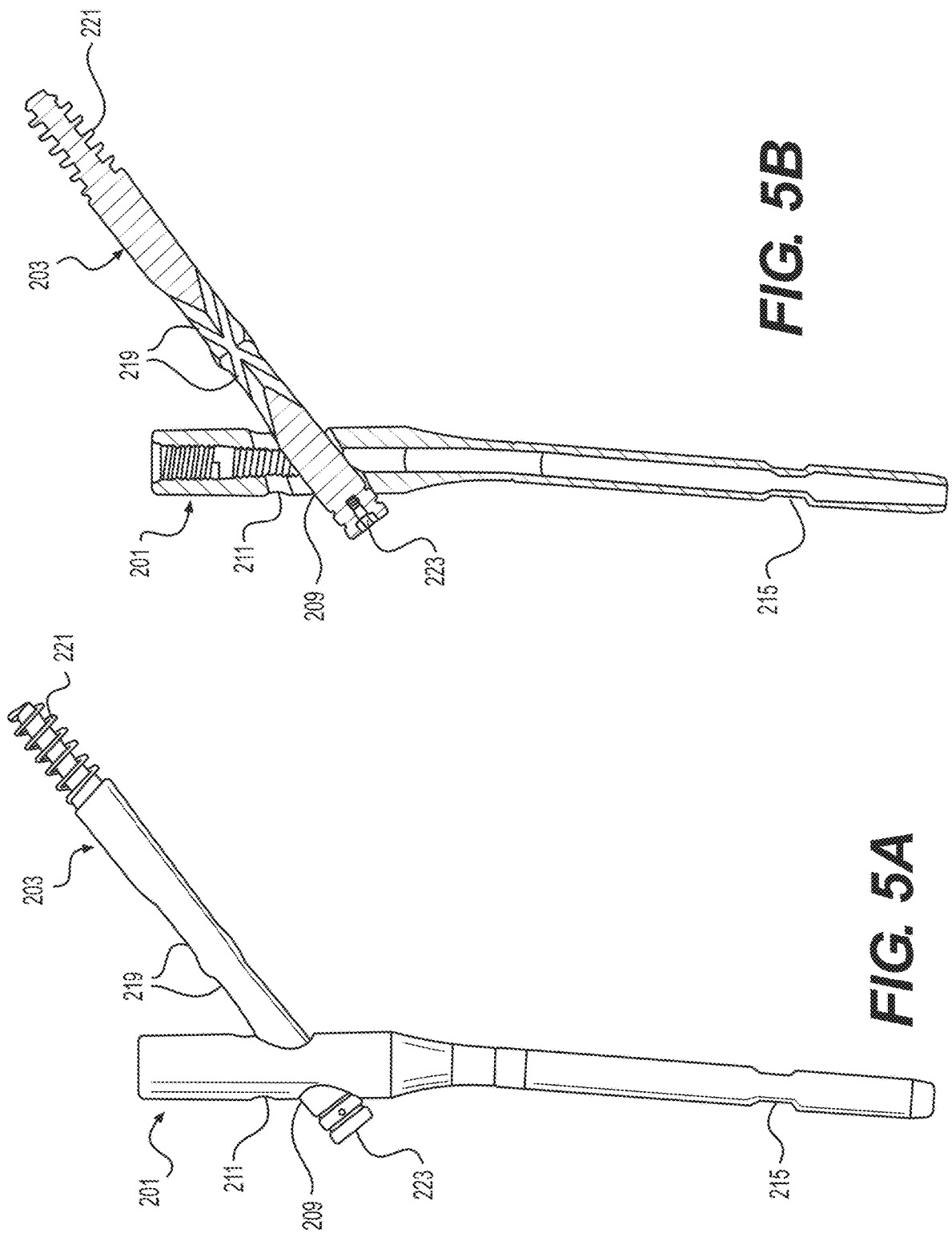

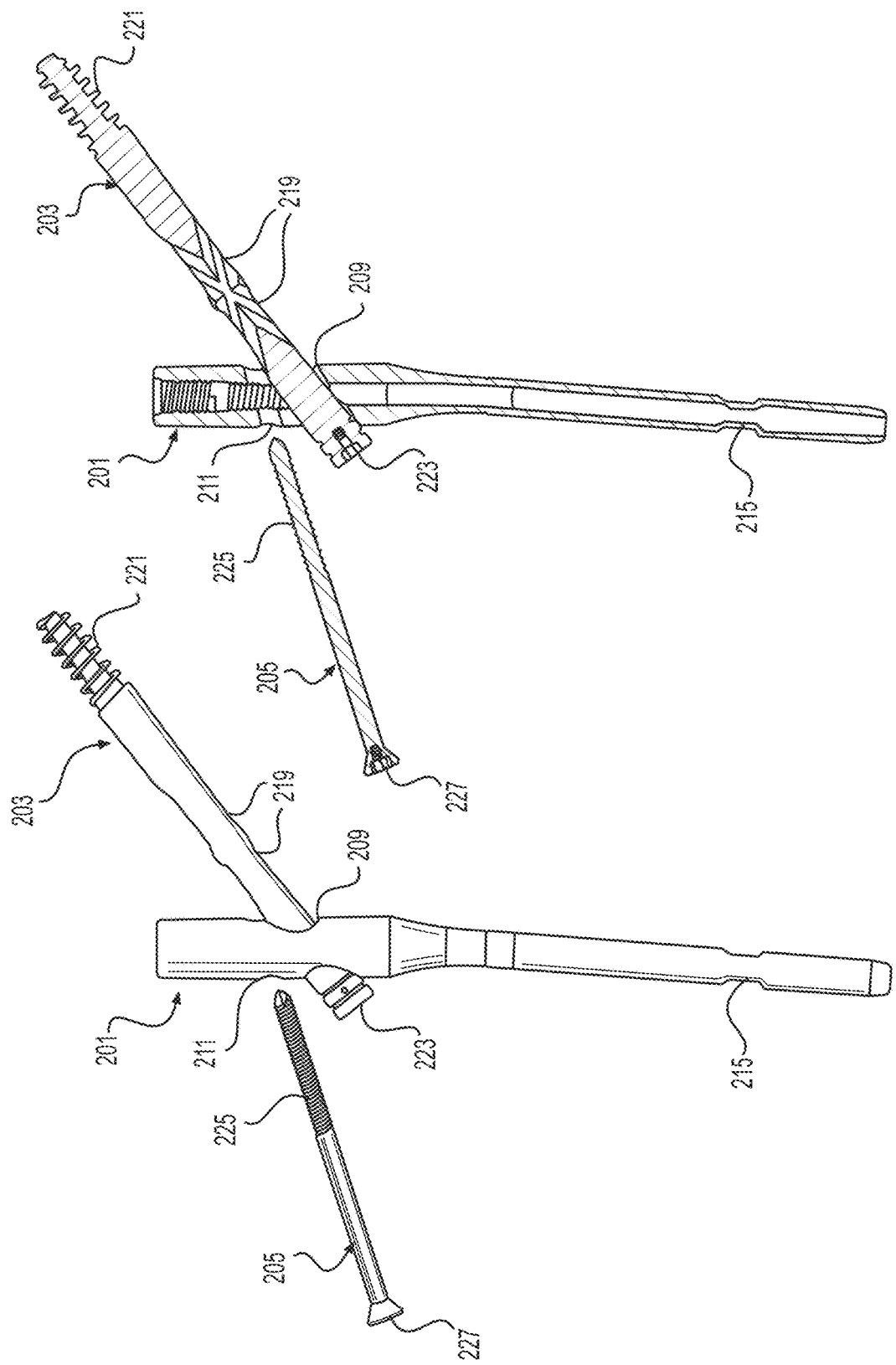

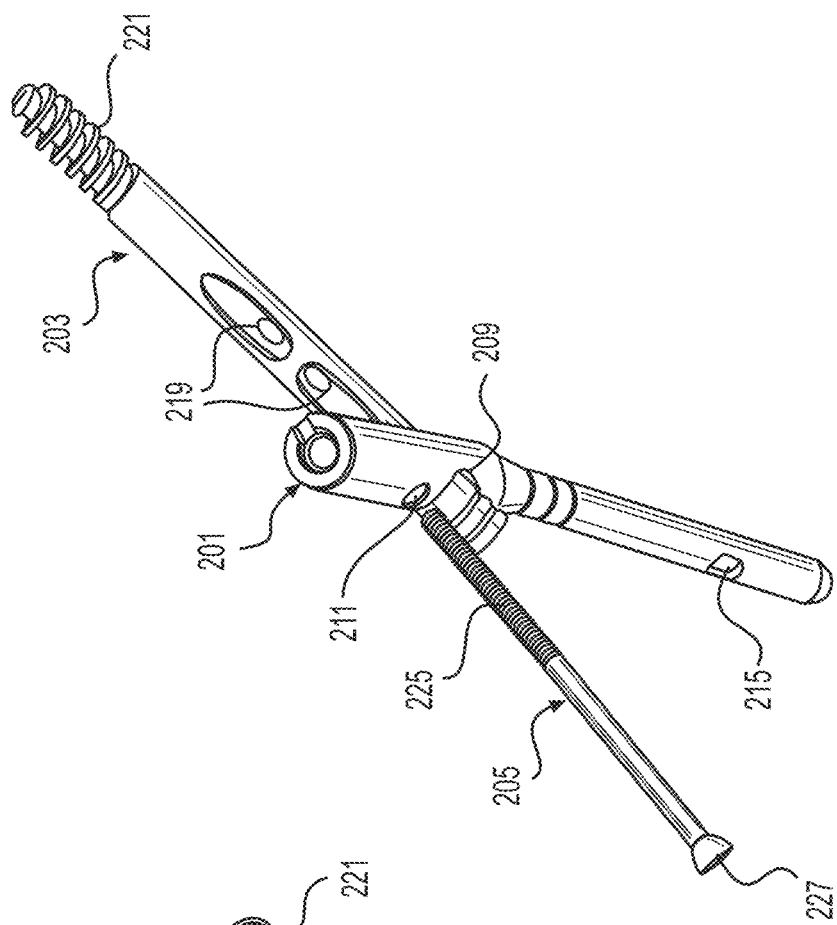
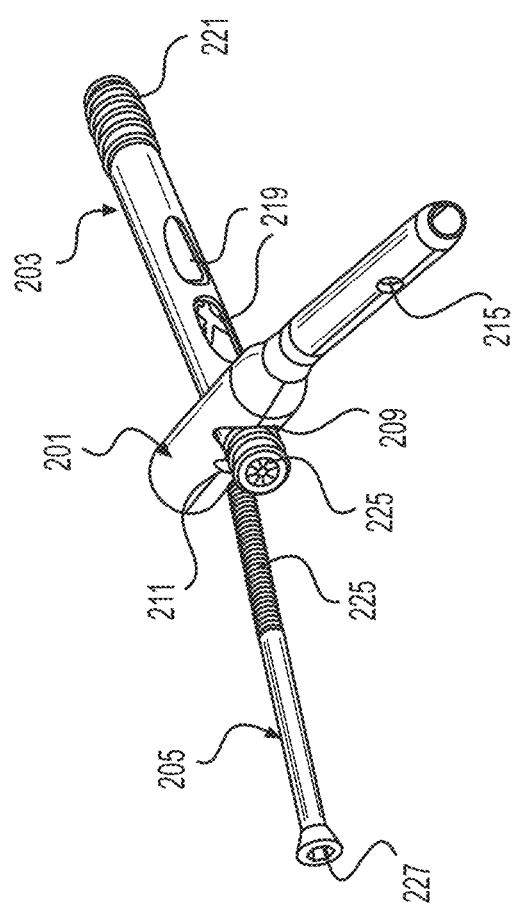
FIG. 6D
FIG. 6C

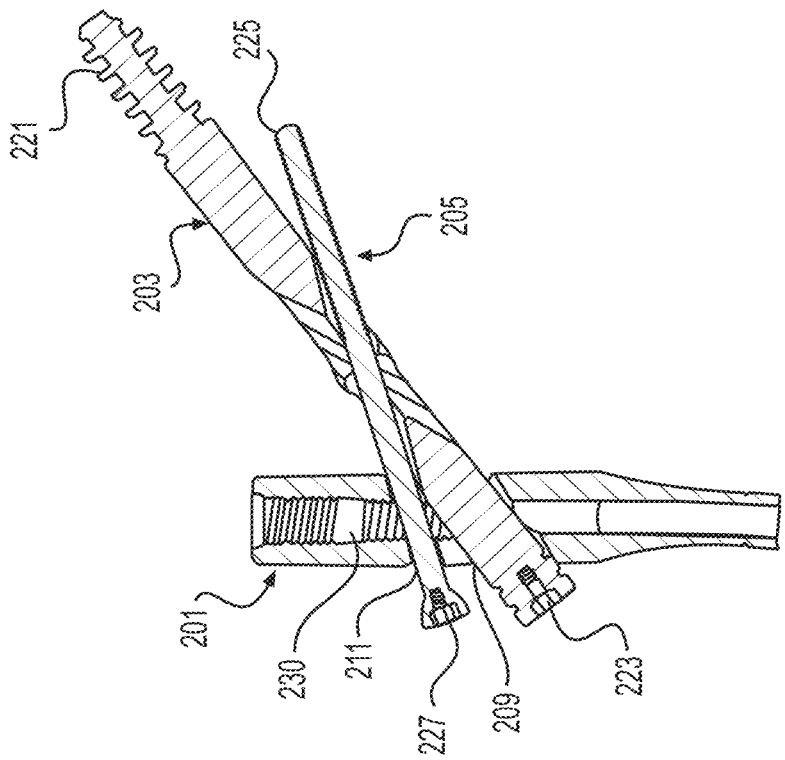
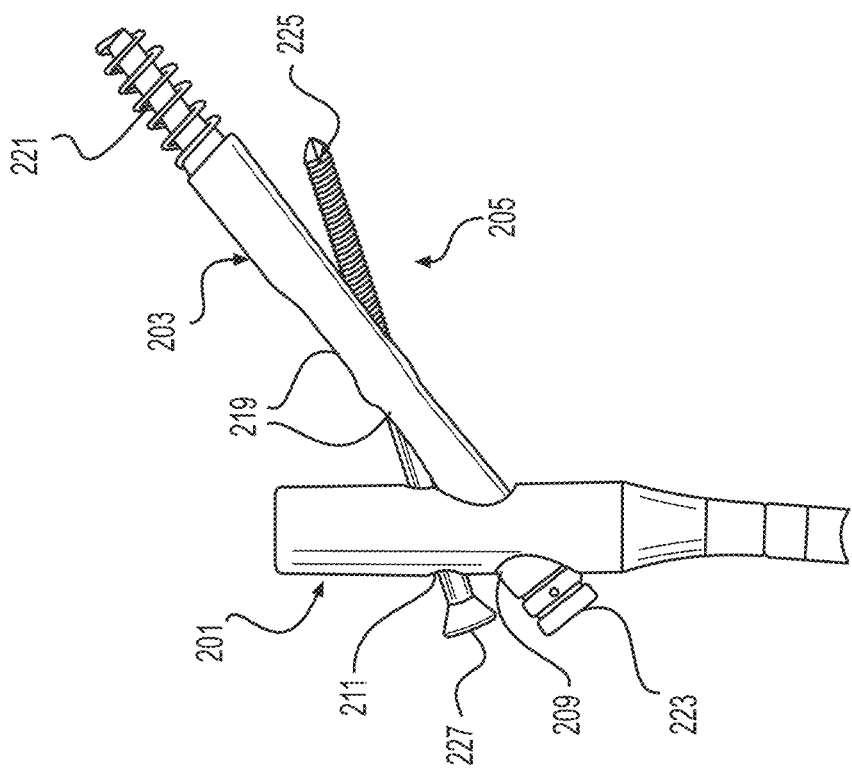
FIG. 7B
FIG. 7A

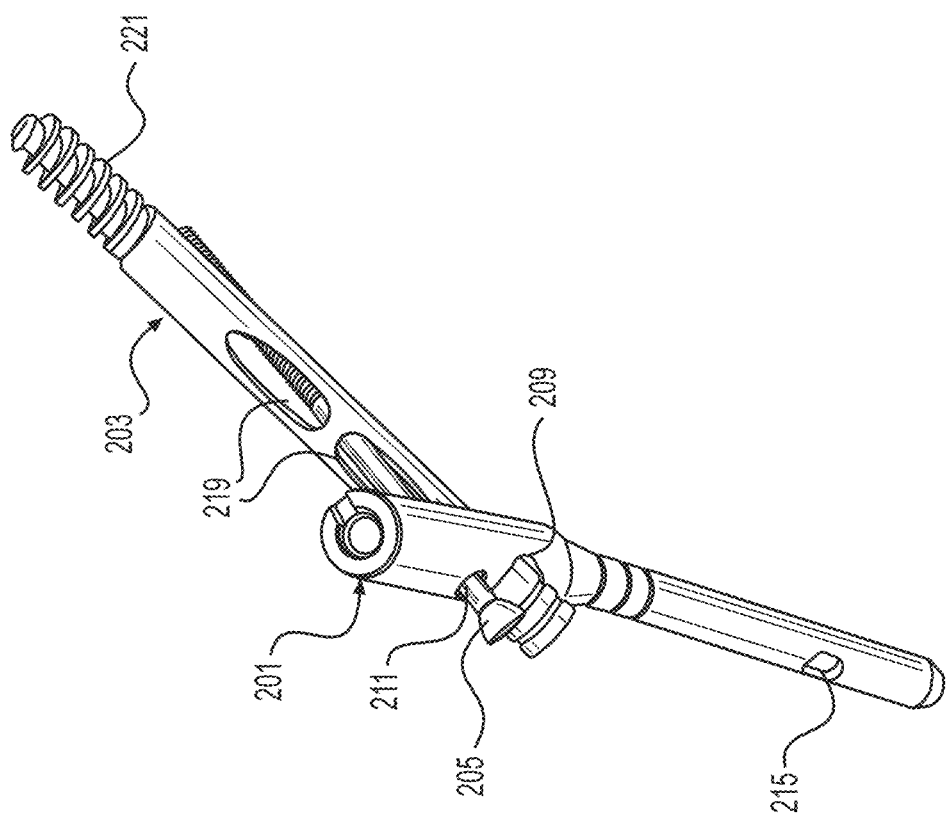
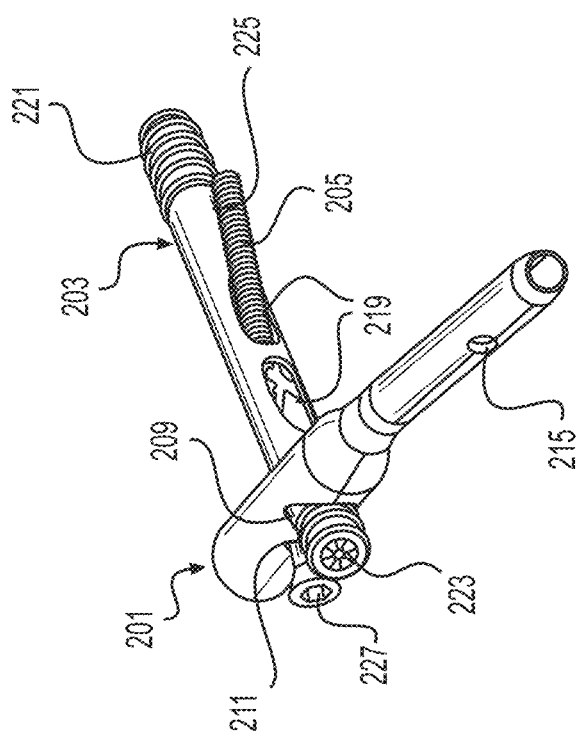
FIG. 7D
FIG. 7C

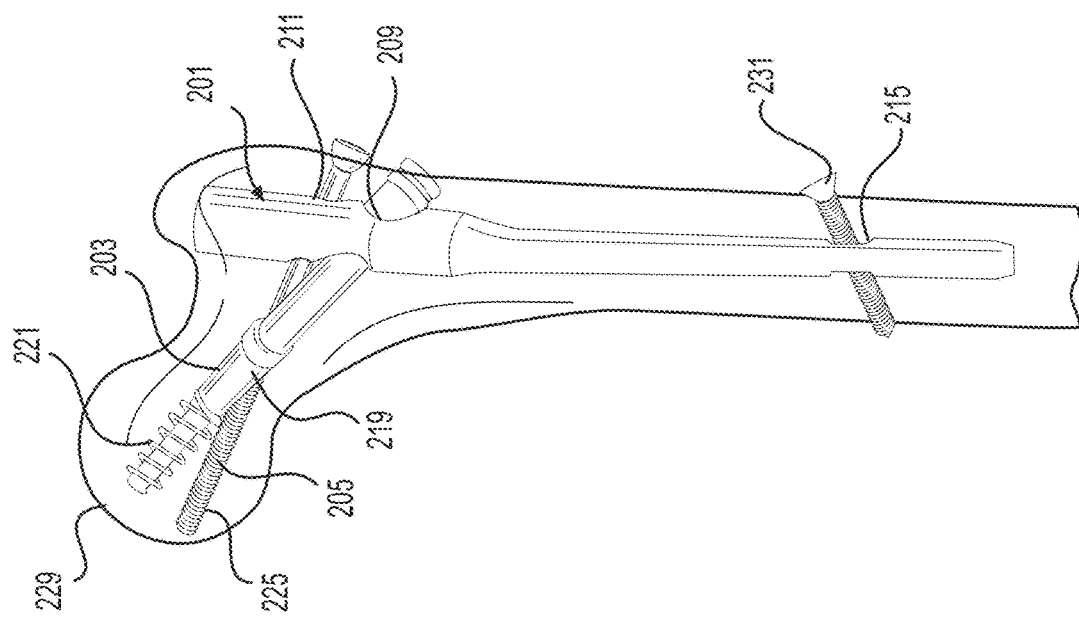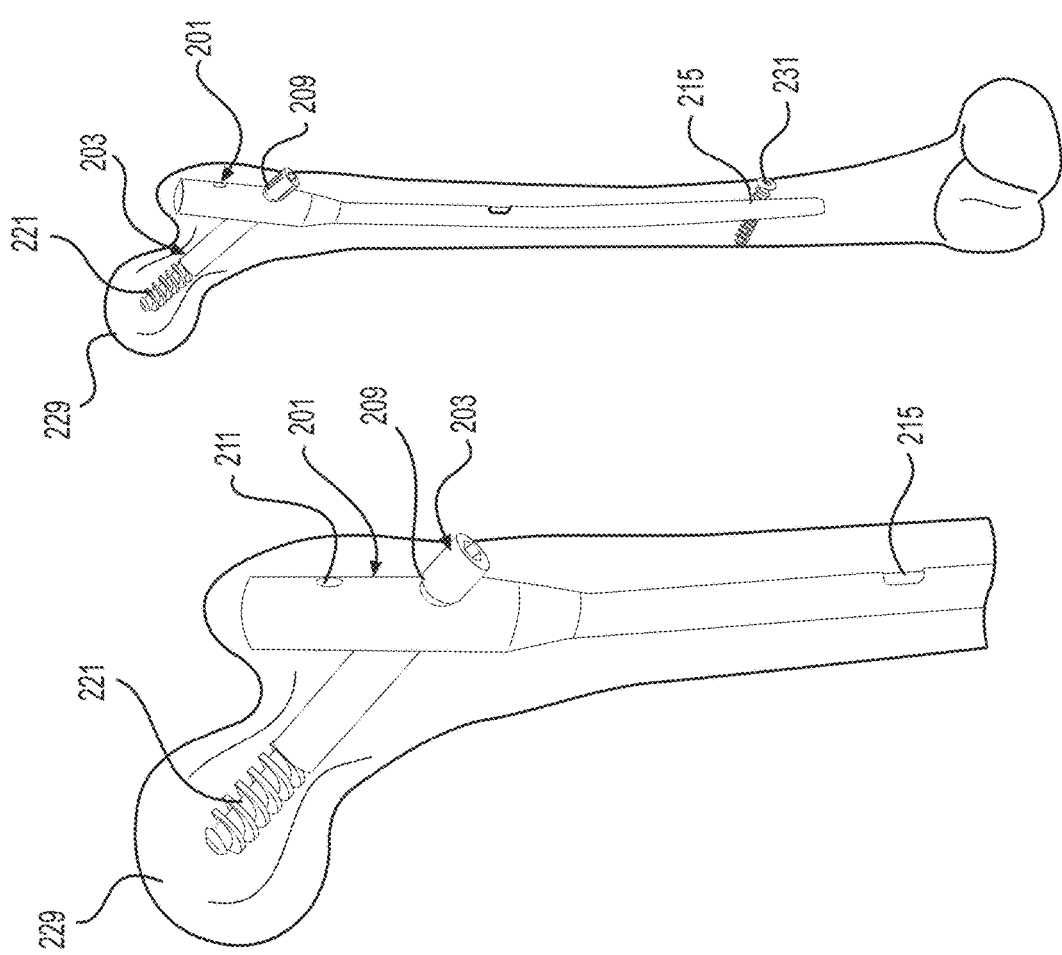

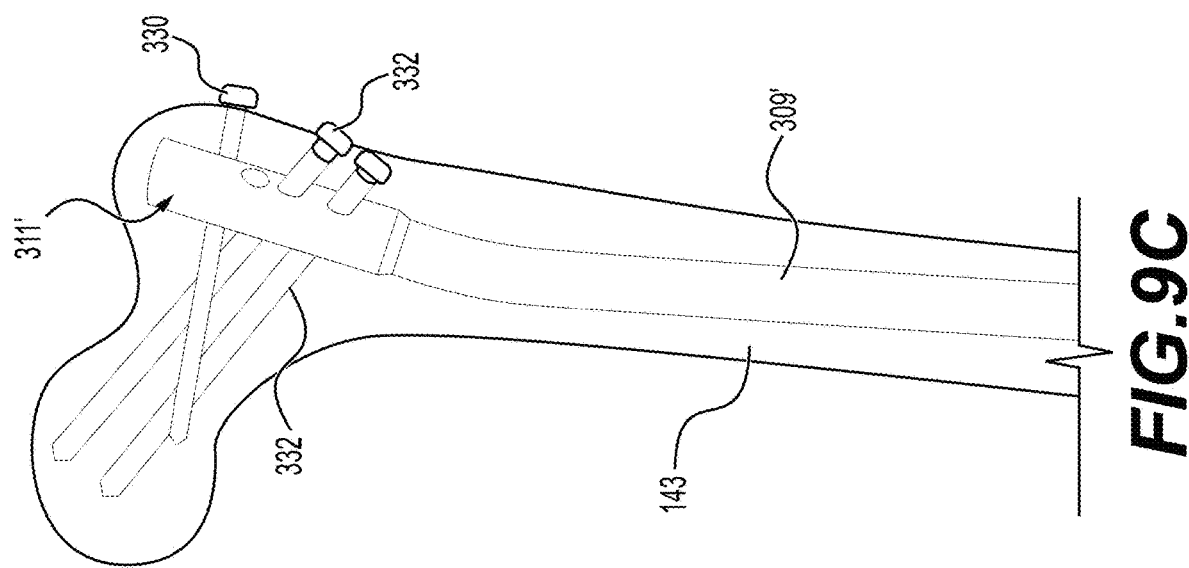

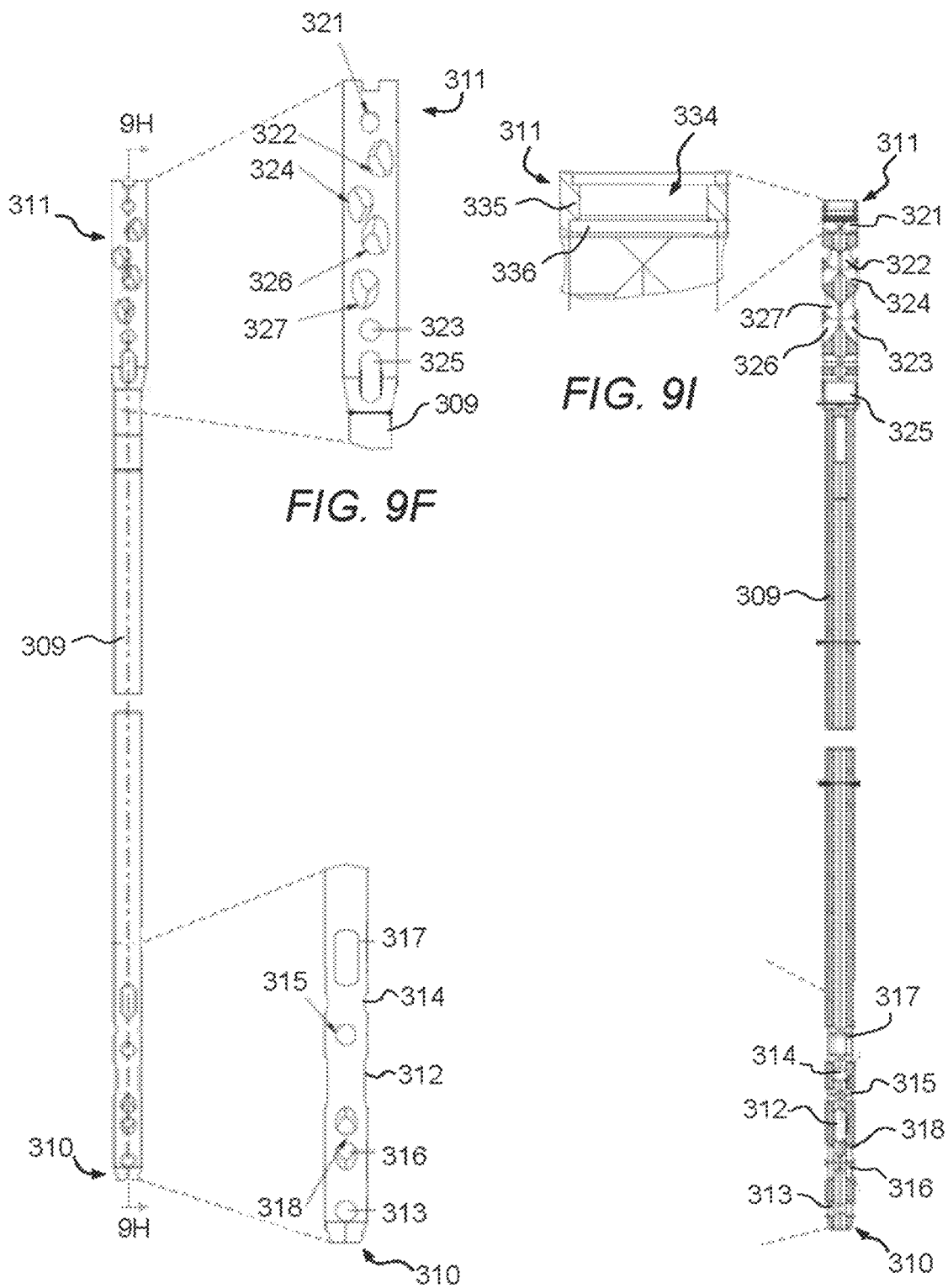

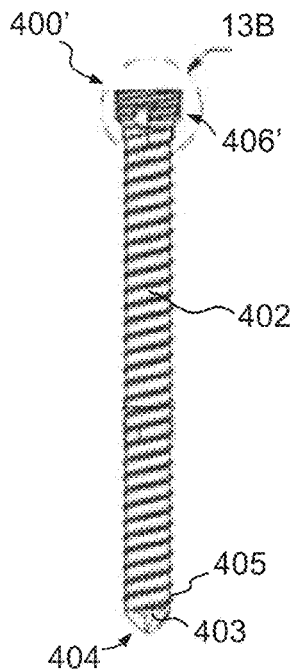
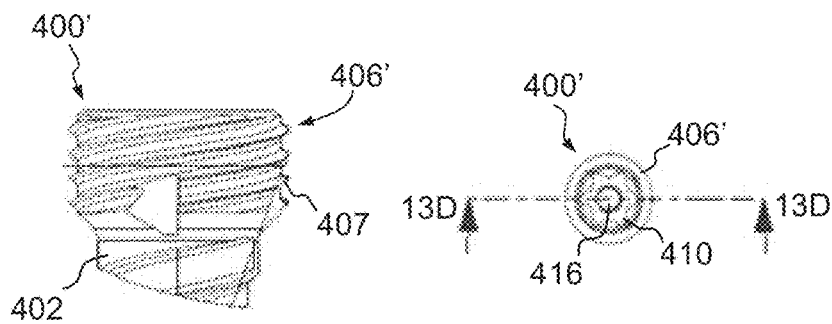
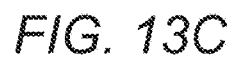
FIG. 13A
FIG. 13B
FIG. 13C
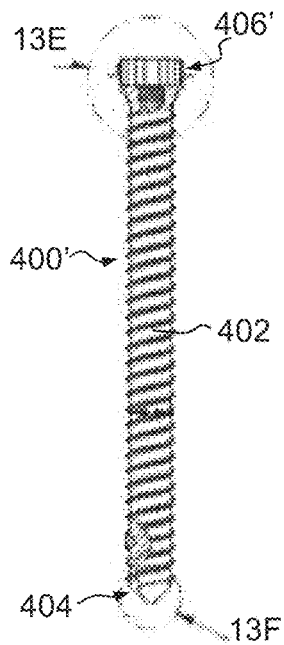
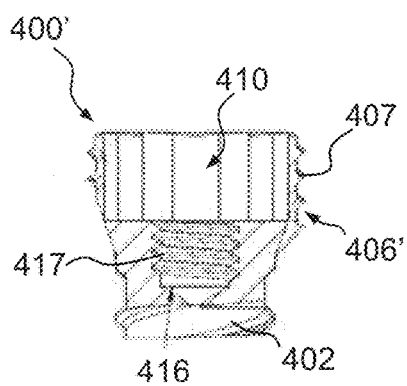
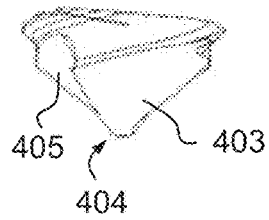
FIG. 13D
FIG. 13E
FIG. 13F

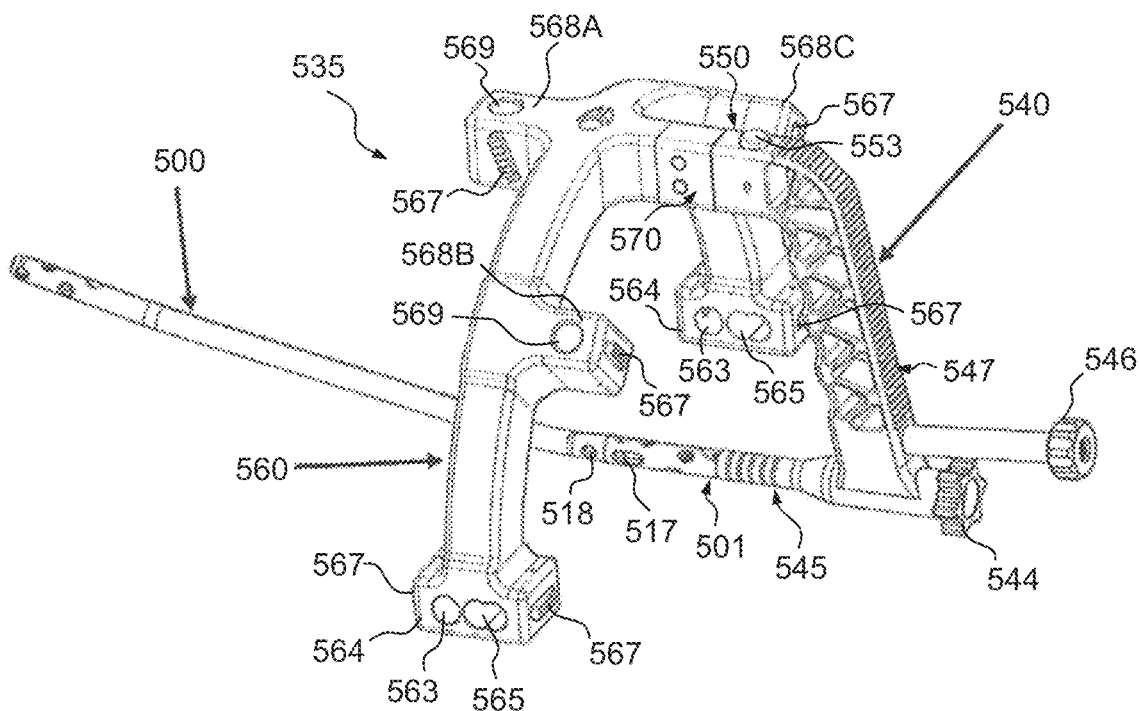
FIG. 17A
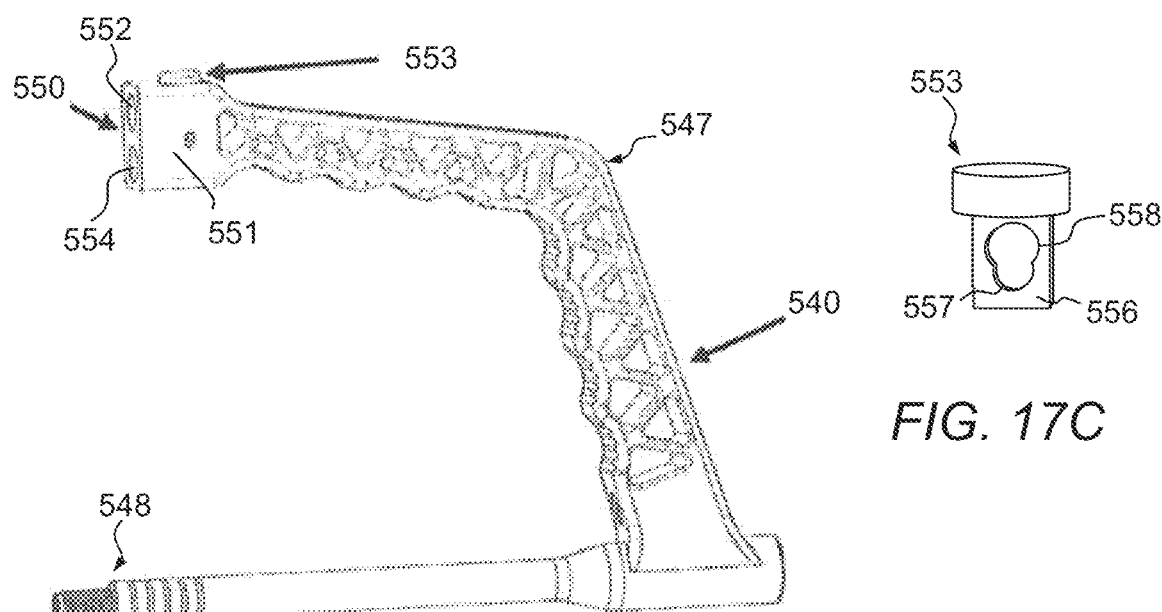
FIG. 17B
FIG. 17C

SYSTEMS AND METHODS FOR INTRAMEDULLARY NAIL IMPLANTATION

CROSS REFERENCE TO RELATED APPLICATIONS

This application is a continuation of U.S. application Ser. No. 16/431,849, filed Jun. 5, 2019 (published as U.S. Pat. Pub. No. 2019-0343569), which is a continuation-in-part of U.S. application Ser. No. 16/153,873, filed Oct. 8, 2018 (now U.S. Pat. No. 10,751,096)), which is a continuation-in-part of U.S. application Ser. No. 15/441,457, filed on Feb. 24, 2017 (now U.S. Pat. No. 10,307,197), which is a continuation-in-part of U.S. application Ser. No. 15/423,773, filed Feb. 3, 2017 (now U.S. Pat. No. 10,251,691), which is a continuation-in-part of U.S. application Ser. No. 15/272,850, filed on Sep. 22, 2016 (now U.S. Pat. No. 10,299,847), the contents of all of which are incorporated herein by reference in their entireties for all purposes.

TECHNICAL FIELD

The present technology is generally related to intramedullary nail implantation for treatment of bone fractures. In particular, several embodiments are directed to systems and methods for implanting an intramedullary nail for immobilizing bone fractures.

BACKGROUND

The significant long bones of the extremities are the humerus, radius and ulna of the upper extremity and the femur and tibia of the lower extremity. Following an injury to the long bone, and in particular, injuries resulting in one or more fractures of the long bone, one or more fixation devices may be used to immobilize the fracture fragments and stabilize the long bone. Bone fractures can be treated with screws or other fixation devices inserted into or through the bone to stabilize it once the fractured portions have been brought into proper alignment. Femoral neck fixation, for example, can be used to treat hip fractures by inserting an intramedullary nail into the medullary cavity of the fractured femur followed by insertion of a fixation screw into the femoral neck/head at an angle relative to the intramedullary nail. Similarly, other long bone fractures can be treated by inserting an intramedullary nail into the intramedullary canal of the bone and providing the appropriate proximal and/or distal fixation. Traditional intramedullary devices may suffer from a number of disadvantages, however. For example, they may be susceptible to implant failure and difficulty in alignment of the fixation screw with respect to the intramedullary nail. Accordingly, there is a need for improved systems and methods for intramedullary nail implantation.

SUMMARY

Intramedullary nails, systems, insertion tools and assemblies, and method of treatment are provided. The intramedullary nails may be suitable for implanting within a medullary canal of a fractured long bone and subsequently providing proximal fixation and/or distal fixation, for example, with one or more anchors, fasteners, fixation screws, or the like. Suitable long bones may include the humerus, radius, ulna, femur, tibia, or the like. Although generally described with reference to the femur and tibia, it will be appreciated that the intramedullary nail and system may be adapted for use with any long bone.

According to one aspect, an intramedullary nail is provided. The intramedullary nail may comprise a generally elongate body extending from a first, distal end to a second, proximal end. The distal end may include one or more openings configured to receive one or more bone anchors or fasteners that extend transversely through the distal end intramedullary nail, and thereby configured to secure the distal end of the nail. The proximal end may also include one or more openings configured to receive one or more bone anchors or fasteners that extend transversely through the proximal end of the intramedullary nail, and thereby configured to secure the proximal end of the nail.

In one aspect, a system for inserting an intramedullary nail into a bone is provided. The system includes an intramedullary nail with an opening or aperture formed therein. An insertion tool can temporarily engage with an end of the intramedullary nail during implantation, and release from the nail once the procedure is complete. A receiving feature for a guide sheath (e.g., a hole, recess, etc.) is disposed in the handle portion and can receive a guide sheath therethrough. The receiving feature defines an axis such that, when the intramedullary nail is coupled to the coupling portion, a guide sheath inserted through the receiving feature substantially aligns with the aperture in the intramedullary nail. A first retention member is disposed in the insertion tool adjacent to the guide sheath receiving feature. The first retention member can interact with a second retention member on the guide sheath to form a ratchet-like mechanism that restrict movement of the guide sheath with respect to the receiving feature. A retention release mechanism can be located on a lower portion (e.g., a bottom surface) of the insertion tool. A guide wire receptacle (e.g., a hole, recess, etc.) can receives a guide wire therethrough and is positioned such that, when the intramedullary nail is coupled to the coupling portion, a guide wire inserted through the receiving feature runs along an axis adjacent to the side surface of the intramedullary nail.

In another aspect, a method for inserting an intramedullary nail into a patient is provided. The method includes inserting a nail into a medullary canal of a patient along a first axis. For insertion, the nail is coupled at its proximal end to an insertion tool. A guide wire is inserted through a guide wire hole in the insertion tool along a second axis such that the guide wire runs nearby or adjacent to a side surface of the nail. A screw or other bone fixation device is inserted through a receptacle (e.g., a hole, recess, or other suitable structure) formed in the insertion tool such that the screw passes through an aperture formed in the nail.

In accordance with another aspect, an implant is provided. The implant includes an intramedullary nail that is elongated along a first axis. First and second openings or apertures are disposed in a proximal portion of the nail. The first aperture defines a second axis transverse to the first axis, and the second aperture defines a third axis transverse to the first axis. The third axis intersects with the second axis at a point spaced apart from the nail. In some embodiments, the first screw can be inserted through the first aperture along the second axis and a second screw can be inserted through the second aperture along the third axis. The second screw can be at least partially inserted through a slot in the first screw such that the two screws interlock. The second screw can be shorter than the first screw but long enough that at least a threaded distal tip extends beyond the slot in the first screw to provide some purchase in the bone.

In accordance with another aspect, an implant is provided. The implant includes an intramedullary nail having a body elongated along a first axis. The body has a proximal portion and a distal portion. A first aperture is formed in the proximal portion and defines a second axis transverse to the first axis at a first angle. A second aperture is formed in the proximal portion and defines a third axis transverse to the first axis at a second angle. The third axis intersects with the second axis at the first axis and the first and second angles are complementary angles.

In accordance with another aspect, an intramedullary system configured to stabilize bone is provided. The system comprises an intramedullary nail and one or more headless fasteners or screws. The headless fastener extends from a first end to a second end. The headless fastener has a shaft configured to be positioned through the first aperture or the second aperture in the intramedullary nail and the first end (e.g., in some instances a threaded head) of the headless fastener is configured to be positioned against or within the bone. Unlike traditional headed screws which sometimes cause pain or irritation to patients, one or more headless screws or fasteners can be used when securing the distal and/or proximal ends of the intramedullary nail, thereby resulting in a system with superior patient outcomes.

In accordance with another aspect, a system for inserting an intramedullary nail into a bone is provided. The system includes an intramedullary nail having a proximal end, a distal end, at least one side surface extending between the proximal end and the distal end, and an aperture through the intramedullary nail. An insertion tool includes a handle portion, a coupling portion and an aiming guide. The handle portion defines a first connection assembly. The coupling portion extends from the handle portion and is configured to removably couple to the proximal end of the intramedullary nail. The aiming guide has a body with at least one support block and a second connection assembly. The first and second connection assemblies are configured to releasably interconnect the handle portion and the aiming guide. The at least one guide block defines a guide sheath hole configured to receive a guide sheath therethrough. The guide sheath hole is positioned such that, when the intramedullary nail is coupled to the coupling portion, the guide sheath hole substantially aligns with the aperture in the intramedullary nail.

In accordance with another aspect, a connection assembly for interconnecting an intramedullary nail and insertion tool is provided. The intramedullary nail extends between a proximal end and a distal end and has a circumferential slot defined within the proximal end. The insertion tool includes an aiming arm with a hole defined therein. The connection assembly includes an alignment tip having a hollow body extending from a proximal end to a distal end with the proximal end configured to be securely connected within the hole of the aiming arm. An expanding collet has a hollow body extending from a collet proximal end to a collet distal end. The collet distal end has a radially outwardly extending collar and internal threads. The collet body defines axial slots extending from the distal end of the body which allow the distal end of the body to compress radially inwardly, thereby allowing the collar to pass through the alignment tip through passage and into the circumferential slot of the intramedullary nail. A connecting bolt has a threaded shaft and extends through the hole in the aiming arm and into threaded engagement with the internal threads of the expanding collet such that the collar is pushed outwardly to its major diameter.

Also provided are kits including intramedullary nails of varying shapes and sizes, bone anchors, fasteners, insertion tools, and components for installing the same.

According to still another aspect, an aiming guide for inserting an intramedullary nail into a bone includes a generally arcuate or "J-shaped" body having an elongate proximal handle portion and a generally arcuate distal implant alignment tip connector portion having a distal implant alignment tip extending parallel to a longitudinal axis of the proximal handle portion. The handle portion includes a first attachment location for releasably attaching a first module and the distal implant alignment tip portion includes a second attachment location for releasably attaching a second module.

In accordance with yet another aspect, an aiming guide assembly includes a generally "J-shaped" aiming guide having an elongate proximal handle portion and a generally arcuate distal implant alignment tip connector portion. The distal implant alignment tip connector portion has a distal implant alignment tip extending along a tip axis parallel to a longitudinal axis of the proximal handle portion. A recon module is releasably attached to a proximal end of the proximal handle portion and an oblique module is releasably attached to the distal implant alignment tip portion.

According to another aspect, an aiming guide assembly includes an aiming guide having an elongate proximal handle portion and a generally arcuate distal implant alignment tip connector portion. The aiming guide has an elongate proximal handle portion and a generally arcuate distal implant alignment tip connector portion. The distal implant alignment tip connector portion has a distal implant alignment tip extending along a tip axis parallel to a longitudinal axis of the proximal handle portion. A first attachment is releasably attached to a proximal end of the proximal handle portion and a second attachment is releasably attached to the distal implant alignment tip portion.

According to another aspect, an aiming guide for inserting an intramedullary nail into a bone includes a collet configured to engage the intramedullary nail, a connection bolt configured to engage the collet to connect the collet with the intramedullary nail, and a connection bolt driver configured to engage the connection bolt. The connection bolt may include a head containing a circlip. The circlip may be configured to splay open upon insertion of the connection bolt driver into the head and provide tension around the connection bolt driver to retain the connection bolt driver in the head of the connection bolt.

According to another aspect, an aiming guide for inserting an implant into a bone includes a collet configured to engage the intramedullary nail, a connection bolt configured to engage the collet to connect the collet with the implant, and a connection bolt driver configured to engage the connection bolt. The connection bolt may include a head containing a circlip. The circlip may be configured to splay open upon insertion of the connection bolt driver into the head and provide tension around the connection bolt driver to retain the connection bolt driver in the head of the connection bolt.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIGS. 4A-4D illustrate various views of an intramedullary nail and a first fixation device.

FIGS. 5A-5D illustrate various views of the first fixation device inserted through the intramedullary nail.

FIGS. 6A-6D illustrate various views of a second fixation device and the intramedullary nail with the first fixation device inserted therein.

FIGS. 7A-7D illustrate various views of the second anchor inserted through the intramedullary nail and the first fixation device.

FIGS. 8A-8C illustrate steps of implanting an intramedullary nail with interlocking fixation devices into a fractured femur.

FIGS. 13A-13F illustrate various views of a headless locking screw.

FIGS. 17A-17L illustrate various views of illustrative insertion systems.

DETAILED DESCRIPTION

Figure 1A:
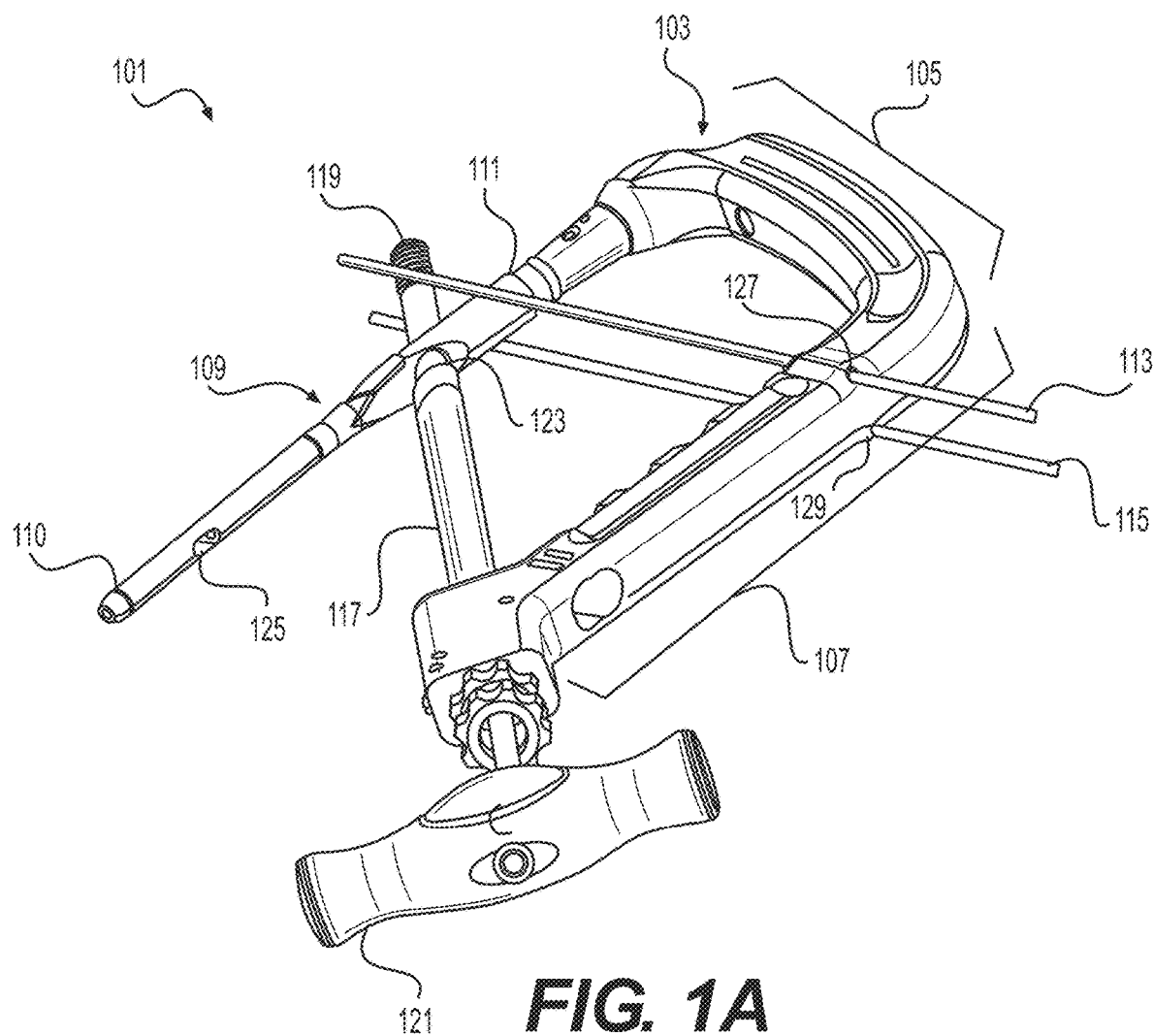
FIGS. 1A and 1B illustrate a system for implanting an intramedullary nail.

In the drawings, like numerals indicate like elements throughout. Certain terminology is used herein for convenience only and is not to be taken as a limitation on the present device. The terminology includes the words specifically mentioned, derivatives thereof and words of similar import. The embodiments illustrated below are not intended to be exhaustive or to limit the device to the precise form disclosed. These embodiments are chosen and described to best explain the principle of the device and its application and practical use and to enable others skilled in the art to best utilize the device.

Reference herein to "one embodiment" or "an embodiment" means that a particular feature, structure, or characteristic described in connection with the embodiment can be included in at least one embodiment of the device. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Intramedullary nails, systems, insertion tools, and method of treatment are provided. The intramedullary nails may be suitable for implantation within the intramedullary canal of a fractured long bone and subsequently providing proximal fixation and/or distal fixation, for example, with one or more anchors, fasteners, fixation screws, or the like. Suitable long bones may include the humerus, radius, ulna, femur, tibia, or the like. Although further described with reference to hip fractures of the femur or fractures of the tibia, it will be appreciated that the intramedullary nail and system may be adapted for use with any long bone.

In conventional hip fracture fixation techniques, there are four main failure modes: axial cutout, cephalad cutout, proximal fragment rotation, and nonunion. "Cutout" is the term for hip screw subsidence into the articular surface of the hip. Cutout can occur in either a cephalad (toward the head) or axial direction (along the axis of the hip screw). Axial cutout is the result of an implant with a small axial profile that provides little resistance to axial translation. Axial cutout can be addressed by the "controlled collapse" features on certain modern hip fracture nails; the hip screw is allowed to translate through the nail, even after the set screw is locked in place. Cephalad cutout is the radial translation of the nail which is the result of a narrow implant that "windshield wipers" through the weak cancellous bone in the hip. Proximal fragment rotation is the result of a circular profile hip screw that acts as a fulcrum to the proximal hip fragment. Fracture nonunion is the result of biologic or mechanical factors that are incompatible with the bone healing process. Biologic factors of the patient are not controllable by the implant. Mechanical factors are those that typically allow fixation that is too rigid or too flexible. Nonunion is usually the precursor to one of the other three failure modes. Occasionally, nonunion will cause the nail to break in fatigue before the bone fails.

The intramedullary nails and systems described herein may address one or more of these failure modes. In some embodiment, the intramedullary nail includes proximal and distal locking, for example, to prevent cutout. In other embodiments, the intramedullary nail may include proximal locking including two interlocking fixation devices (e.g., screws), for example, by providing converging and diverging purchase, along with bony fixation in the calcar of the femur, which is the strongest portion of the hip bone. Accordingly, the risk of failure due to cutout and/or rotation can be reduced.

Additionally, some intramedullary nail implantation systems fail to adequately address the problems of fragment rotation during implantation. Rotation occurs when fragments of the bone rotate about the axis of the screw during the implantation procedure. Conventional anti-rotation technologies require the use of additional instruments or are limited to a single wire placement. In some embodiments, an insertion tool is directly coupled to the intramedullary nail and additional instruments are not needed for the placement of an anti-rotation guide wire and allow the user to place one or more guide wires anterior and/or posterior to the nail. These guide wires can be positioned to prevent the distal fragments of the femoral head and neck from rotating about the axis of the anchor during the procedure.

Some systems may be susceptible to backout during the implantation procedure. Backout occurs when the guide sheath used to insert the screw through the intramedullary nail moves proximally away from the bone. Conventional systems either have no features to prevent backout or else provide backout prevention measures that obstruct the normal positioning of the hands during the procedure, resulting in the risk of releasing the guide sheaths and dropping them to the floor. Ratchets on the insertion tool may have the release button facing towards the grip portion on the insertion tool and may present the danger of the user's hand slipping and inadvertently pressing the button. Accidentally pressing the button could result in releasing the sheath and causing the sheath to fall on the floor. In some embodiments, a backout prevention system (e.g., a ratchet system) may be disposed on the lower end of the insertion tool, which allows a user to have a hand placed on the grip of the insertion tool without the risk of inadvertently pressing the ratchet release button.

Further specific details of several embodiments of the present technology are described below with reference to FIGS. 1A-8C. Although many of the embodiments are described below with respect to devices, systems, and methods for implantation of intramedullary nails, other embodiments are within the scope of the present technology. Additionally, other embodiments of the present technology can have different configurations, components, and/or procedures than those described herein. For example, other embodiments can include additional elements and features beyond those described herein, or other embodiments may not include several of the elements and features shown and described herein.

For ease of reference, throughout this disclosure identical reference numbers are used to identify similar or analogous components or features, but the use of the same reference number does not imply that the parts should be construed to be identical. Indeed, in many examples described herein, the identically numbered parts are distinct in structure and/or function.

Figure 3A:
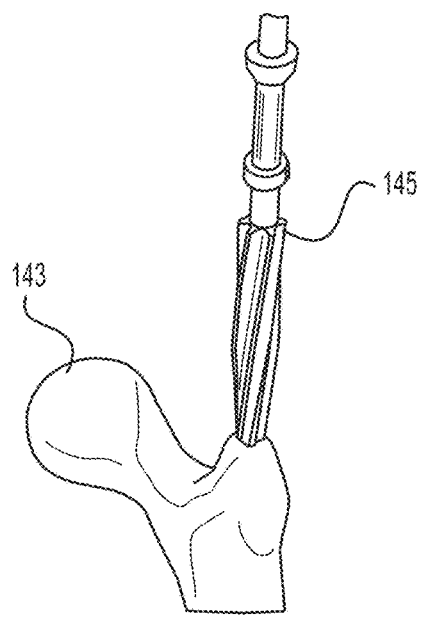
FIGS. 3A-3F illustrate steps of implanting an intramedullary nail into a fractured femur.
Figure 3B:
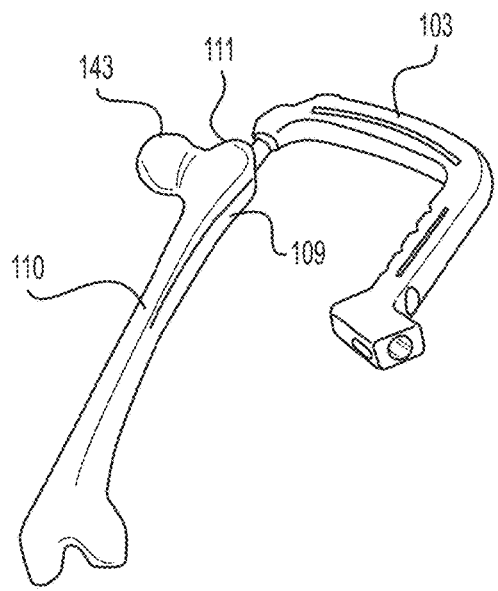
Figure 3C:
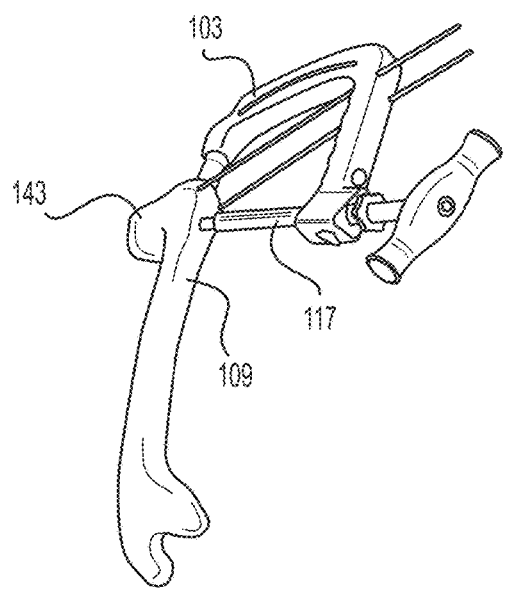
Figure 3D:
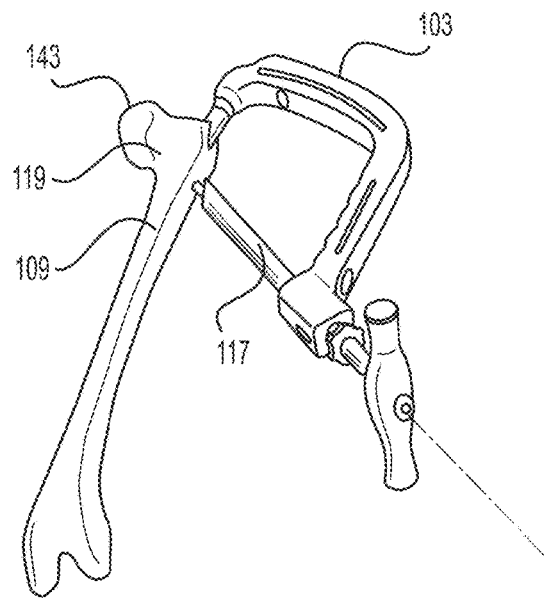
Figure 3E:
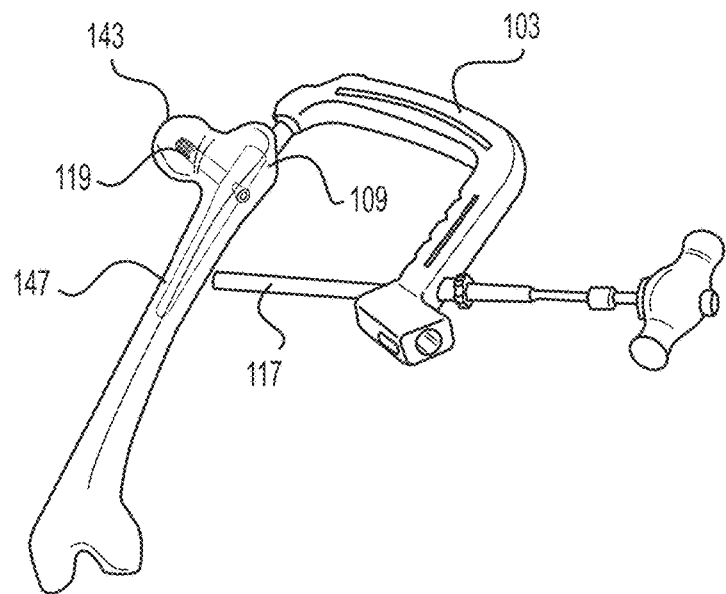
Figure 3F:
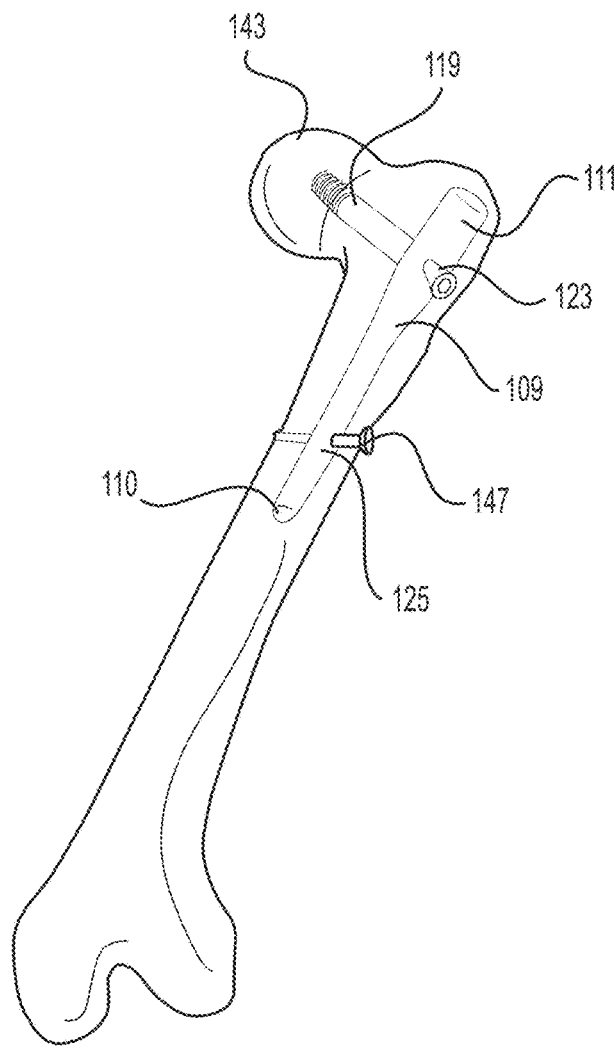
Figure 4D:
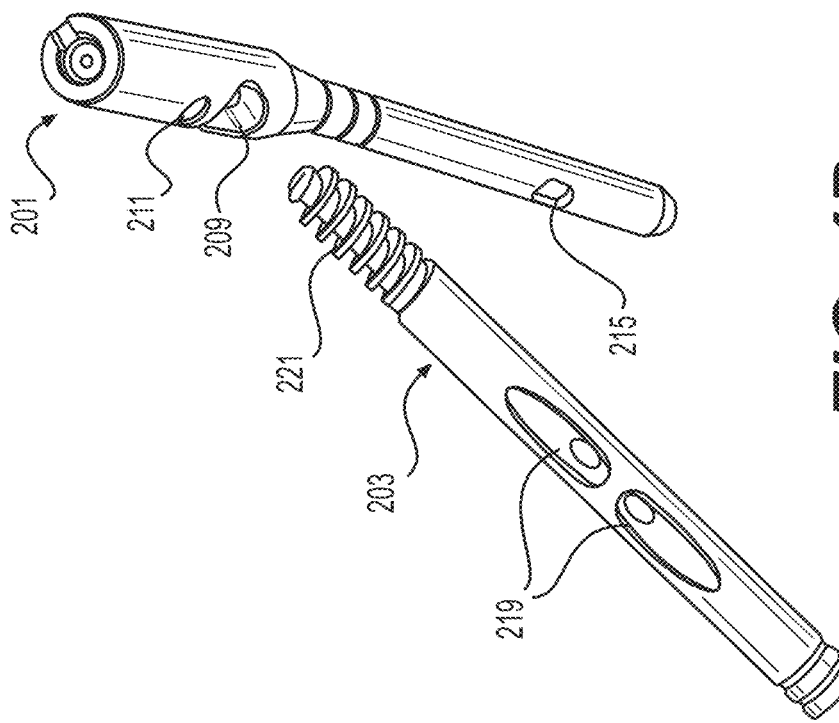
Figure 4C:
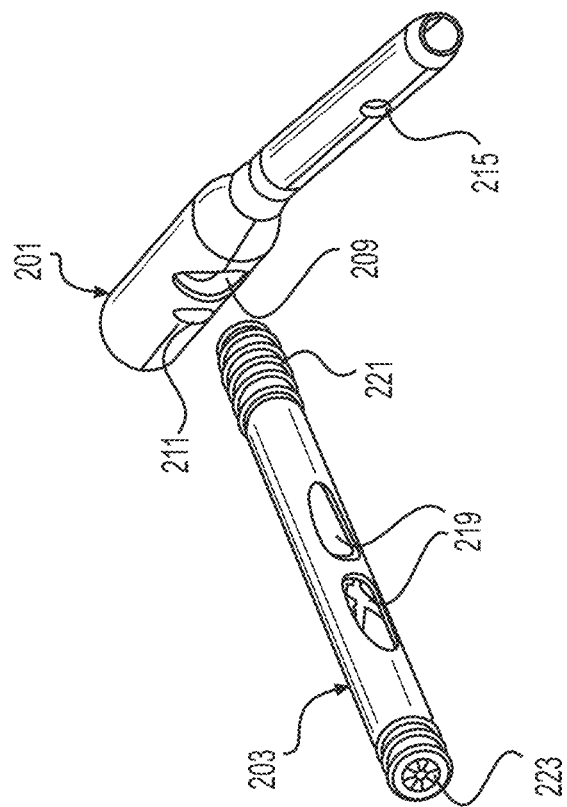
Figure 5D:
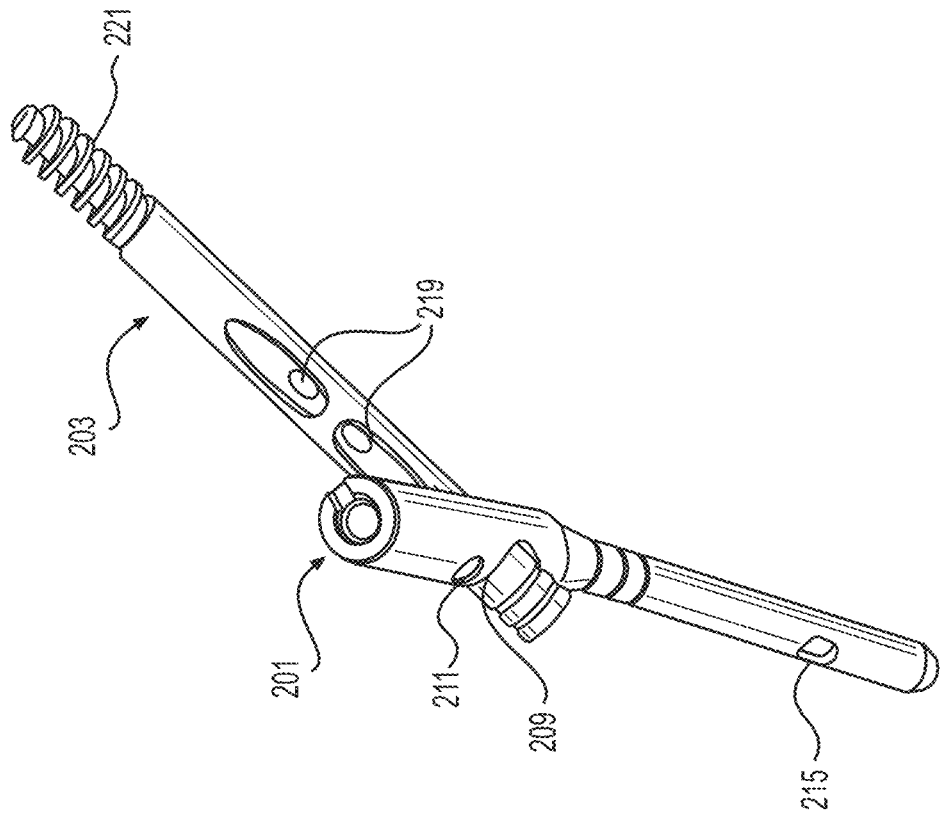
Figure 5C:
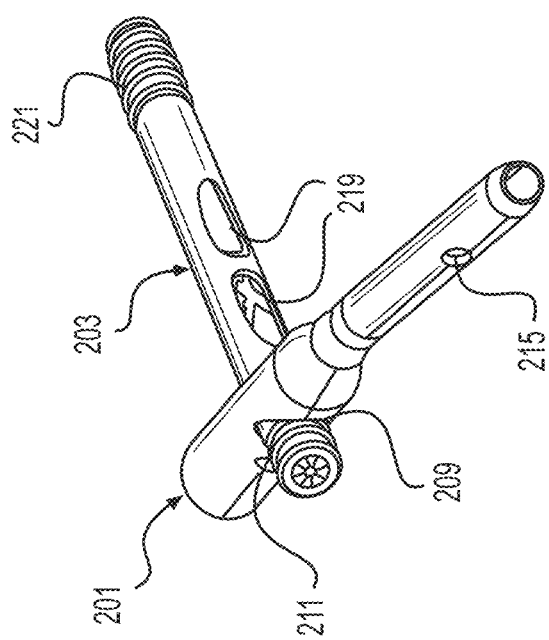

FIGS. 1A and 3F illustrate one example of an intramedullary nail 109, which may comprise a generally elongate body extending from a first, distal portion or end 110 to a second, proximal portion or end 111. The elongate body may be in the form of an elongate tubular rod configured to extend longitudinally within the intramedullary canal of a fractured bone. The elongate rod may be hollow or may be solid along its length. The elongate body may be substantially straight along a longitudinal axis of the nail 109 or may comprise one or more curves or bends to conform to the anatomical shape of the intramedullary canal. The cross-section of the nail 109, taken at a right angle to a central longitudinal axis of the intramedullary nail 109, may be circular, oval, elliptical, or of any other suitable cross-dimensional shape. The proximal portion 111 may have an enlarged diameter or head portion relative to the distal portion 110 of the nail 109. The enlarged head portion 111 may be sized and configured to be received in the greater trochanter region of the femur. The intramedullary nail 109 may be configured to be positioned in the proximal end of the femur for cephalomedullary fixation. It is envisioned, however, that the intramedullary nail 109 may be configured to be positioned through other approaches and locations (e.g., distal end) depending on the bone (e.g., femur, tibia) and type of fracture.

The distal end 110 may include one or more openings 125 configured to receive one or more bone anchors, fasteners, or distal fixation devices 147 that extend transversely through the distal end 110 of the intramedullary nail 109, and are thereby configured to secure the distal end 110 of the nail 109 within the canal. The distal fixation devices 147 may include a bone screw or anchor configured for distal locking of the nail 109. The distal fixation device 147 may include traditional polyaxial or fixed angle locking bone screws and anchors known in the art.

The proximal end 111 may also include one or more openings 123 configured to receive one or more bone anchors or fasteners 119 that extend transversely through the proximal end 111 of the intramedullary nail 109, and are thereby configured to secure the proximal end 111 of the nail 109 within the canal. The proximal fixation devices 119 may include a bone screw or anchor configured for proximal locking of the nail 109. The fixation device 119 may be a calcar screw or anchor configured to be aimed at a calcar region of the proximal humerus, which may constitute the best quality bone in the region. The opening 123 and anchor 119 may be angled about 100-150°, 110-140°, or about 120-135° relative to the nail 109 to engage the calcar region of the bone. The calcar screw 119 may have an enlarged diameter relative to the distal screw 147. The proximal fixation device 119 may include traditional polyaxial or fixed angle calcar screws and anchors known in the art. The proximal end 111 may also include additional openings 123, for example, for one or more cross-locking devices (e.g., device 205 described in more detail below).

The intramedullary nail 109 and anchors 119, 147 may be comprised of any suitable biocompatible materials. The intramedullary nail 109 and anchors 119, 147 may be comprised of titanium, cobalt chrome, cobalt-chrome-molybdenum, stainless steel, tungsten carbide, carbon composite, plastic or polymer—such as polyetheretherketone (PEEK), polyethylene, ultra high molecular weight polyethylene (UEMWPE), resorbable polylactic acid (PLA), polyglycolic acid (PGA), combinations or alloys of such materials, or other appropriate biocompatible materials that have sufficient strength to secure and hold bone, while also having sufficient biocompatibility to be implanted into a body.

Figure 1B:
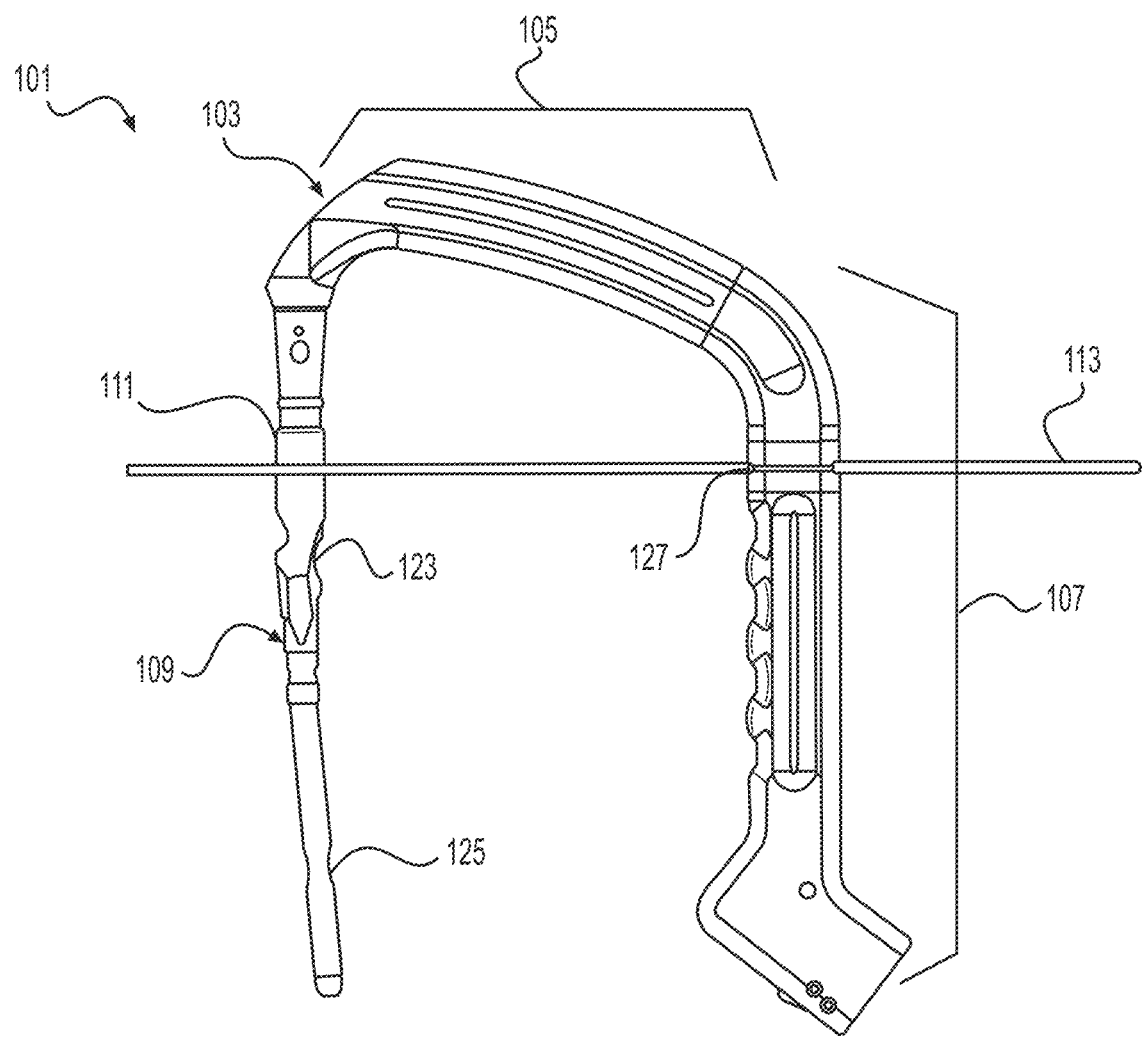

FIGS. 1A and 1B illustrate perspective and side views, respectively, of one embodiment of a system 101 for implanting an intramedullary nail 109. The system 101 includes an insertion tool 103 that has a coupling portion 105 and a handle portion 107. In some embodiments, the coupling portion 105 and the handle portion 107 can be separate parts that are removably joined together, while in other embodiments the coupling portion 105 and the handle portion 107 can be different regions of a single, integrally formed component. The coupling portion 105 releasably engages or couples to the proximal portion 111 of the nail 109. For example, the free end of the coupling portion 105 can be provided with a snap-fit design to temporarily retain a portion of the intramedullary nail 109 prior to insertion of a fixation device 119 therethrough. However, those skilled in the art will understand that other coupling mechanisms may be employed.

The handle portion 107 may include one or more openings 127, 129 configured to receive one or more guide wires 113, 115. In one embodiment, the system 101 may include first and second guide wires 113, 115 as well as an optional guide sheath 117 through which the fixation device 119 may pass (e.g., the fixation device 119 can be inserted using the driver 121). As illustrated, the first and second guide wires 113, 115 may pass on opposing sides of both the nail 109 and the fixation device 119 (e.g. on posterior and anterior sides). Although the illustrated embodiment shows two guide wires, in other embodiments a single guide wire and corresponding guide wire hole may be used. In still other embodiments, three or more guide wires may be used. Additionally, the position and orientation of the guide wire holes can vary in different embodiments, for example being disposed more proximally or more distally along the insertion tool, etc.

As illustrated, the insertion tool 103 allows the user to place one or more guide wires 113, 115. In one embodiment, the guide wires 113, 155 are positioned both anterior and posterior to the nail 109. The guide wires 113, 115 may be positioned in this manner to prevent the distal fragments of the bone (e.g., distal fragments of the femoral head and neck) from rotating about the axis of the fixation device 119 when the fixation device 119 is advanced through the nail 109 and into the bone during the procedure. The handle portion 107 of the insertion tool 103 may include two guide wire receiving features such as holes 127, 129 on the opposing sides of the tool 103 that allow guide wires 113, 115 to pass through the respective holes. The guide wires 113, 115 are passed through the soft tissue and into the bone to help stabilize the insertion tool 103. In this configuration, the insertion tool 103 may not require any other instruments to guide the wires 113, 115 into the patient. The insertion tool 103 can achieve stability by resisting both rotational movement about the axis of the nail 109 as well as axial translation along the axis of the nail 109.

Figure 2A:
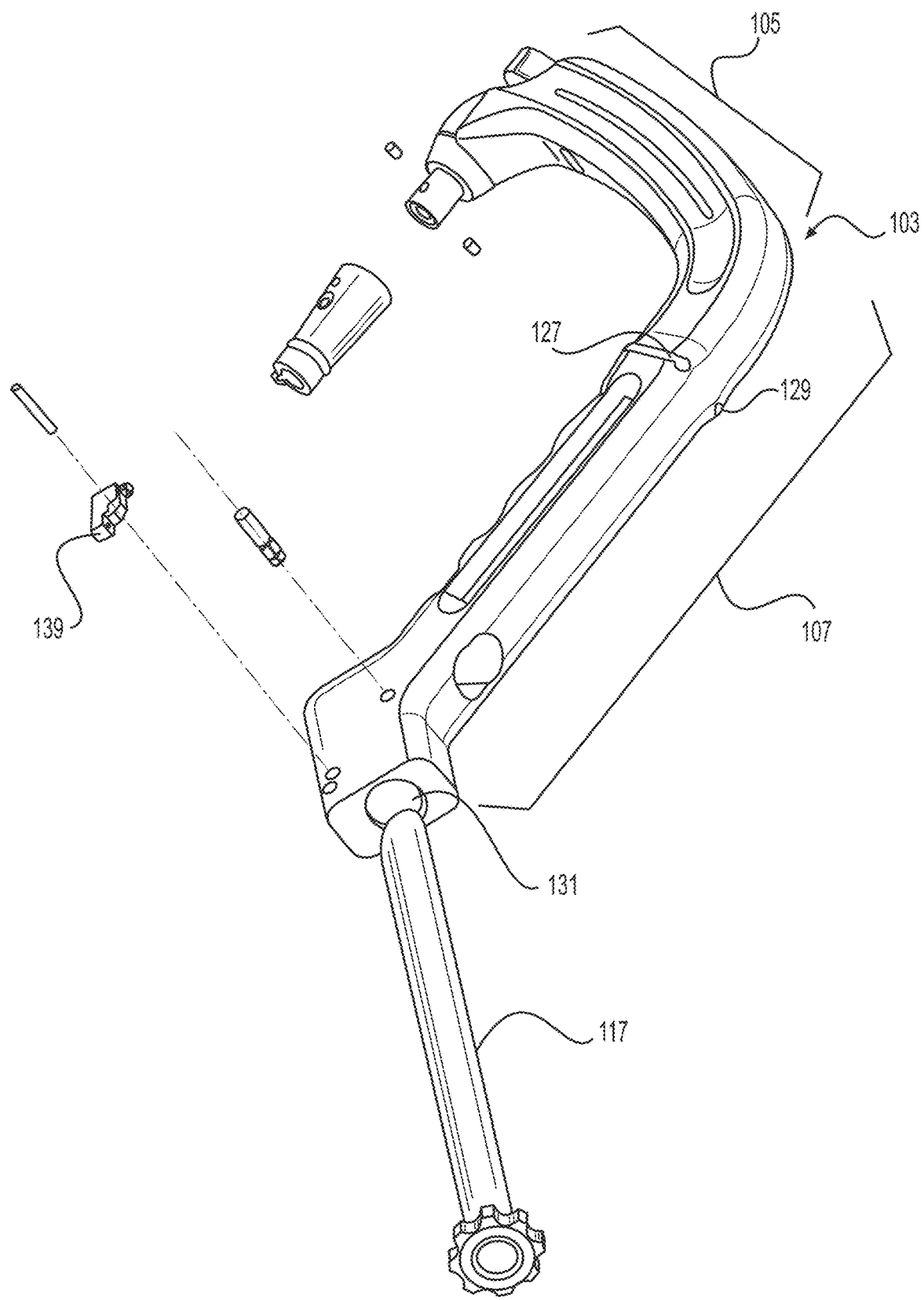
FIGS. 2A-2C illustrate various views of an insertion handle of the system shown in FIGS. 1A and 1B.
Figure 2B:
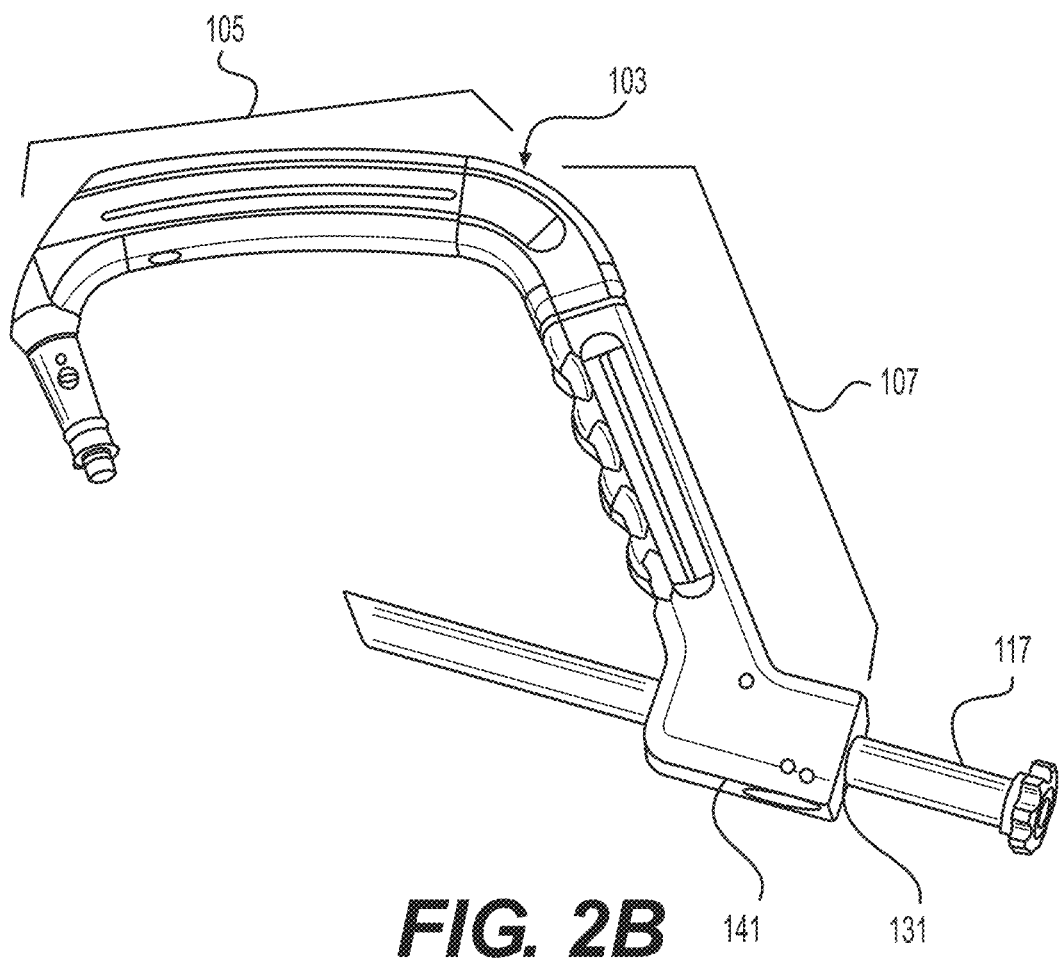
Figure 2C:
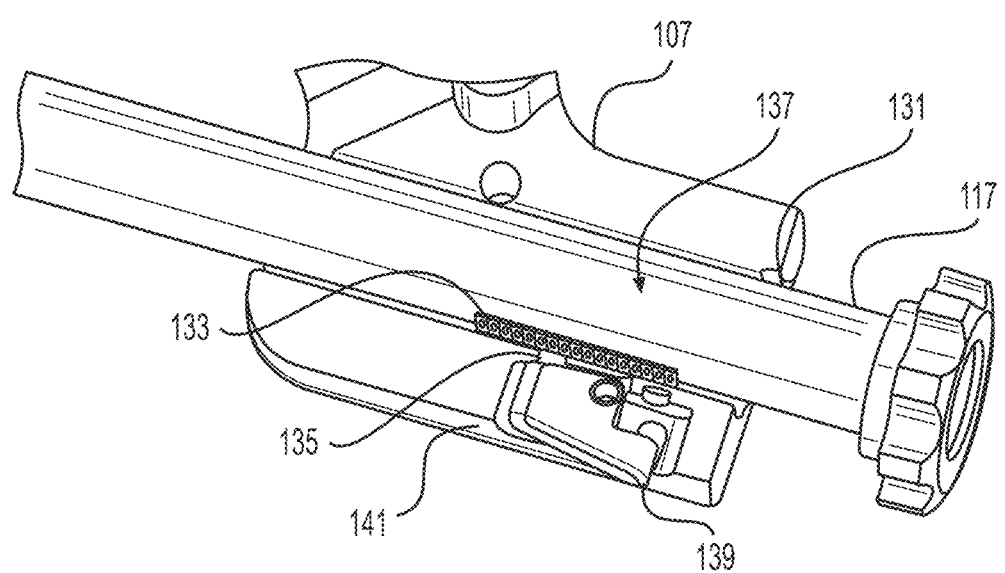

FIGS. 2A-2C illustrate various views of the insertion tool 103 of the system 101 shown in FIGS. 1A and 1B. In particular, FIG. 2A is a partially exploded perspective view of the insertion tool 103 adjacent to the guide sheath 117, FIG. 2B is a perspective view of the insertion tool 103 with the guide sheath 117 partially inserted therein, and FIG. 2C is an enlarged partial cross-sectional view of the engagement between the guide sheath 117 and the insertion tool 103.

The guide sheath 117 can be removably inserted through a guide sheath receiving feature such as a hole 131 formed in the handle portion 107 of the insertion tool 103. The guide sheath hole 131 defines an axis that intersects with a first aperture 123 in the nail 109. The guide sheath 117 can be positioned through the guide sheath hole 131 such that it substantially aligns with the first aperture 123 in the nail 109, which is configured to receive fixation device 119 aimed at the calcar region of the bone. The guide sheath 117 can include a first retention member 133 on an outer surface of the guide sheath 117. The first retention member 133 can include, for example, ridged teeth, protrusions, or other such surface configured to engage with a corresponding second retention member 135 disposed within the guide sheath hole 131. The second retention member 135 can likewise include one or more ridges or protrusions. Together the first and second retention members 133, 135 form a retention mechanism 137 that allows the guide sheath 117 to be ratcheted towards the intramedullary nail 109 while restricting movement of the guide sheath 117 away from the intramedullary nail. The retention release mechanism 139 can disengage the second retention member 135 from the first retention member 133 when pressed by a user. For example, the retention release mechanism 139 can be a button disposed on a lower surface 141 of the handle portion 107. Positioning this retention release mechanism 139 on the lower surface 141 of the insertion handle may prevent a user from accidentally releasing the guide sheath 117 while operating the device (e.g., while grasping the handle portion 107).

FIGS. 3A-3F illustrate one method of steps of implanting an intramedullary nail into a fractured femur 143. Referring first to FIG. 3A, a proximal end of the femur 143 can be accessed and the medullary cavity of the femur 143 can be reamed using a bone drill and reamer 145. Next, as shown in FIG. 3B, the intramedullary nail 109 is coupled to the insertion tool 103 and the intramedullary nail 109 is disposed within the reamed cavity of the femur 143. In FIG. 3C, when used, one or more of the first and second guide wires 113 and 115 may be inserted through the soft tissue, for example, along parallel trajectories on opposing sides of the nail 109. The guide wires 113, 115 can limit or prevent inadvertent rotation of distal fragments of the femur 143 after the nail 109 is in position. The proximal fixation device 119 (e.g., a lag screw or other suitable bone anchor) is also passed through the first aperture 123 in the nail 109 and into the head/neck region of the femur 143. In FIG. 3D, the guide wires 113, 115 are retracted and in FIG. 3E, the distal fixation device 147 can additionally be inserted through the distal aperture 125 in the nail 109. The distal device 147 can be positioned using the guide sheath 117, which is positioned through another opening in the handle portion 107, such that the sheath 1117 is aligned with the distal opening 125 in the nail 109. In FIG. 3F, the insertion tool 103 is disengaged from the nail 109, which is now secured in place via the proximal fixation device 119 and the distal fixation device 147. As shown, the nail 109 may extend along a portion of the length of femur 143. It is also contemplated, however, that the nail 109 may be of different sizes and shapes, for example, of longer lengths and/or different diameters to accommodate different anatomies and fractures.

FIGS. 4A-4D illustrate another embodiment of an intramedullary nail 201, similar to intramedullary nail 109, with the addition of a cross-locking feature for proximal locking of the nail 201. Intramedullary nail 201 may include any of the features described above with respect to intramedullary nail 109. Intramedullary nail 201 may further include two interlocking proximal fixation devices 203, 205 (e.g., bone anchors, fasteners, or screws), for example, by providing converging and diverging purchase, along with bony fixation in the calcar of the femur 229, which is the strongest portion of the hip bone. Accordingly, the risk of failure due to cutout and/or rotation may be reduced.

FIGS. 4A-4D show side, side cross-sectional, and two perspective views, respectively, of the intramedullary nail 201 adjacent to a first fixation device 203. FIGS. 5A-5D illustrate side, side cross-sectional, and two perspective views, respectively, of the first, proximal fixation device 203 inserted through the intramedullary nail 201. FIGS. 6A-6D illustrate side, side cross-sectional, and two perspective views, respectively, of the system with a second, cross-locking fixation device 205 adjacent to the intramedullary nail 201 with the first fixation device 203 inserted therein. FIGS. 7A-7D illustrate side, side cross-sectional, and two perspective views, respectively, of the system with the second fixation device 205 inserted through both the intramedullary nail 201 and the first fixation device 203, thereby creating a cross-locking feature for proximal locking of the nail 201.

Referring to FIGS. 4A-8C together, the intramedullary nail 201 is configured to receive both the first and second fixation devices 203 and 205 therein. The intramedullary nail 201 includes an elongated body 207 having first and second apertures 209 and 211 formed therethrough in a proximal region 213, as well as a third aperture 215 formed in a distal region 217. The first aperture 209 can be sized and configured to receive the first fixation device 203 therethrough and the second aperture 211 can be sized and configured to receive the second fixation device 205 therethrough.

The first fixation device 203, may be the same or similar to the proximal fixation device 119, described herein, and may include a bone screw or anchor configured for proximal locking of the nail 201. For example, the first fixation device 203 may be a calcar screw or anchor configured to be aimed at a calcar region of the proximal humerus. The calcar screw 203 may have a threaded portion at its distal tip and a non-threaded portion along a substantial length of the screw 203. The calcar screw 203 may include traditional polyaxial or fixed angle calcar screws and anchors known in the art.

The second fixation device 205 may also include a bone screw or anchor configured for proximal locking of the nail 201. This bone anchor or screw 205 may be substantially smaller in length and diameter relative to the calcar screw 203. The bone anchor or screw 205 is substantially sized and configured to be positioned through second opening 211 in the proximal end of the nail 201 and into a channel 219 in the first fixation device 203. Thus, the second device 205 is configured to interlock with the first fixation device 203, for example, enhanced purchase and bony fixation to the bone. Although shown with the second fixation device 205 positioned above the first fixation device 203 and angled downwardly into contact with the first fixation device 203, it is also envisioned that these relative positons may be reversed or the fixation devices 203, 205 may otherwise be angled with respect to one another in order to interlock the devices 203, 205 with one another. The second fixation device 205 may be configured to pass through a slot or channel 219 formed in the first fixation device 203. This interlocking feature of the first and second fixation devices 203, 205 can prevent cutout and rotation by providing converging and diverging purchase. In the case of a femur, this can also provide bony fixation in the calcar. The elongated slot 219 in the first fixation device 203 allows for controlled collapse, which leverages the natural compression between fragments from weight bearing or ligamentotaxis. Limited collapse is controlled by the length of the slot 219 to prevent the uncontrolled and excessive shortening of the femoral neck. The first fixation device 203 may include distal threads 221 and a proximal drive interface 223 configured to engage with a driver (not shown). The second fixation device 205 may have a narrower diameter than the first fixation device 203 such that the second fixation device 205 can pass through the slot 219 in the first fixation device 203. The second fixation device 205 may also include distal threads 225 and a proximal drive interface 227 configured to engage with a driver (not shown).

The slot 219 can be disposed in the mid-shaft of the first fixation device 203 and may be sized and configured to allow the second fixation device 205 to pass therethrough. The slot 219 may be longer than necessary to allow translation of the first fixation device 203 after the second fixation device 205 is in place. The slot 219 may be strong enough to prevent rotation of the first fixation device 203 after the second fixation device 205 is in position. The slot 219 may have beveled proximal and distal edges to maximize material in the first fixation device 203 while allowing proximal and distal clearance of the second fixation device 205. The slot 219, in the first fixation device 203, may be symmetric to allow positioning of the second fixation device 205 in 180° increments, for example.

In at least one embodiment, a locking device 230, such as a set screw or washer, may be used to lock the first and/or the second fixation devices 203, 205 into position. As best seen in FIG. 7B, the locking device 230 may be threaded through a hollow interior portion of the nail 201. The locking device 230 may have external threads, which are sized and configured to correspond to mating internal threads along the hollow interior portion of the nail 201. As the locking device 230 is threaded downwardly and comes into contact with the first or second fixation devices 203, 205, the respective fixation device 203, 205 is locked into position relative to the nail 201. In some embodiments, the interlocking fixation devices 203, 205 can be used selectively. For example, the threaded locking device 230 may be threaded to engage the second fixation device 205; alternatively, the threaded locking device 230 may be threaded further down to lock the first fixation device 203, for example, if the second fixation device 205 is not used. This allows users the choice of a traditional or interlocking construct intraoperatively.

An insertion tool 103 for implanting the system including the nail 201 and the interlocking first and second fixation devices 203 and 205 can be substantially similar to the system 101 described above with respect to FIGS. 1A-2C, except that an additional guide sheath hole may be formed in the handle portion 107 to accommodate a guide sheath along an appropriate trajectory to insert the second fixation device 205 through the second aperture 211 in the nail 201 and into engagement with the first fixation device 203.

FIGS. 8A-8C illustrate one method of steps of implanting an intramedullary nail 201 with interlocking fixation devices 203, 205 into a fractured femur 229. Referring first to FIG. 8A, the nail 201 has been inserted into a reamed medullary cavity of the femur 229 and the first fixation device 203 has been inserted through the first aperture 209 in the nail 201, similar to the technique described above with respect to FIGS. 3A-3D. Referring to FIG. 8B, a distal fixation device 231 can be inserted through the third aperture 215 in the nail 201, similar to the technique described above with respect to FIG. 3E. Referring to FIG. 8C, the second fixation device 205 is inserted through the second aperture 211 in the nail 201 and through the slot 219 in the first fixation device 203.

As noted, these intersecting first and second fixation devices 203, 205 provide additional purchase in the head and neck region of the femur 229, and in particular the second fixation device 205 can provide bony fixation in the calcar. Accordingly, the interlocking first and second fixation devices 203, 205 can provide for improved stability and protection against common modes of intramedullary nail implant failure.

Figure 9A:
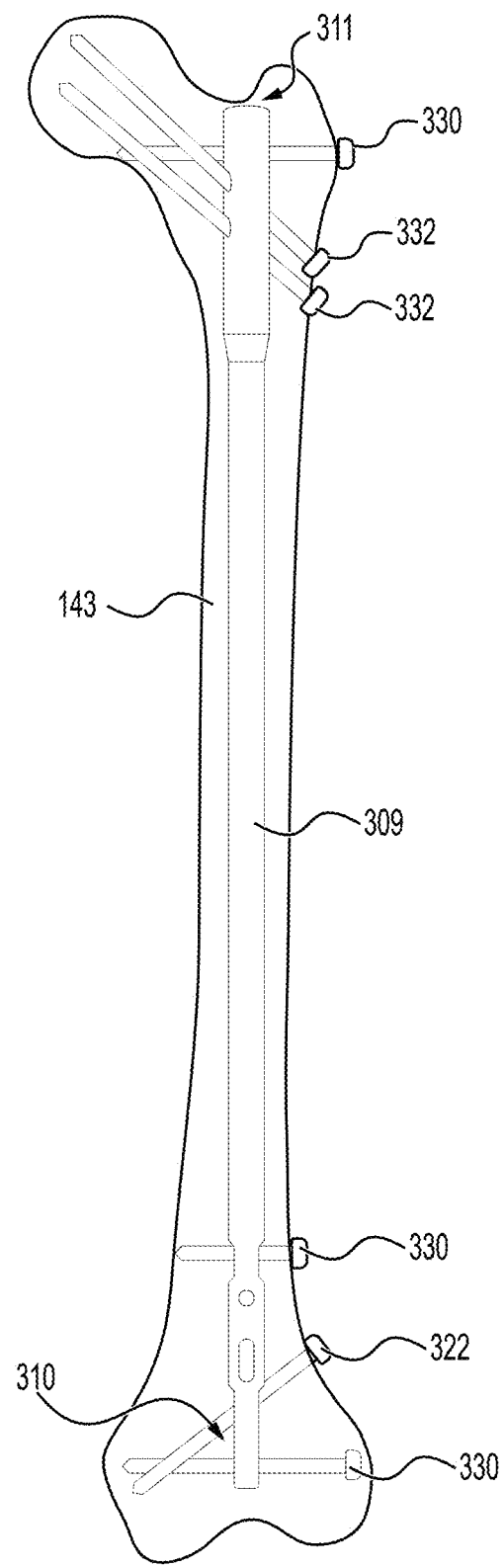
FIGS. 9A-9N illustrate various views of an illustrative intramedullary nail.
Figure 9B:
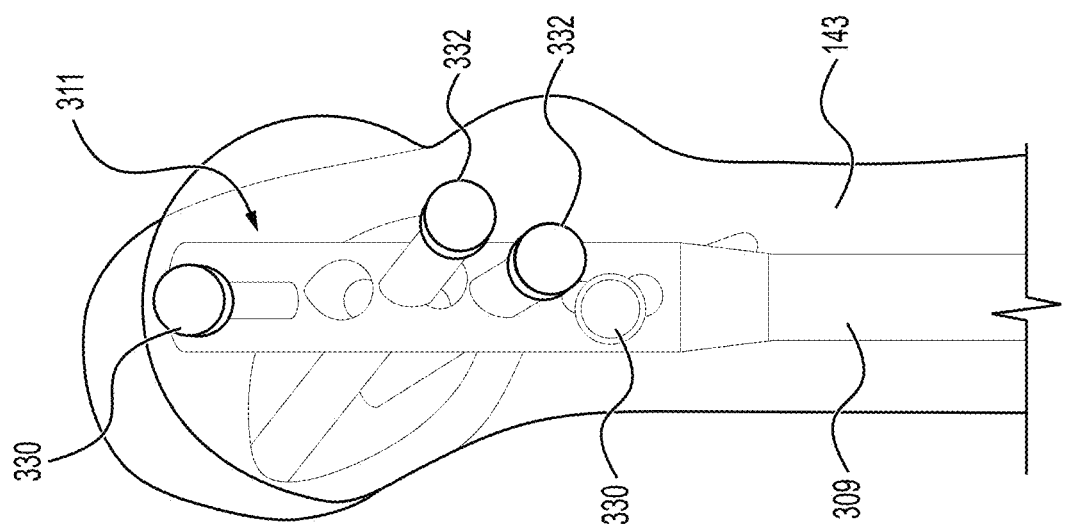
Figure 9D:
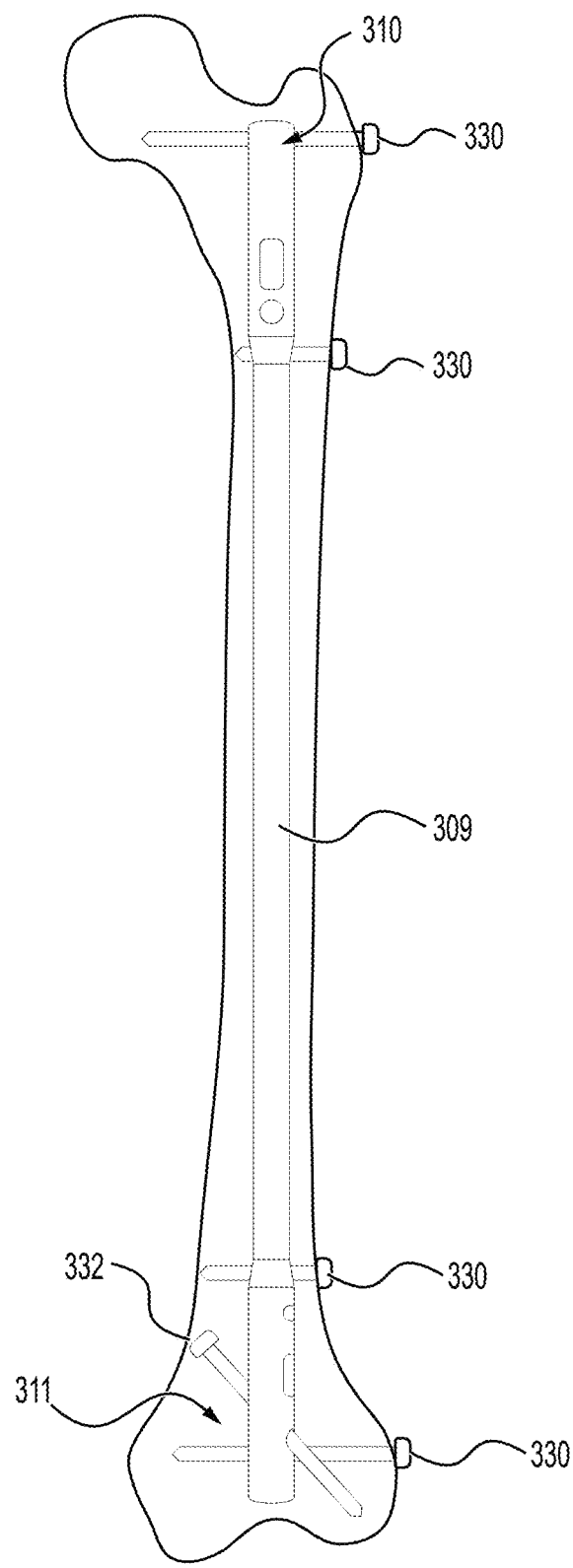
Figure 9J:
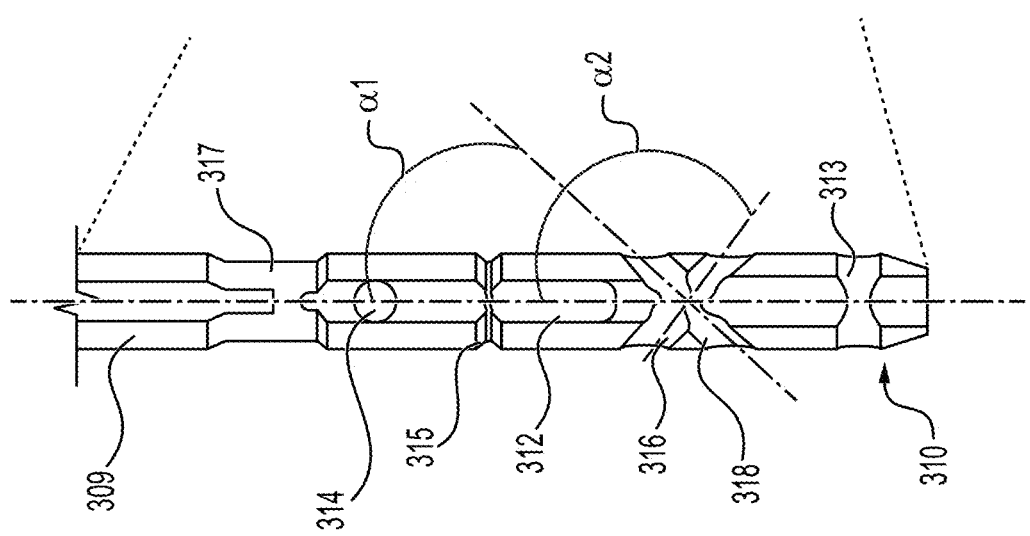
Figure 9K:
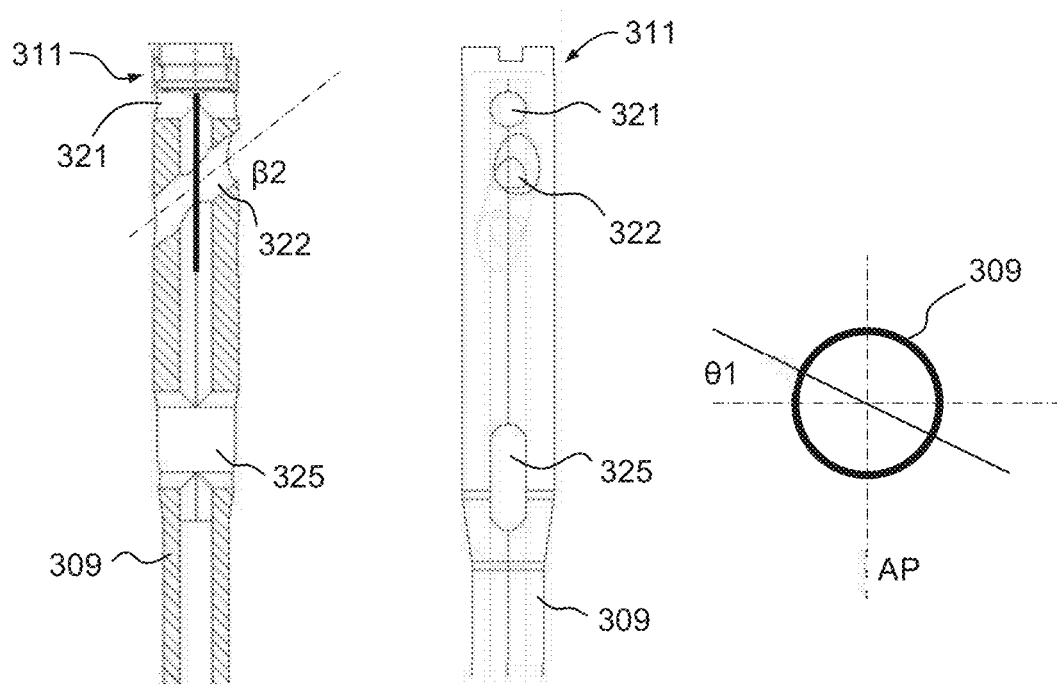
Figure 9L:
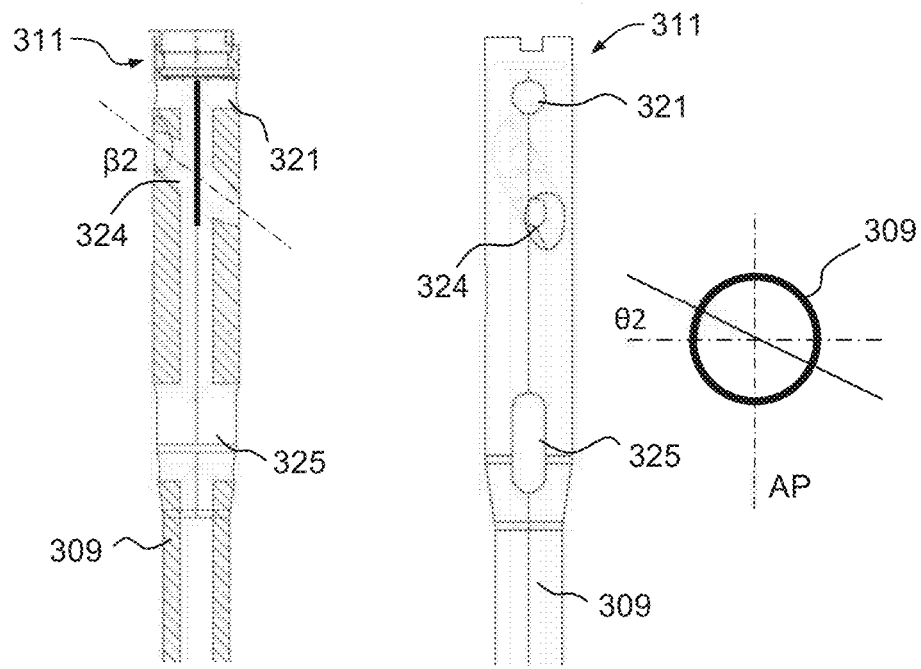
Figure 9M:
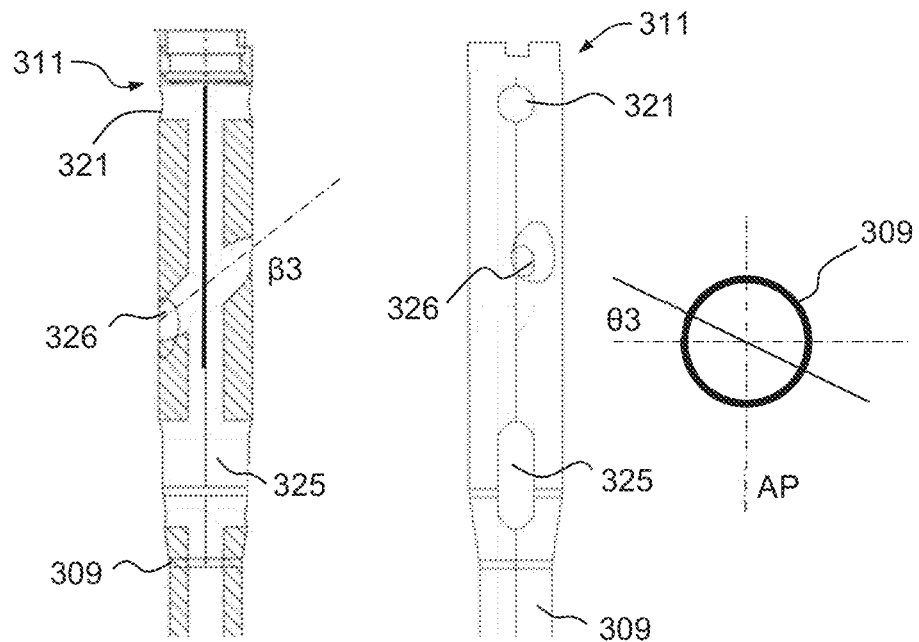
Figure 9N:
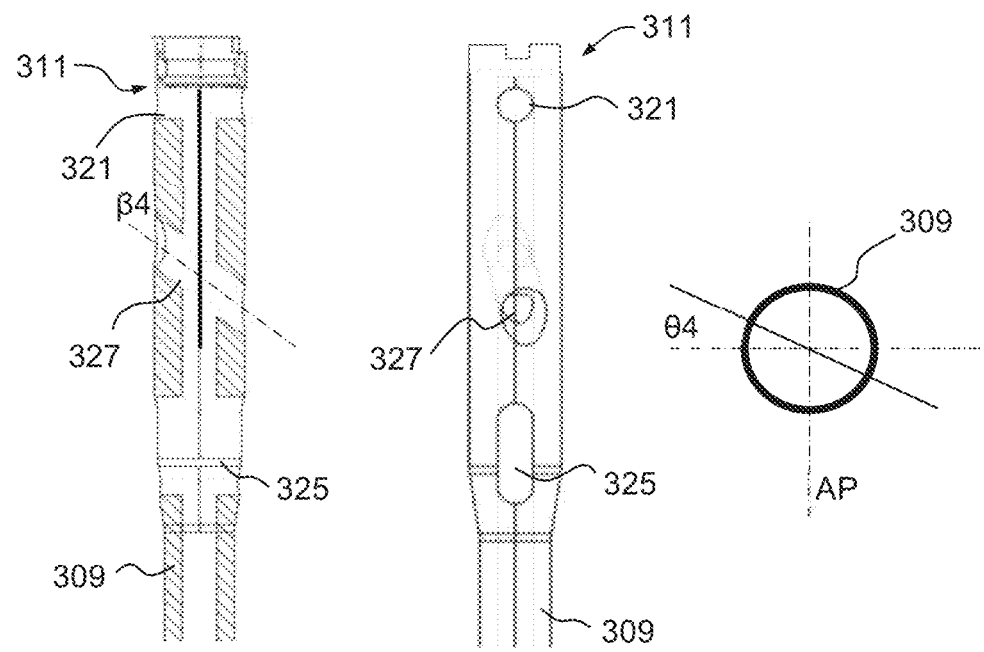

FIGS. 9A-9N illustrate another example of an intramedullary nail 309, which may comprise a generally elongate body extending from a first, distal portion or end 310 to a second, proximal portion or end 311. The elongate body may be in the form of an elongate tubular rod configured to extend longitudinally within the intramedullary canal of a fractured bone. The elongate rod may be hollow or may be solid along its length. The elongate body may be substantially straight along a longitudinal axis of the nail 309 or may comprise one or more curves or bends to conform to the anatomical shape of the intramedullary canal. In the embodiment of the nail 309 illustrated in FIG. 9A, the nail 309 may be utilized in a piriformis fossa entry and the curvature may be provided in the AP (anteroposterior) direction. This curvature allows the nail 309 to be used either antegrade (FIG. 9A) or retrograde (FIG. 9D), as well as in the right leg or left leg. In the embodiment illustrated in FIG. 9C, the nail 309' has curvature in the AP direction as well as a bend in the ML (medial-lateral) direction to facilitate entry at the tip of the greater trochanter. In other aspects, the nails 309 and 309' are the same unless otherwise described. The cross-section of the nail 309, taken at a right angle to a central longitudinal axis of the intramedullary nail 309, may be circular, oval, elliptical, or of any other suitable cross-dimensional shape.

Figure 10A:
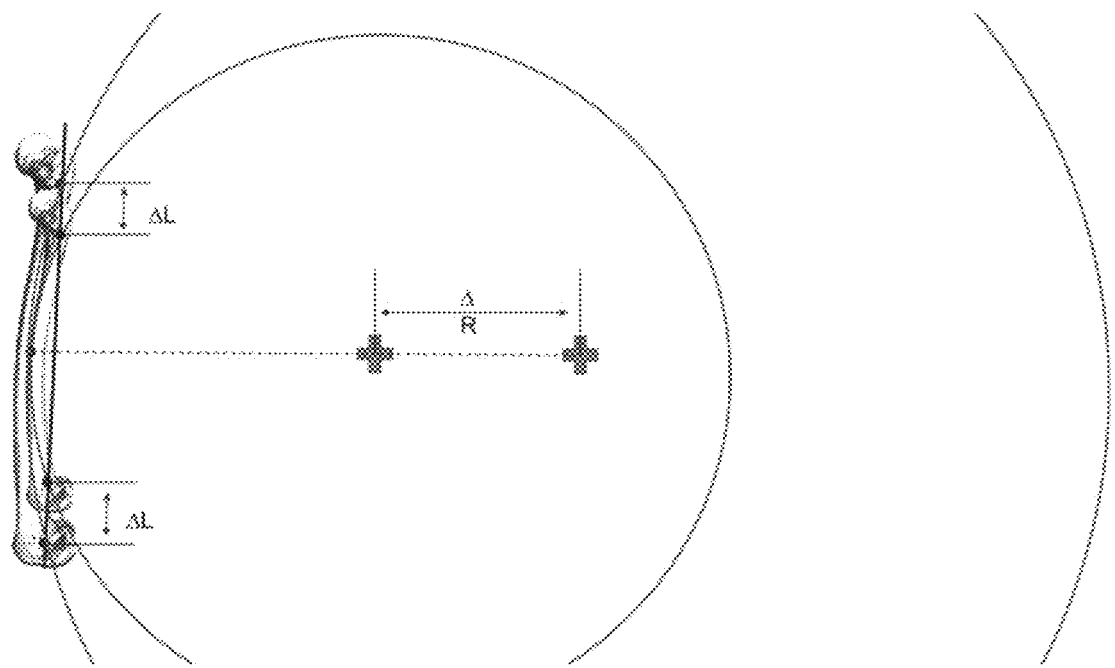
FIGS. 10A-10C illustrate steps of a method of calculating the radius of curvature of a femoral nail.
Figure 10B:
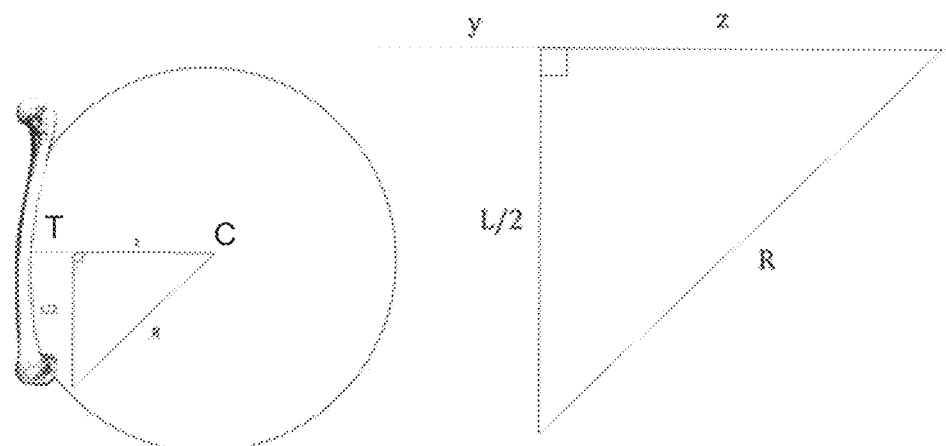
Figure 10C:
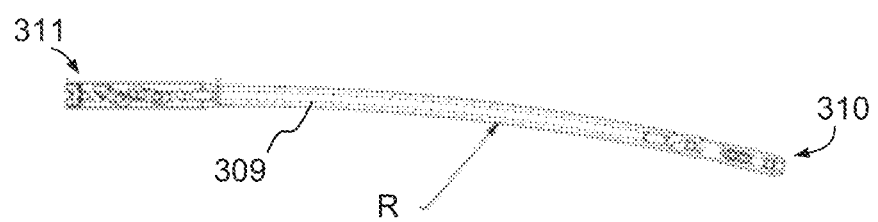

Referring to FIGS. 10A-10C, a process of calculating the AP curvature of the nail 309 will be described. The radius of curvature of the nail 309 may change depending on the length of the nail 309 so that the curvature can match the anatomical curvature of the femur into which the nail 309 is being inserted. Often-times, in longer femurs (taller patients), the curvature has too small a radius, and surgeons struggle to insert the nail without causing bone damage. The method of radius planning based on displacement described herein reduces the likelihood of a problem by offering a more anatomically correct (larger) radius.

As shown in FIG. 10A, the femur endpoints may be in a vertical line. As such, the AP radius of curvature can be calculated using tangent circles if a valid starting point is assumed, for example, a nail length L of mm having a radius R. Turning to FIG. 10B, each tangent circle will have a radius R. Drawing a right triangle from the center C of the tangent circle, with R as the hypotenuse and ½ the nail length L as one leg of the triangle, the other leg will have a length z. Due to the curvature, the point where the legs ½L and z meet will be spaced a distance y from the tangent point T. As such, $R=y+z$ and $R^2=L^2/4+z^2$. Combining the formulas results in $R=y/2+L^2/8y$. Utilizing the initial assumption, the constant y can be calculated. With the constant y calculated, the radius R of curvature for each length L can be found. Utilizing the assumption of a nail length having a radius R, the following is a table of calculated radius R for various lengths L.

| Nail Length (mm) | AP Bow (m) |
|---|---|
| 160-300 | 1.0 |
| 310-400 | 1.2 |
| 410-500 | 1.4 |

Referring again to FIGS. 9A-9N, the distal end 310 of the nail 309 may include one or more distal openings 312-318 configured to receive one or more bone anchors, fasteners, or distal fixation devices 330, 332 that extend transversely through the distal end 310 of the intramedullary nail 309, and are thereby configured to secure the distal end 310 of the nail 309 within the canal. The distal fixation devices 330, 332 may include a bone screw or anchor configured for distal locking of the nail 309 and also reconstruction. The distal fixation device 330, 332 may include traditional polyaxial or fixed angle locking bone screws and anchors known in the art.

In the illustrated embodiment, the distal openings include an AP locking slot 312 and an AP locking opening 314. The openings also include a pair of ML locking openings 313, 315 and an ML locking slot 317. The AP and ML locking slots 312, 317 facilitate relative movement between the nail 309 and the locking screw 330 in the event compression or the like is applied during installation. The distal openings also include a pair of oblique openings 316, 318 configured to receive and guide reconstruction screws 332. As illustrated in FIG. 9J, each of the oblique openings 316, 318 is at an angle $\alpha_1$, $\alpha_2$ relative to the axis of the nail 309. The angles $\alpha_1$, $\alpha_2$ are in the range of 45°-60°, and in the illustrated embodiment, are each 50°. It is preferred that the angles $\alpha_1$, $\alpha_2$ are equal to one another such that the oblique openings 316, 318 are mirror images of one another, thereby allowing the nail 309 to be utilized in both right and left legs. The distal oblique openings 316, 318 all surgeons to lock distal screws at an angle or approach a distal fragment from a more proximal screw entry point. This configuration could be useful for treatment of periarticular fractures and condylar splits. Additionally, the oblique distal openings 316, 318 allow surgeons to access condylar fractures without risking soft tissue damage near the knee or hip joint upon entry.

The proximal end 311 includes one or more proximal openings 123 configured to receive one or more bone anchors or fasteners 330, 332 that extend transversely through the proximal end 311 of the intramedullary nail 309, and are thereby configured to secure the proximal end 311 of the nail 309 within the canal and also reconstruction. The proximal fixation devices 330, 332 may include a bone screw or anchor. The fixation device 330 may be a locking screw and the fixation device 332 may be a calcar screw or anchor configured to be aimed at a calcar region of the proximal humerus, which may constitute the best quality bone in the region.

The proximal openings may include a pair of ML openings 321, 323 and an ML slot 325. The ML openings 321, 323 and the ML slot 325 are configured to receive the locking screws 330. The ML locking slot 325 facilitates relative movement between the nail 309 and the locking screw 330 in the event compression or the like is applied during installation. The distal openings also include a plurality of oblique openings 322, 324, 326 and 327, which preferably include mirrored pairs. More specifically, with reference to FIGS. 9K-9N, upper oblique openings 322 and 324 are mirror images, forming complementary angles $\beta_1$, $\beta_2$, i.e. $\beta_1+\beta_2=180°$. For example, the oblique angle $\beta_1$ may be about 100-150°, 110-140°, or about 120-135° relative to the nail 309 while the angle $\beta_2$ is about 30-80°, 40-70° or 45-60°. Similarly, the lower oblique openings 326, 327 are mirror images, forming complementary angles $\beta_3$, $\beta_4$, i.e. $\beta_3+\beta_4=180°$, which may extend over ranges similar to those given above for openings 322, 324. With such a configuration, the proximal oblique openings 322, 324, 326 and 327 are also aligned so that they will function the same in either the right or left leg. In the illustrated embodiment, the angles $\beta 1_1$, $\beta_3$ are equal and the angles $\beta 1_2$, $\beta_4$ are equal, however, such is not required.

Additionally, the openings whose axes are mirror images of one another are also offset in the AP plane from the sagittal plane, one by an $\theta_1$ the anterior and the other by an angle $\theta_2$ in the anterior. As illustrated in FIGS. 9K and 9L, the opening 322 is offset by $\theta_1$ while the opening 324 is offset $\theta_2$. Similarly, as illustrated in FIGS. 9M and 9N, the opening 326 is offset by $\theta_3$ while the opening 327 is offset $\theta_4$. In the illustrated embodiment, the larger offset $\theta_2$, $\theta_4$ is twice as large as the corresponding offset $\theta_2$, $\theta_4$. This creates room for the screw 330 to pass posteriorly to these two reconstruction screws 332 to make a fixed angle construct. In the illustrated embodiment, the offset $\theta_1$ of opening 322 is equal to the offset $\theta_4$ of opening 327 while the offset $\theta_2$ of opening 324 is equal to the offset $\theta_3$ of opening 326. With this configuration, the offsets of the similarly angled pair of openings 322 and 326 will be offset with respect to one another and the offsets of the similarly angled pair of openings 324 and 327 will be offset with respect to one another.

The nail 309 provides a hybrid antegrade/retrograde and left/right nail. Such a nail 309 is advantageous to hospitals and surgeons because it reduces stock and simplifies surgical planning. The bi-directional proximal oblique openings 322, 324, 326, 327 provide a variety of options for proximal femur fracture fixation, as well as a more stable construct. Additionally, the arrangement of the proximal openings 321-327 allows for a fixed-angle construct created by the screws 330, 332. The design further provides for three screws to be secured into the femoral neck. This fixed-angle construct provides more biomechanical stability than the traditional two screw configurations.

Referring to FIGS. 9I and 11A-11E, a method of attaching the intramedullary nail 309 with an insertion tool 350 will be described. The nail 309 of the present embodiment has an opening 334 at the proximal end 311. A shoulder 335 within the opening 334 defines a circumferential slot 336 on the inside diameter of the proximal portion 311 of the nail 309. This configuration takes up less space at the proximal end 311 of the nail 309 than a typical threaded connection, thereby freeing up space for more proximally located locking holes.

Figure 11A:
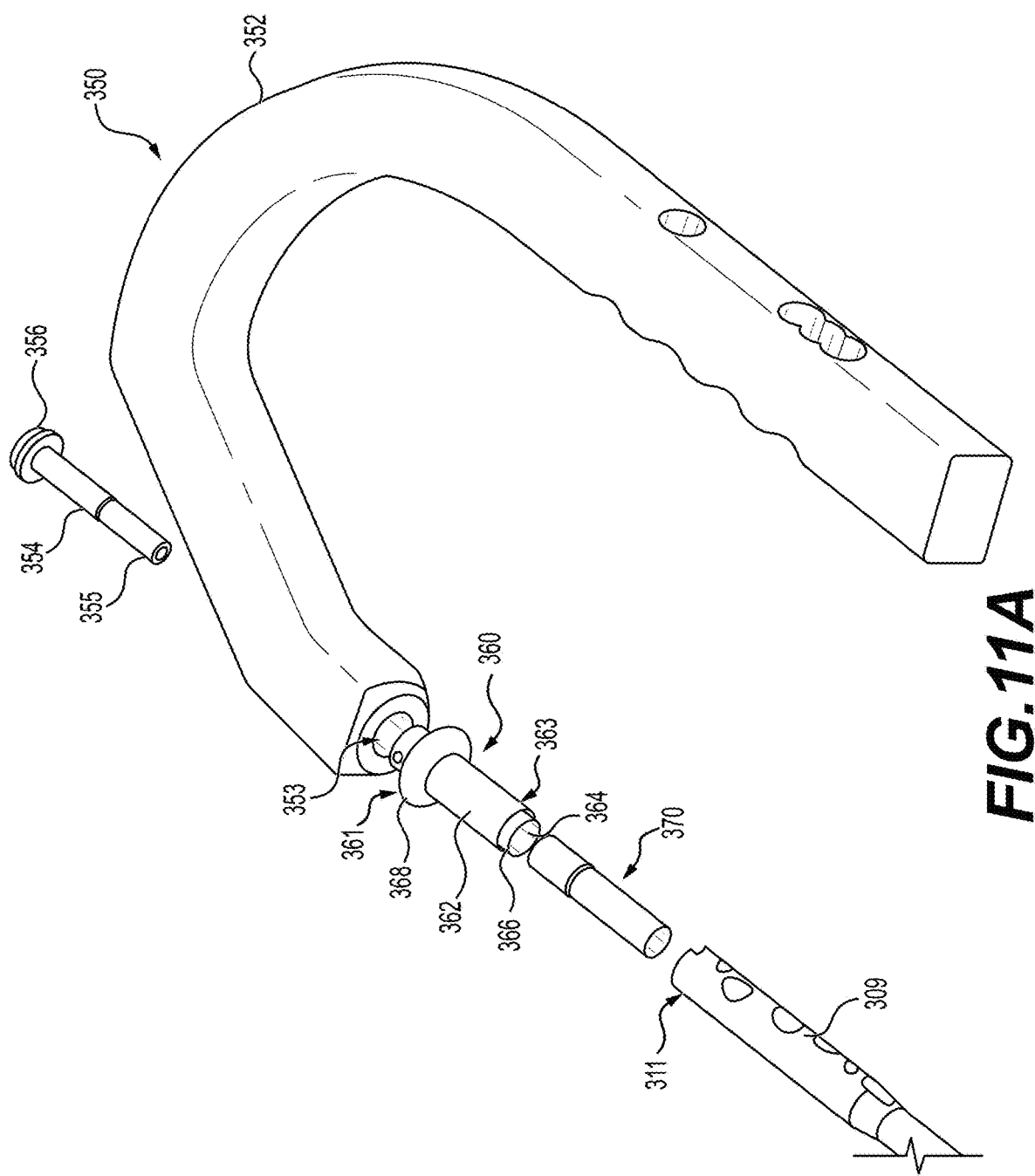
FIGS. 11A-11E illustrate various views of an insertion tool and intramedullary nail connection assembly.
Figure 11B:
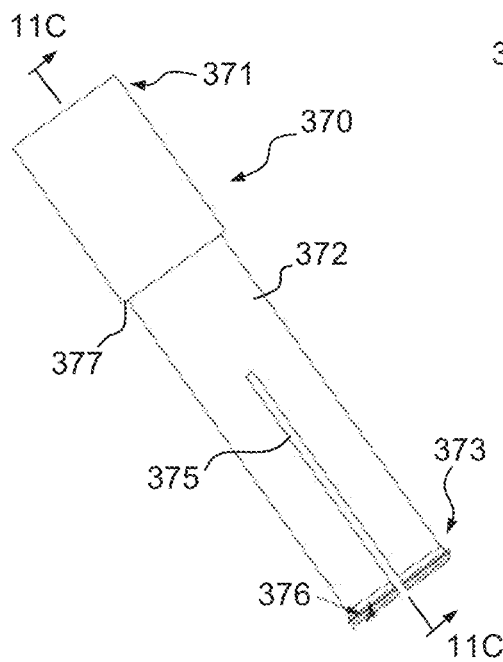
Figure 11C:
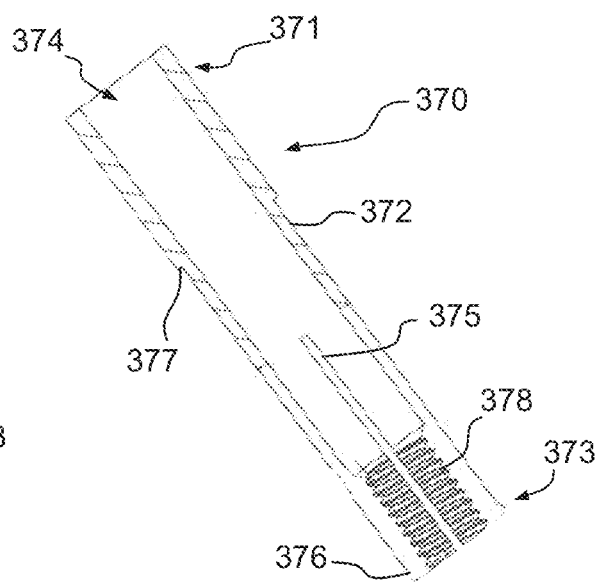
Figure 11D:
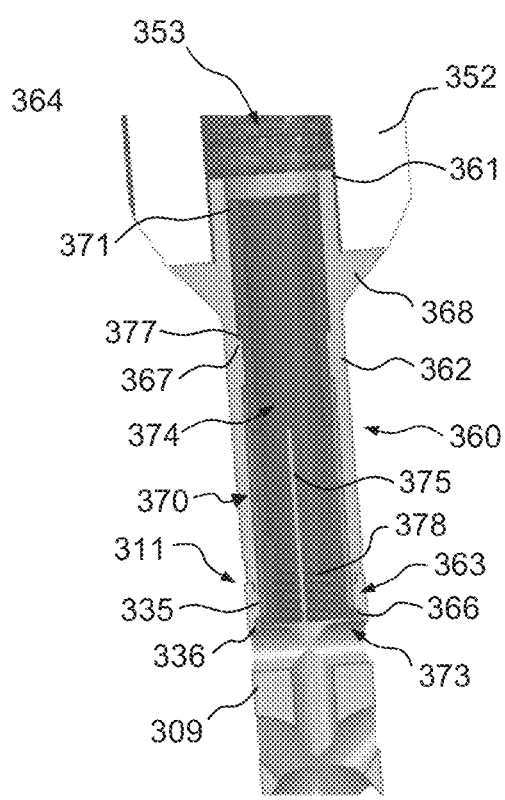
Figure 11E:
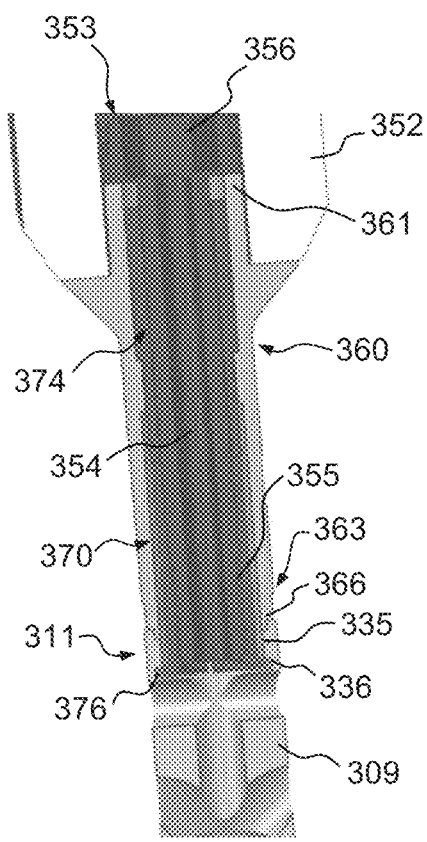
Figure 12A:
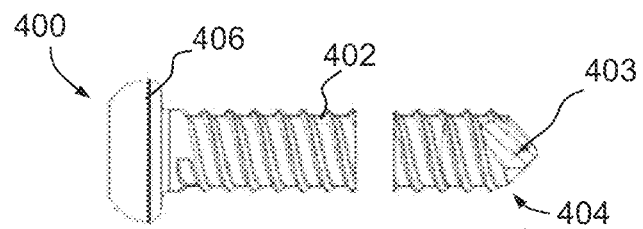
FIGS. 12A-12K illustrate various views of a locking screw and corresponding torque driver head.
Figure 12B:
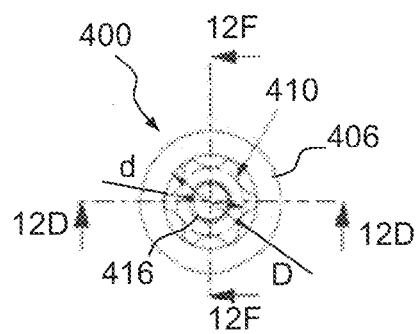
Figure 12C:
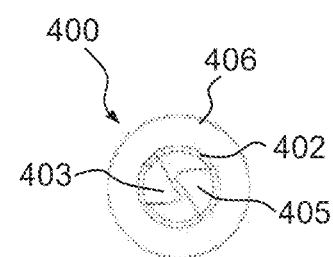
Figure 12D:
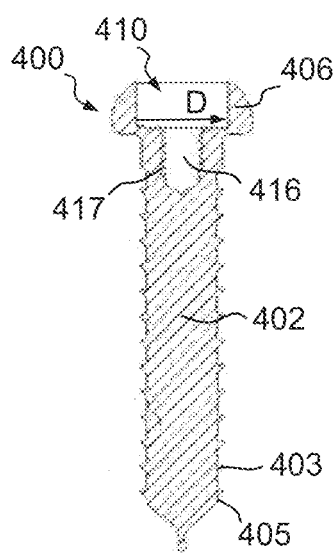
Figures 12E, 12F:
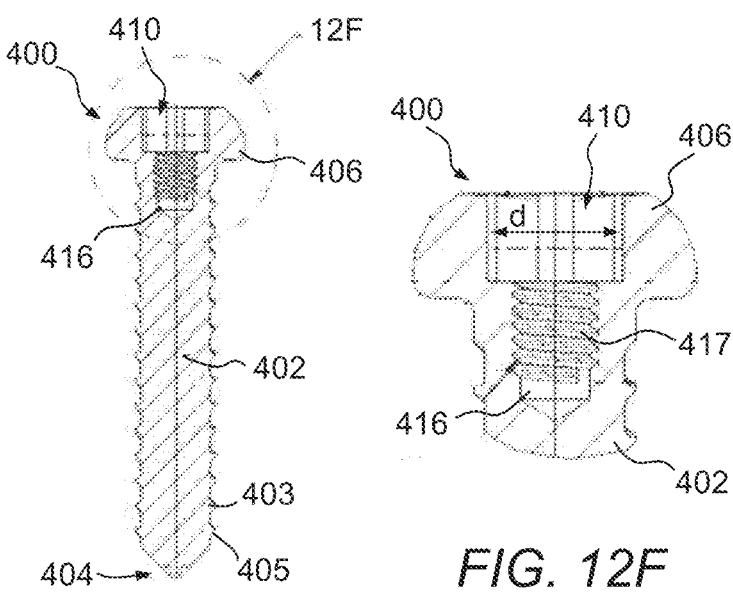
Figure 12G:
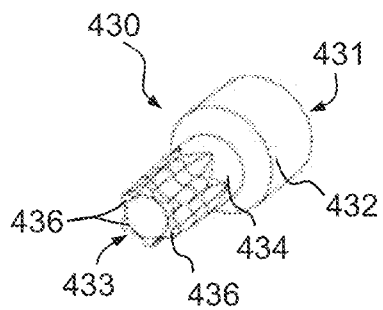
Figure 12H:
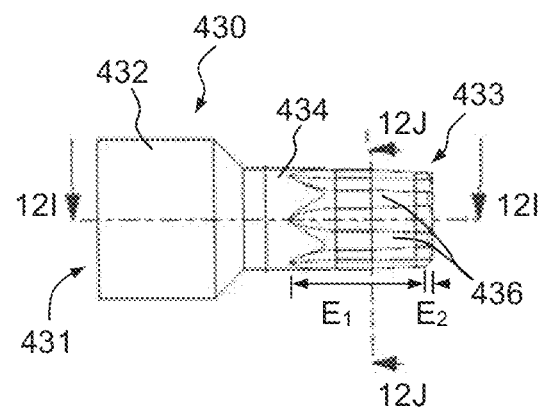
Figure 12I:
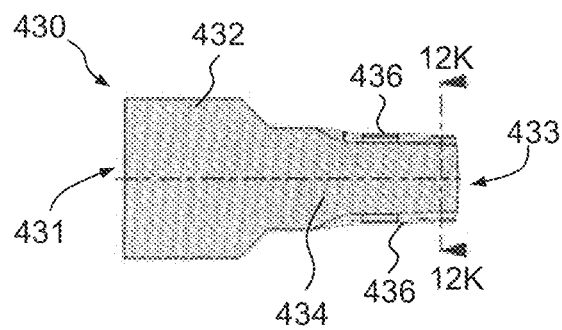
Figure 12J:
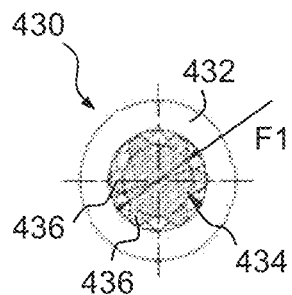
Figure 12K:
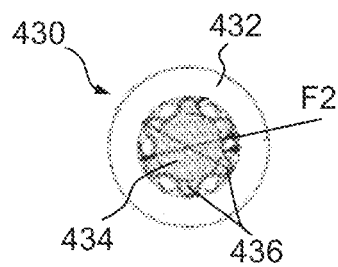

To connect the nail 309 to the insertion tool 350, the insertion tool 350 includes an expanding collet 370 and connecting bolt 354. An alignment tip 360, which connects within a through passage 353 in the aiming arm 352 of the insertion tool 350, is configured to align the bolt 354 with the expanding collet 370. The alignment tip 360 includes a hollow body 362 with a through passage 364 extending from a proximal end 361 to a distal end 363 of the body 362. The proximal end 361 of the body 362 is configured to be received into the through passage 353 of the aiming arm 352 with a press fit, however, other connecting mechanisms may be utilized. A shoulder 368 extends radially from the body 362 and engages the aiming arm 352 when fully inserted, as illustrated in FIGS. 11D and 11E. The distal end 363 of the body 362 has a recessed portion 366 configured to be received into the opening 334 in the proximal end of the nail 309.

The expanding collet 370 includes a hollow body 372 with a through passage 374 extending from a proximal end 371 to a distal end 373 of the body 372. The distal end 373 has a radially outwardly extending collar 376, tabs, projections or the like. The collar 376 is configured to be received within the circumferential slot 336 in the proximal end 311 of the nail 309. Axial slots 375 extend from the distal end 373 of the body 372 and allow the distal end of the body 372 to compress radially inwardly, thereby allowing the collar 376 to pass through the alignment tip through passage 364 and the shoulder 335 within the proximal end 311 of the nail 309. An external shoulder 377 on the collet 370 contacts an internal shoulder 367 on the alignment tip 360 to limit the range of motion of the collet 370 relative to the alignment tip 360. Once the collar 376 is past the shoulder 335, the collar 376 is free to expand radially outwardly. The distal end 373 of the collet body 372 includes internal threads 378 configured for engagement with the threads 355 of the connecting bolt 354.

The connecting bolt 354 then drives through the through passage 374 of the expandable collet 370 and engages the threads 378. As the connecting bolt 354 is threaded with the threads 378, it pushes the collar 376 outwardly to its major diameter and further drives the collar 376 into the circumferential slot 336 within the nail 309. In addition, when the bottom side of the head 356 of the bolt 354 makes contact with the top of the alignment tip 360, it allows for compression across the proximal nail 309, thus compressing any spacing in the connection. The assembly allows for quick, easy, and rigid connection of the nail 309 to the aiming arm 352. It is noted that any of the intramedullary nails described herein may include an internal circumferential slot and be connected to an insertion tool or the like utilizing an expanding collet as described.

Referring to FIGS. 12A-12K, a self-retaining screw 400 and driver 430 assembly will be described. Screws are often affixed to drivers on the back table by a scrub tech or nurse and then they are handed to the surgeon who places the screw where it is needed. Between the back table, and the final seating of the screw into the bone, many actions can dislodge it from the driver, thus rendering it non-sterile, for example, when it hits the operating room floor. To minimize the likelihood of dislodging, the self-retaining nail locking screw 400 has features which achieve a more secure connection.

With reference to FIGS. 12A-12F, the screw 400 includes a shaft 402 extending from a distal tip 404 to a proximal head 406. In the illustrated embodiment, the shaft 402 includes a two thread 403, 405 start which provides for easier advancement. The head 406 defines a proximal torque bore 410 and a threaded bore 416 distally thereof. The torque bore 410 and the threaded bore 416 are in communication with one another and preferably coaxial. The torque bore 410 has a configuration with engaging surfaces to engage a complimentary torque tool. In the illustrated embodiment, the torque bore 410 has a hexalobe configuration with a plurality of lobal recesses 412 extending radially from the central opening. The lobal recesses 412 define a maximum diameter D while the central opening defines a smaller diameter d. The lobal recesses 412 are configured to receive complementary lobes 436 on a driving tool head 430, as will be described in more detail below. The threaded bore 416 defines a plurality of internal threads 417 which are configured to be engaged by a threaded rod (not shown) which tightens into the threaded bore 416 at the bottom of the torque bore 410. The combination of a torque bore 410 and a threaded bore 416 allows for secure delivery of the screw 400 utilizing the threaded rod and thereafter additional tightening of the screw 400, if needed, utilizing a torque driver engaged with the torque bore 410.

Referring to FIGS. 12G-12K, the torque driver head 430 illustrated therein has a taper in order to give it a stab and grab retaining feature on its own. The torque driver head 430 includes a proximal body 432 and a distal shaft 434 extending therefrom. The proximal body 432 and shaft 434 are preferably a unitary structure extending from a proximal end 431 to a distal end 433. A plurality of lobes 436 extend radially from the shaft 434 and have a complementary configuration to the lobal recesses 412 in the torque bore 410 of the screw 400. The lobes 436 taper, narrowing moving in the distal direction. The taper is generally constant over a first length $E_1$ and then more pronounced at the distal end 433 over the length $E_2$. With the taper, the lobes 436 define a larger maximum diameter $F_1$ in the proximate portion of the shaft 434 (see FIG. 12J) and a smaller maximum diameter $F_2$ in the distal portion of the shaft 343 (see FIG. 12K). The larger diameter $F_1$ is preferably larger than the maximum diameter D of the lobal recesses 412 and the smaller diameter $F_2$ is preferably smaller than the maximum diameter D of the lobal recesses 412, i.e. $F_1 > D > F_2$. With this configuration, the distal end 433 of the torque driver head 430 moves easily into the torque bore 410, however, as the torque driver head 430 is inserted further, the lobes 436 engage the lobe recesses 412 in a friction fit, providing the stab and grab retaining feature. In some instances, this feature may provide sufficient secure connection without the need to utilize the threaded rod and threaded bore 416.

Referring to FIGS. 13A-13F, a headless version of the screw 400' will be described. There are several scenarios in which a surgeon may desire to have as low of a head profile on a screw as possible. For example, when a fracture occurs near the joint space, it is often necessary for a surgeon to place screws through the articular surface. In order to preserve function of the joint, and avoid joint pain, it is essential that the locking screw used does not impinge any motion of the bones or soft tissues in that region. A headless screw may also be desired in areas where the soft tissue above the bone is very thin, so prominent screw heads may be felt or even seen by the patient post-op (e.g., in the proximal tibia).

The headless screw 400' is similar to the screw of the previous embodiment and includes a shaft 402 extending from a distal tip 404 to a proximal head 406'. In the illustrated embodiment, the shaft 402 includes a two thread 403, 405 start which provides for easier advancement. Although it will be appreciated that the screw 400' may have a single thread start or any other suitable configuration. Similar to the previous embodiment, the head 406' defines a proximal torque bore 410 and a threaded bore 416 distally thereof. The torque bore 410 has a configuration with engaging surfaces to engage a complimentary torque tool and the threaded bore 416 defines a plurality of internal threads 417.

The head 406' of the present embodiment, has a plurality of external threads 407. In the illustrated embodiment, the threads 407 may have a four start thread that is half the pitch of the shaft thread. The threads 407 allow the head 406' to be sunk beneath the surface of the bone. When used in conjunction with the intramedullary nails described herein or otherwise known, the headless screw 400' provides a unique offering of a headless option that still acts the same as a standard locking screw.

According to an exemplary embodiment, an intramedullary nail system includes an intramedullary nail in combination with at least one headless screw or fastener. The intramedullary nail may include intramedullary nails 109, 201, 309, 500 described herein or any other intramedullary nails generally known or hereinafter developed. The headless screw or fastener is intended to encompass a screw or fastener, which is blind such that the screw is fully threaded and has no head projecting past a major diameter of the screw thread and/or may encompass a screw or fastener having a head portion where the thread extends all the way to the head (e.g., a threaded head). For example, the headless screw may include headless screw 400' described herein or any other headless screw generally known or hereinafter developed.

According to one embodiment, the intramedullary nail 109, 201, 309, 500 is used in combination with at least one headless screw 400' or headless fastener. The headless screw 400' or other headless fastener may be positioned through the body of the nail 109, 201, 309, 500 such that the shaft 402 resides within one or more openings in the nail 109, 201, 309, 500. The shaft 402 of the headless screw 400' may be configured to mate with the intramedullary nail 109, 201, 309, 500 in a locking (e.g., threaded mating) or non-locking fashion. The threaded head 406' of the headless screw 400' may be positioned such that the head 406' is positioned at or near the outer surface of the bone, for example, as best seen in FIG. 9A. By positioning the head 406' of the headless screw 400' against the bone (or slightly inset into the bone) in combination with the intramedullary nail 109, 201, 309, 500, the intramedullary system may be substantially unnoticeable to a patient. When traditional headed screws are used, sometimes patients complain that they are able to feel the screw or the screw head protrudes from the surgical site causing irritation or pain to the patient. Accordingly, it may be suitable for one or more headless screws or fasteners to be used when securing the distal and/or proximal ends of the intramedullary nail, thereby resulting in superior patient outcomes.

Figure 14A:
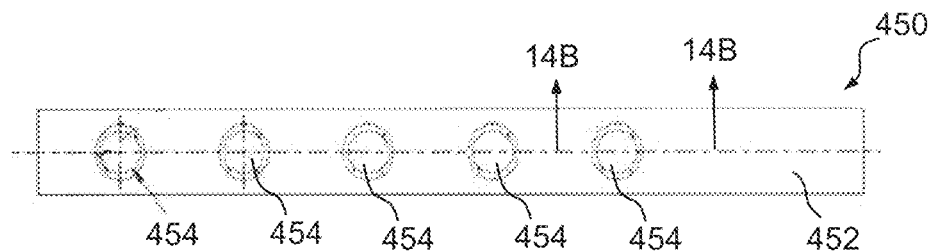
FIGS. 14A-14C illustrate various views of a nail including a locking screw opening with a 2 start thread configuration.
Figure 14B:
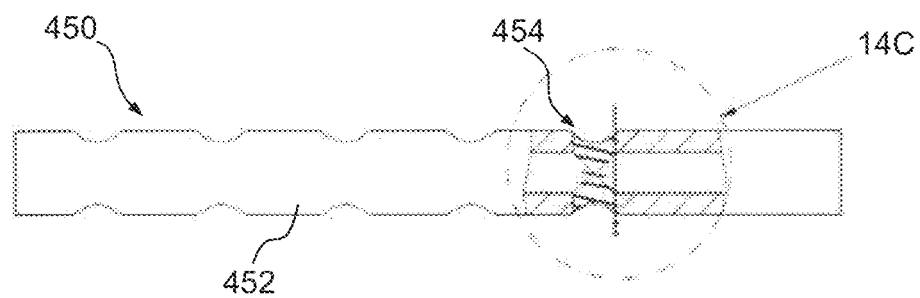
Figure 14C:
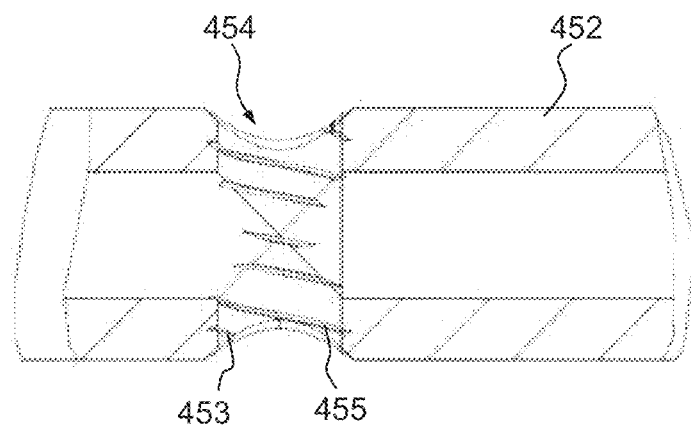

Referring to FIGS. 14A-14C, a nail 450 with a threaded hole 454 will be described. In unstable fractures or in patients with poor bone quality, it is imperative that the surgeon has an ability to stabilize the lateral translation of the nail relative to the screw. This is often referred to as an interference fit. To achieve interference fit with the screw 400 or a similar locking screw, the nail 450 is provided with one or more threaded holes 454 along the elongate body 452 of the nail 450. The threaded hole 454 includes threads 453, 455 with a two start thread. In the illustrated embodiment, the threads 453, 455 provide a two start 60-degree machine thread. The threads 453, 455 will have the same pitch as the threads 403, 405 of the screw 400. As previously described, the screw shaft 402 also has a two start thread for easy advancement. The threaded two start hole 454 in the nail 450 itself is an advantage over current interference holes because it is easy to manufacture, and requires no additional steps or special techniques on the part of the surgeon.

Figure 15A:
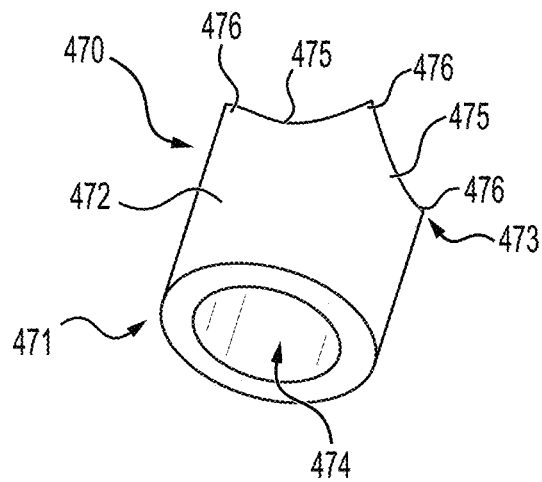
FIGS. 15A-15C illustrate various views of a screw compression washer.
Figure 15B:
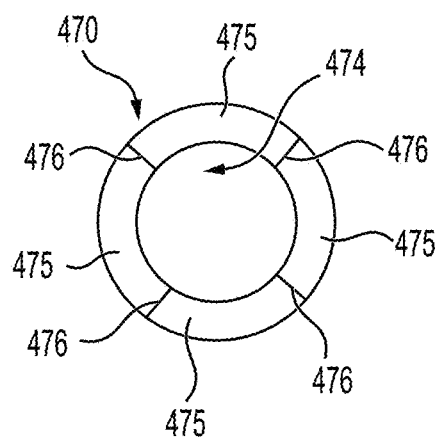
Figure 15C:
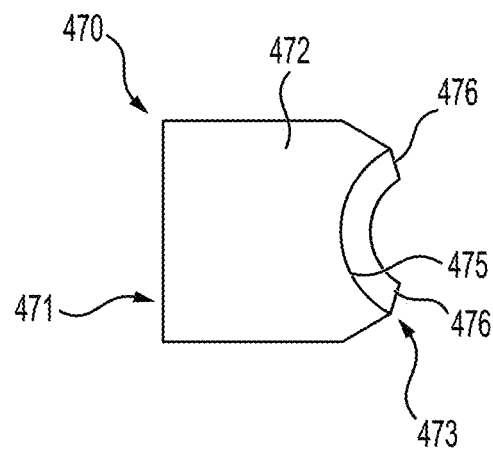

Referring to FIGS. 15A-15C, a washer 470 configured to provide greater compression on the screw will be described. In some applications, the screw and nail may not provide sufficient interference. For example, when poor bone quality or severely comminuted fractures interfere with screw placement, surgeons often require a screw which interfaces with the nail itself. When the near cortical wall is not stable, which is the case in a number of complex femur fractures, even an interference fit screw will not get any purchase in the near cortex, and therefore the fixation will be unstable. The washer 470 may be provided as an option for use with a screw and nail assembly if the conditions present the need for such.

The washer 470 includes a hollow body 472 with a through passage 474 extending from a proximal end 471 of the body 472 to a distal end 473 of the body 472. The distal end 473 of the body 472 includes a plurality of cutouts 475 between distal tips 476. Each cutout 475 is approximately 90° such that each pair of opposed cutouts 475 is coaxial thereby allowing an outer diameter of the nail. The washer 470 fits over the major diameter of the screw and sits flush with the underside of the head. It may be inserted through a tissue protection sleeve along with the screw and driver. When the distal tips 476 of the washer 470 come into contact with the outer diameter of the nail and the nail is received into the opposed cutouts 475, the screw continues to spin while the washer 470 grips the side of the nail. This allows the screw to get compression on the far side of the nail and hold the screw/washer construct firmly to the side of the nail. This provides a rigid fixation method when the cortical bone is not strong enough to do so. The washer 470 thereby expands the indications for which the nail can be used.

Having described illustrative femoral nails, embodiments of tibial nails and systems for implantation thereof will be described with reference to FIGS. 16A-17K. Referring to FIGS. 16A-16D, a first tibial intramedullary nail 500 will be described. It is recognized that the features of the nail 500 are not limited to use in a tibial nail and may be incorporated into other intramedullary nails. The intramedullary nail 500 generally comprises an elongate body 502 extending from a first, distal portion or end 503 to a second, proximal portion or end 501. The elongate body 502 may be in the form of an elongate tubular rod configured to extend longitudinally within the intramedullary canal of a fractured bone. The elongate rod may be hollow or may be solid along its length. The elongate body may be substantially straight along a longitudinal axis of the nail 500 or may comprise one or more curves or bends to conform to the anatomical shape of the intramedullary canal. In the embodiment of the nail 500 illustrated in FIGS. 16A-16D, the nail 500 is utilized in a tibia and the proximal end has a bend λ relative to the shaft has a bend while the distal end has a bend χ relative to the shaft. In the illustrated embodiment, the bend λ is approximately 10° while the distal end bend χ is approximately 3°. The bends λ and χ are not limited to the described angles and may have larger or smaller bends depending on the anatomy of the bone.

The distal end 503 of the tibial nail 500 contains four openings 510-513. The openings 510, 512 are oriented in the ML direction and the openings 511, 513 are oriented in the AP direction. In the illustrated embodiment, the ML opening 510 and the AP opening 511 each include a 2 start thread 514 used to create a fixed angle construct with the locking screw, similar to that described above with respect to FIG. 14C. Fixed angle constructs are used to treat highly unstable fractures.

Figure 16A:
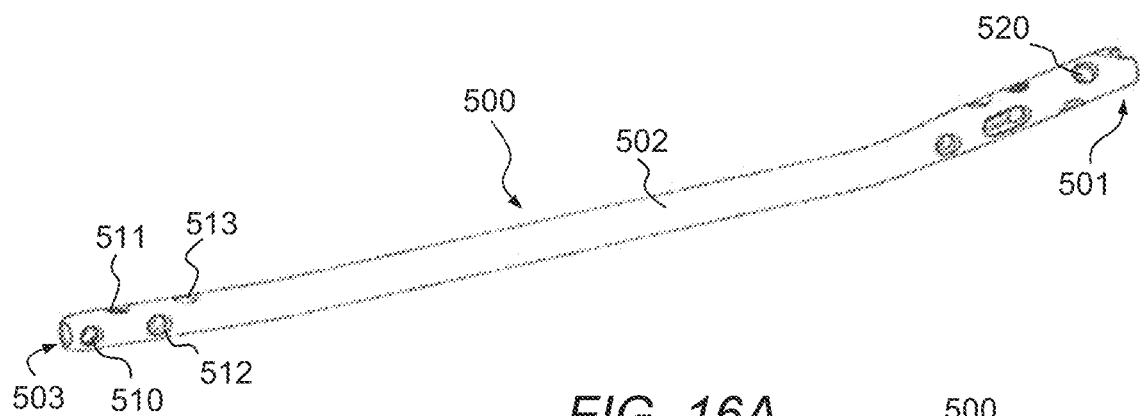
FIGS. 16A-16H illustrate various views of illustrative tibial nails.
Figure 16B:
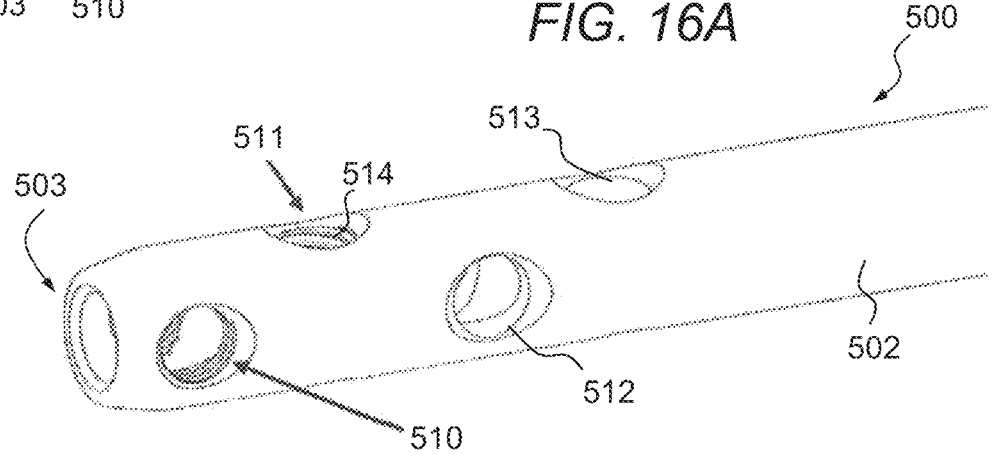
Figure 16C:
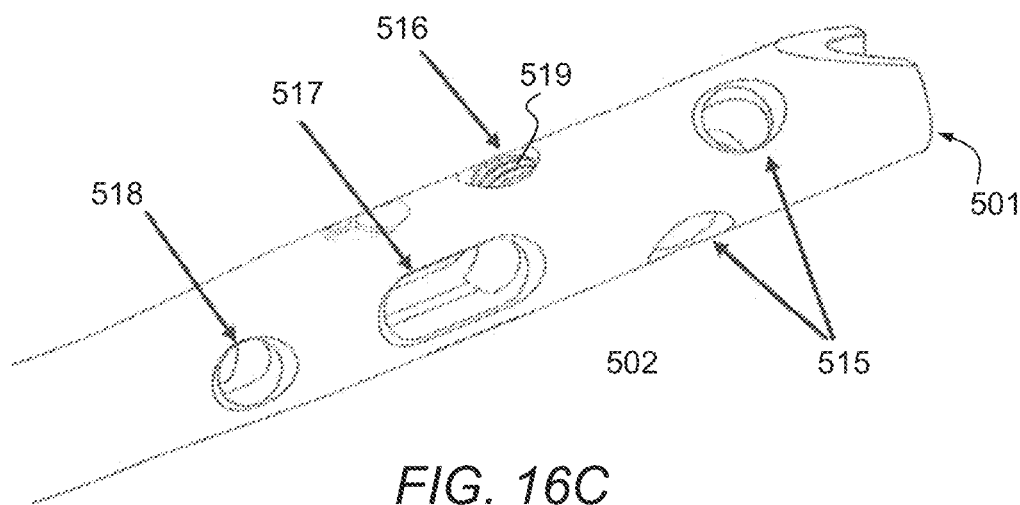
Figure 16D:
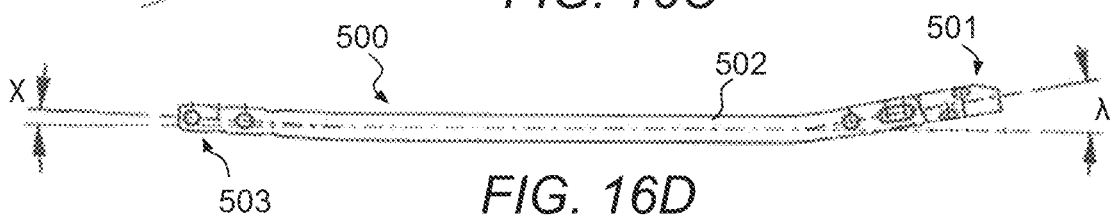
Figure 16E:
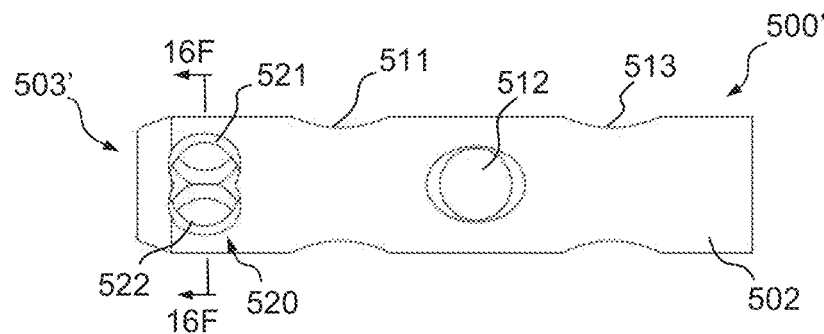
Figure 16F:
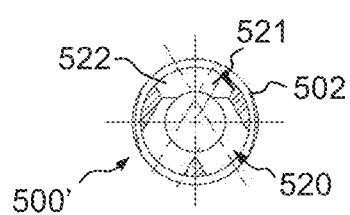
Figure 16G:
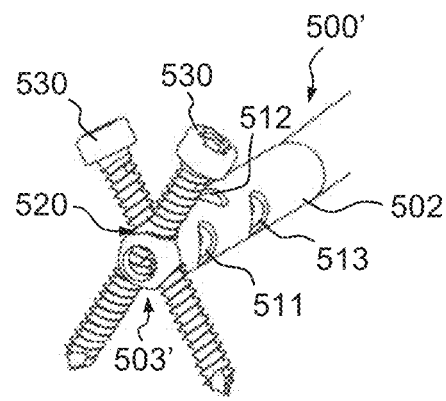

Referring to FIGS. 16E-16G, an alternative distal end 503' of the nail 500' will be described. In this embodiment, the ML opening 510 is replaced with a combined oblique locking opening 520, with first and second openings 521, 522 each at an oblique angle, for example, at 30° off the sagittal plane. The combined oblique locking opening 520 allows the surgeon to insert locking screws 530 in two different orientations, thereby creating an alternative fixed angle construct.

Figure 16H:
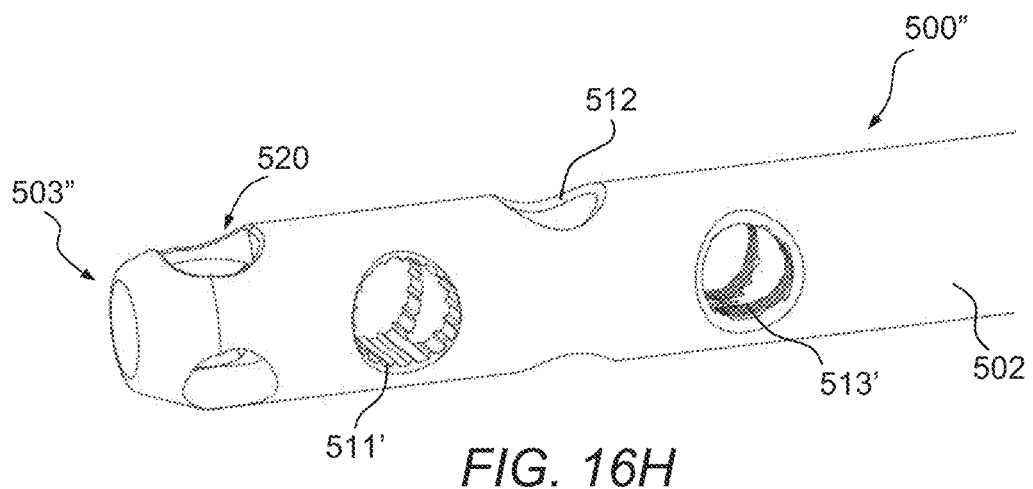

Referring to FIG. 16H, another alternative distal end 503" of the nail 500" illustrates additional features which may be utilized to create a fixed angle construct. In this embodiment, the AP opening 511' is defined as a broached hole while the AP opening 513' is defined as a threaded hole. The fixed angle construct is created by inserting a locking screw through the threaded or broached hole. The locking screw thread engages with the threads or broached features to stabilize the fracture by limiting the movement of the screw 530 relative to the nail 500".

Returning to FIGS. 16A and 16C, the proximal end 501 of the tibial nail 500 contains openings 515-518, including a pair of proximal oblique openings 515, an AP oblique opening 516, a proximal ML slot 517 and a proximal ML opening 517. The proximal oblique openings 515 are similar to those describe above with respect to the embodiment illustrated in FIG. 9A. The AP oblique opening 516 contains a 2 start thread 519 used to create a fixed angle construct with a locking screw. The proximal ML slot 517 is used for compression of fractures and static/dynamic locking modes.

Figure 17D:
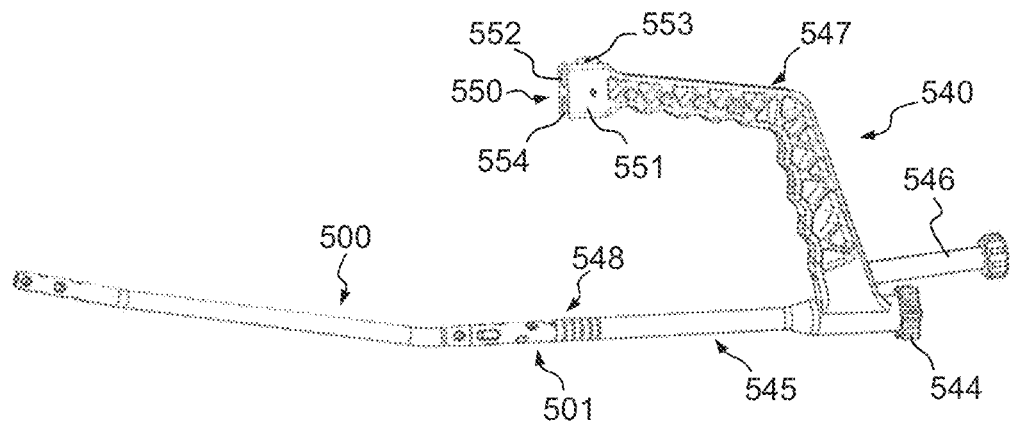
Figure 17E:
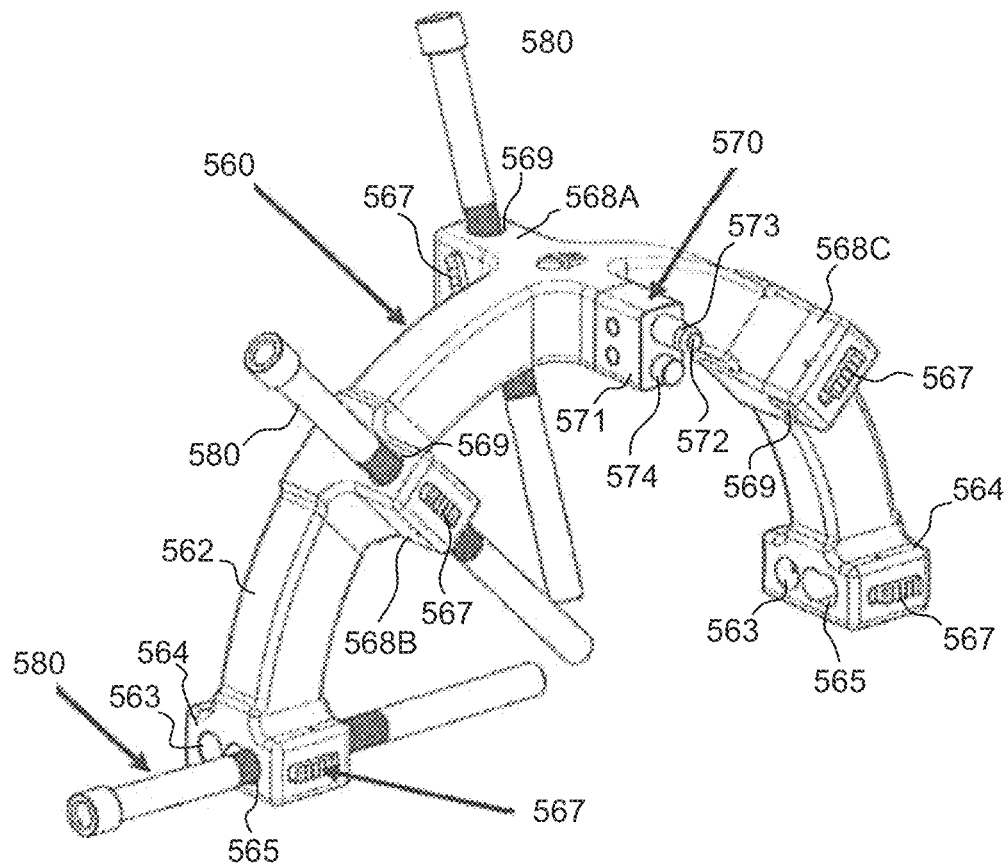

Having described various features of illustrative tibia nails 500, tools, systems and methods of inserting the tibia nails 500 will be described with reference to FIGS. 17A-17K. The tibial nail 500 is inserted into the medullary canal through an incision at the entry site. FIG. 17A illustrates an illustrative embodiment of a system 535 for implanting an intramedullary nail 500 utilizing the infra-patellar approach. The infra-patellar approach is the industry standard approach for insertion of the tibial nail 500. This approach is typically performed with the leg in the hyper-flexed (HF) position. The tibial nail 500 is inserted directly through the incision into the tibial canal.

The system 535 includes an insertion tool 540 and an aiming guide 560. The insertion tool 540 includes a coupling portion 545 and a handle portion 547. In some embodiments, the coupling portion 545 and the handle portion 547 can be separate parts that are removably joined together, while in other embodiments the coupling portion 545 and the handle portion 547 can be different regions of a single, integrally formed component. The handle portion 547 is preferably rigid, for example, made from stainless steel and also has provisions to attach an impaction shaft 546 and compression bolt 544. The coupling portion 545 has a connection portion 548 configured to releasably engage or couple to the proximal portion 501 of the nail 500. In the illustrated embodiment, the connection portion 548 includes a threaded connector. However, those skilled in the art will understand that other coupling mechanisms may be employed.

The handle portion 547 includes a connection assembly 550 for releasably attaching the handle portion 547 to the aiming guide 560. The connection assembly 550 includes a body 551 with two bores 552, 554 defined therein. A connection button 553 extends into one of the bores 552. The connection button 553 is biased to a connected position as illustrated in FIG. 17B. The connection button 553 has an engagement portion 556 within the bore 552 configured to engage a slot 573 on a connection post 572 of the aiming guide, as will be described in more detail hereinafter. In the illustrated embodiment, the engagement portion 556 includes a plate with a smaller diameter opening 557. To disengage the engagement portion 556, the button 553 is depressed such that the larger diameter opening 558 aligns with the connection post 572. However, those skilled in the art will understand that other connection mechanisms may be employed.

The tibial nail aiming guide 560 is used to install locking screws into the tibial nail 500. The aiming guide 560 sets the trajectory of the locking screws to interface with the proximal openings 515-518 of the nail 500. In at least one embodiment, the aiming guide 560 is made from a radiolucent material. The aiming guide 560 includes an arcuate body 562 which extends between opposed end support blocks 564. Each end support block 564 defines a hole opening 563, which aligns with the ML opening 518, and a slot opening 565, which aligns with the ML slot 517. A plurality of intermediate support blocks 568A-C extending from the body 562. The support block 568A includes a hole opening 569 which is aligned with the AP oblique opening 516. The support blocks 568B and 568C each include a hole opening 569 which is aligned with a respective oblique opening 515. The openings 563, 565, and 569 are configured to support respective guide sheaths 580 similar to the guide sheaths 117 described above. The sheaths 580 are used to protect the soft tissue during the drilling process. The sheaths 580 accept drill sleeves and trocars of various sizes. The guide sheaths 580 and blocks 564, 568A-C may have retention members similar to those described above, with each block 564, 568A-C having a respective release mechanism 567.

The aiming guide 560 also includes a connection assembly 570 configured to mate with the connection assembly 570 on the insertion handle 540. The connection assembly 570 includes a body 571 with a pair of connection posts 572, 574 extending therefrom which are configured to be received in the bores 552, 554 of the connection assembly 550. The connection post 572 includes a slot 573 configured to be selectively engaged by the engagement portion 556 of the connection button 553. The connector assembly 570 is a rigid structure and may be made from, for example, metal.

Accordingly, the system 535 provides an insertion handle 547 with reliable and convenient connection assembly for attaching the aiming guide 560. A push button connection and release system allows tool free connection and disconnection of the aiming guide 560. The insertion handle 547 also contain an external compression bolt 544 used to apply pressure the locking screw in the dynamic position to compress a fracture gap. The aiming guide 560 utilizes a push button release mechanism 567 that locks the soft tissue sheaths 580 in place. The release mechanism 567 allows insertion of the soft tissue sheath 580 but prevents it from backing out. This feature helps to maintain the position of the soft tissue sheaths 580 for accurate screw length measurements and facilitates drilling and screw insertion. The aiming guide 560 is designed with extended sheath guides 580 for improved aiming accuracy.

Figure 17F:
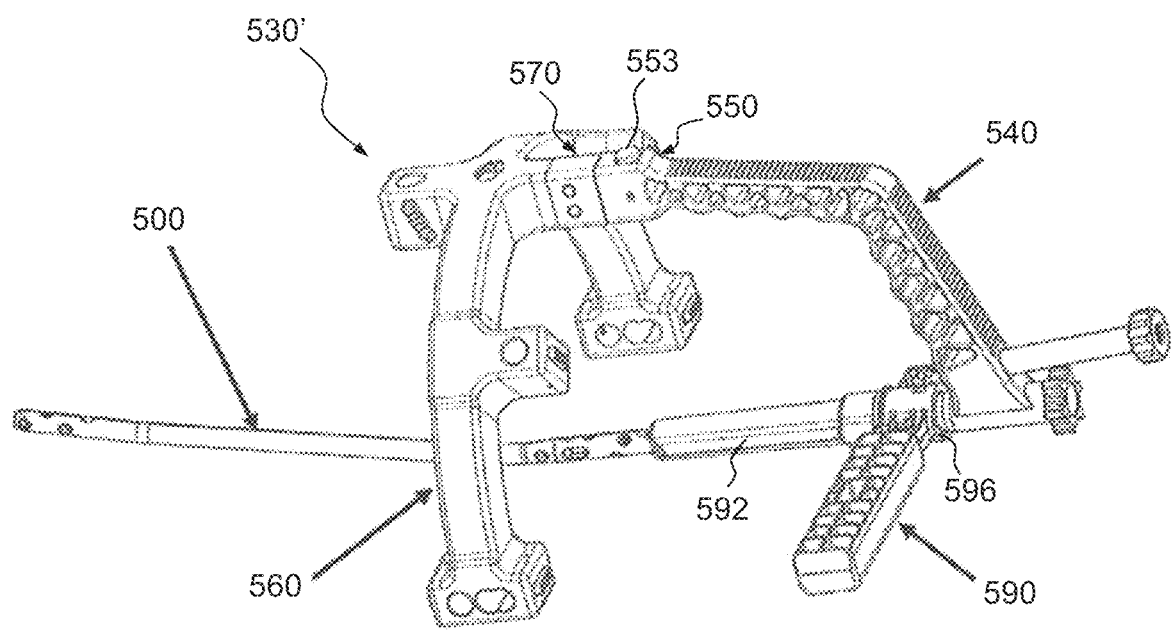

The supra-patellar approach uses a tibia entry point above the knee. A system 530' for use with the supra-patellar approach will be described with reference to FIGS. 17F-17L. The system 530' is substantially as in the previous embodiment but further includes a cannula assembly 590. As illustrated in FIG. 17F, at the time of insertion of the nail 500, the nail 500 and the connection portion 545 of the insertion tool 540 are inserted through the cannula assembly 590. The cannula assembly 590 protects the articular surface of the knee during the nail insertion process. As will be described below, the cannula assembly 590 also protects the articular surface of the knee during reaming. The reaming is performed through a drill guide 610 in the cannula 592 of the cannula assembly 590. Thereafter, the drill guide 610 is removed and nail 500 insertion is performed through the cannula 592 into the entry incision.

Figure 17G:
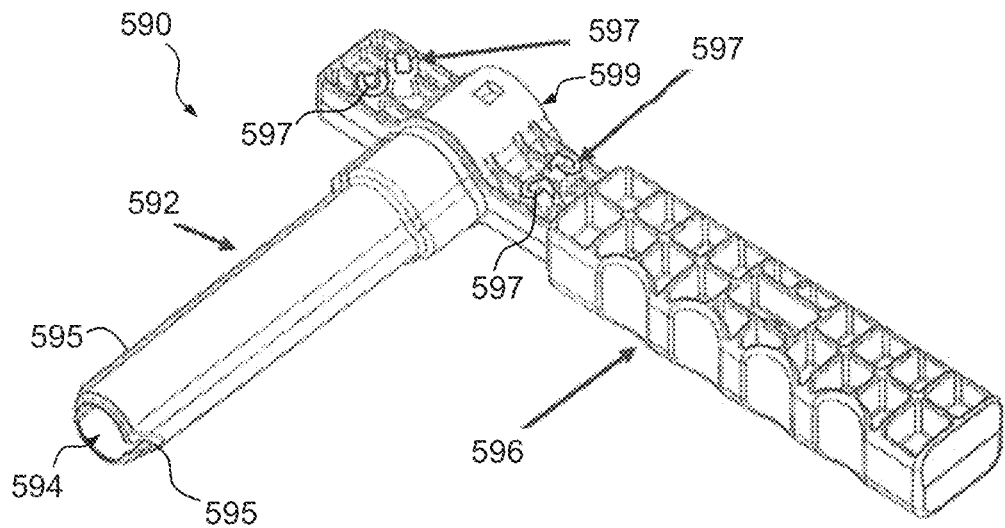
Figure 17H:
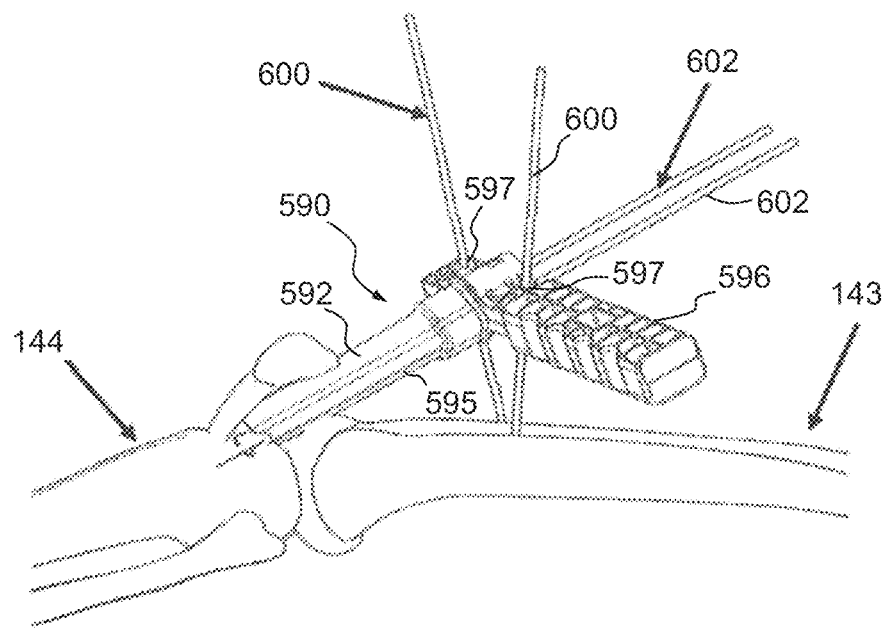

Referring to FIG. 17G, an illustrative cannula assembly 590 will be described. The cannula assembly 590 includes a flexible cannula 592 and a rigid handle 596. The cannula 592 has a through passage 594 which is aligned with an opening 599 in the handle 596 to define a continuous passage. In one embodiment, the flexible cannula 592 material is over-molded onto the rigid plastic handle 596. A pair of tibia guide slots 595 extend through the handle 596 and along the sides of the cannula 592. Transverse femur guide holes 597 extend through the handle 596. As shown in FIG. 17H, the guide slots 595 and guide holes 597 guide fixation pins 602 into the tibia 144 or femur 143.

Figure 17I:
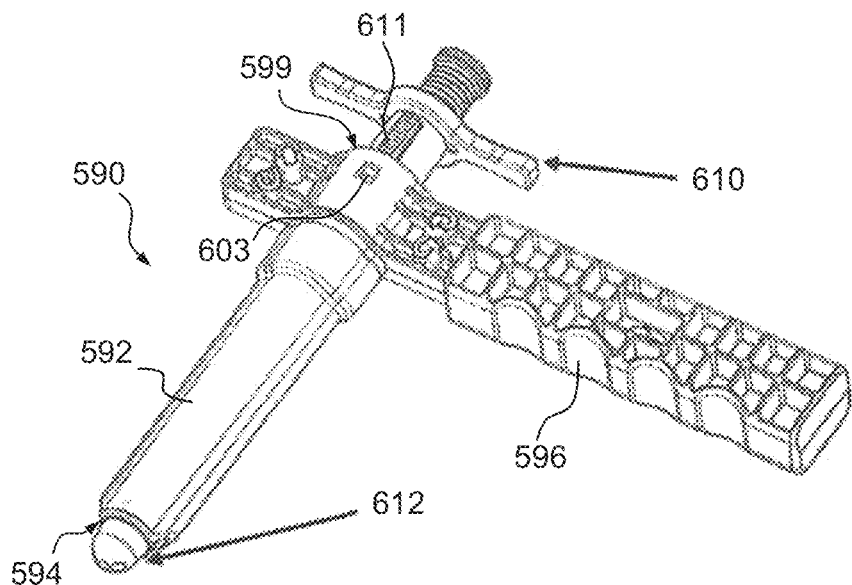

The cannula assembly 590 is inserted through an incision in the skin and is the working portal through which the surgeon can perform reaming, drilling, and nail insertion. The guide slots 595 and holes 597 allow the surgeon to fix the cannula 592 in place during the procedure. The guide slots 595 and holes 597 allow the cannula to be fixed to the femur 143 or tibia 144 with converging pins 602 depending on surgeon preference. The cannula 592 is reversible and can be used on either side of the patient. Referring to FIG. 17I, the cannula assembly 590 is designed to accept a metal drill sleeve 610 and round trocar 612. There is a connection point 603 on the cannula handle 596 that accepts the connector 611 on the metal drill sleeve 610. In the illustrated embodiment, the cannula 592 is tapered for easy removal of the drill sleeve 610. The soft, flexible cannula 592 is anatomically shaped to fit between the femoral condyles and minimize damage to the articular surface.

Figure 17J:
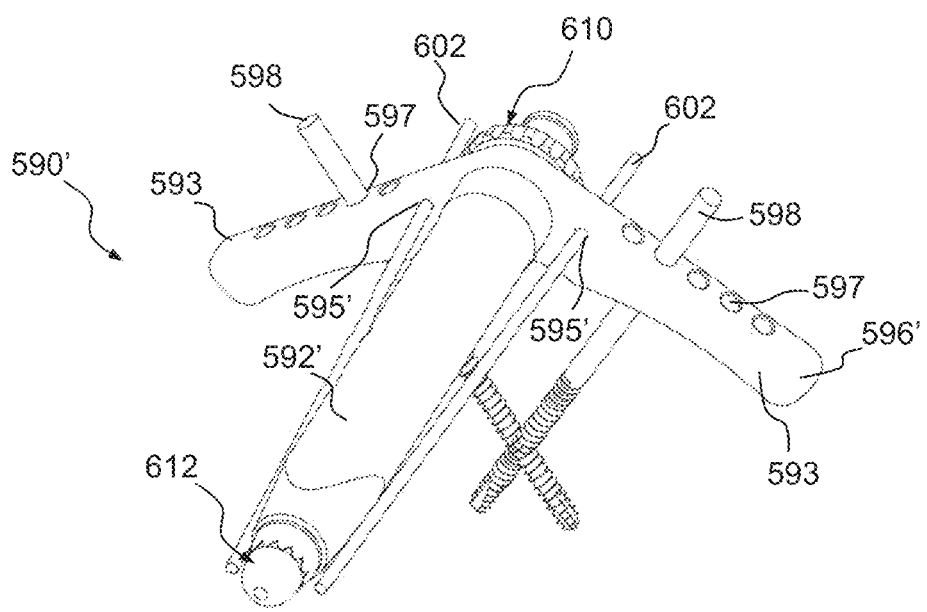
Figure 17K:
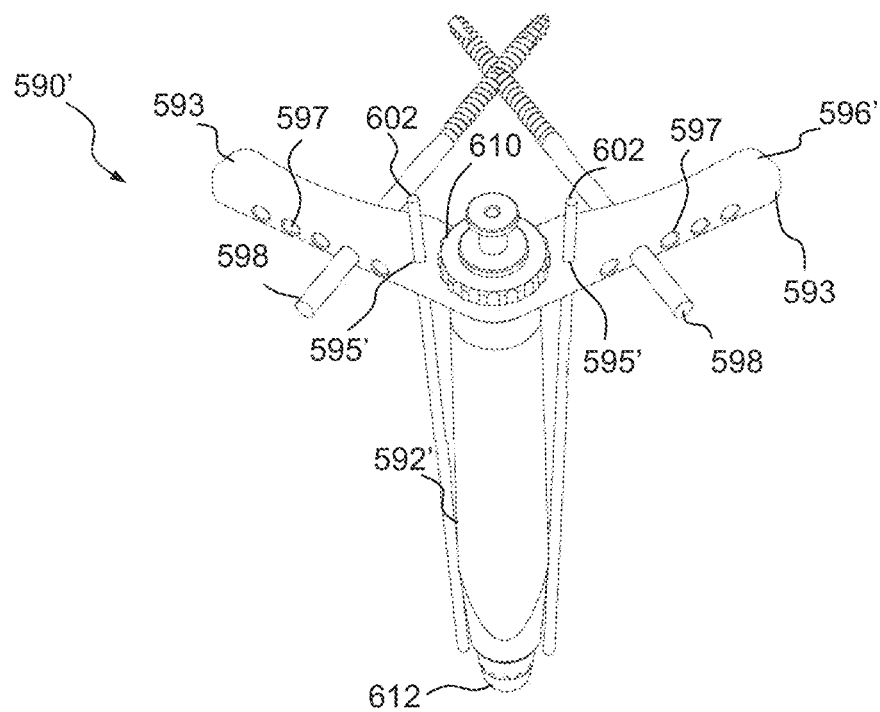
Figure 17L:
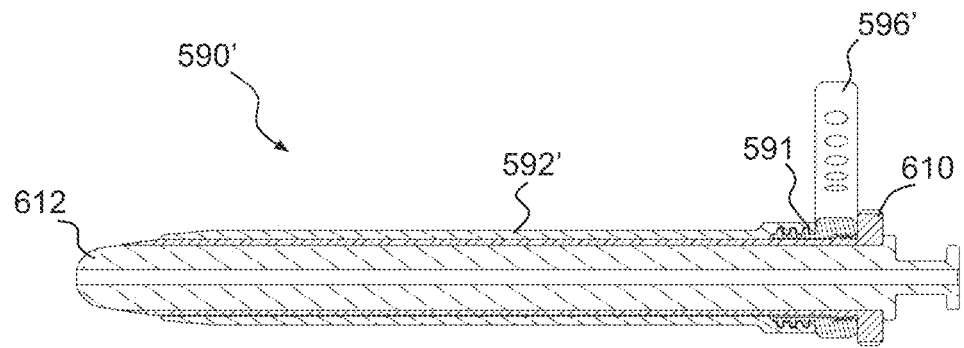

Referring to FIGS. 17J-L, a cannula assembly 590' in accordance with another illustrative embodiment will be described. The cannula assembly 590' is similar to the previous embodiment and includes a flexible cannula 592' extending from a rigid hub 596'. The rigid hub 596' includes legs 593 extending from each side of the cannula 592'. Each leg 593 of the hub 596' defines a respective tibia fixation hole 595' and a series of femur pin holes 597. The two tibia fixation holes 595' are designed to accept k wire or pin 602 for fixation to the tibia. The wires or pin 602 can be convergent or parallel. The femur pin holes 597 are for femur fixation using half pins 598. The cannula assembly 590' is designed to accept a metal drill sleeve 610 and round trocar 612.

Figure 18:
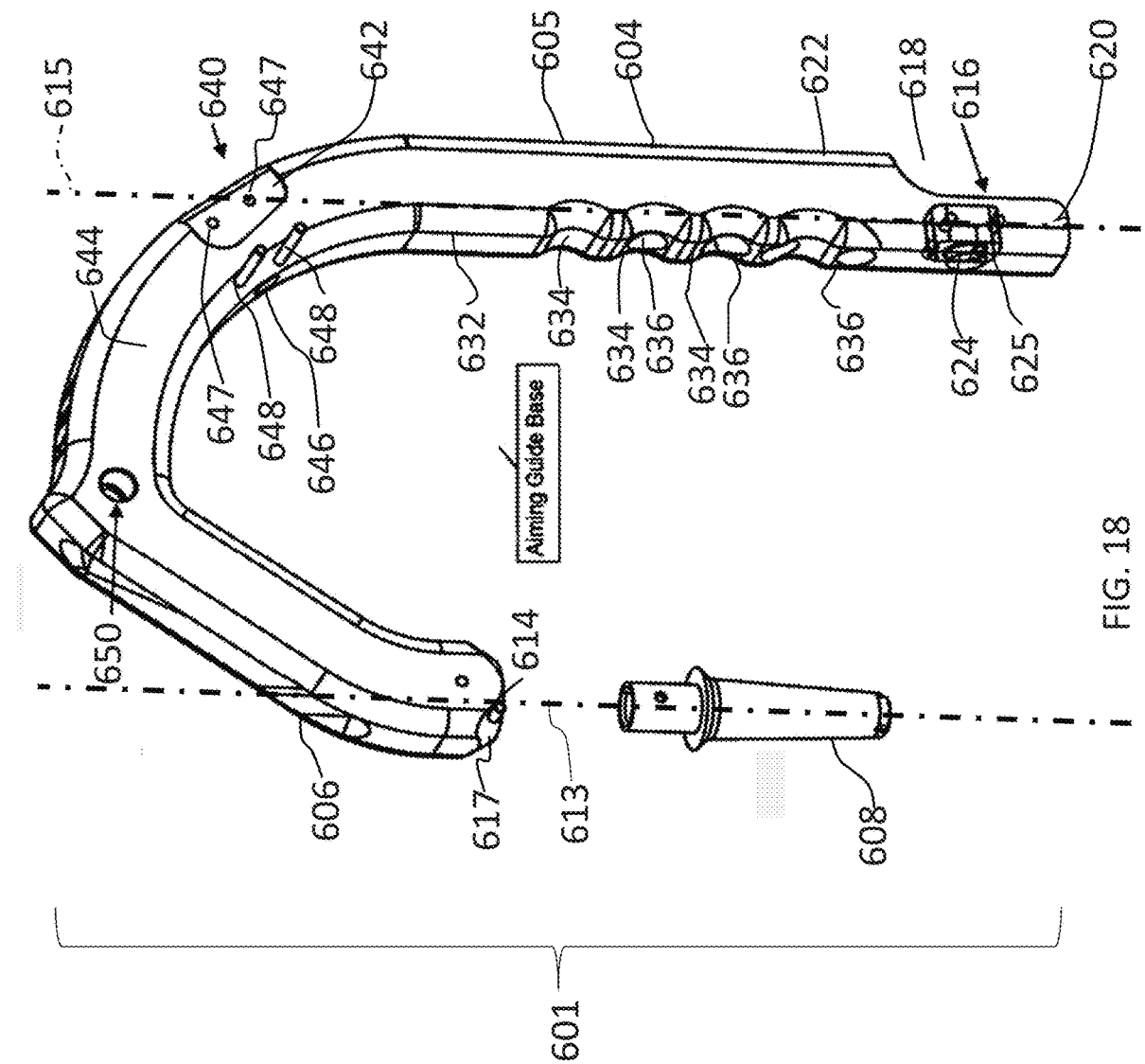
FIG. 18 is a perspective view of a femoral nail aiming guide according to an exemplary embodiment.

Referring to FIG. 18, an aiming guide 601 is provided for inserting an intramedullary nail into a bone, such as a femur 143 (shown in FIGS. 3A-3F). The aiming guide 601 provides the ability to insert femoral nails through both a piriformis and a greater trochanter entry point, allowing for antegrade and retrograde nail implementation. Additionally, the aiming guide 601 allows for the attachment of an impactor and multiple modules, which allows for simple operation of the aiming guide 601 while still allowing for a variety of engagement options for the clinician. Also, the aiming guide 601 provides a rigid connection to the nail to assist with insertion into the femur, and the base for an assembly that provides for a method to insert both recon fasteners or screws and oblique fasteners or screws to secure the femoral nail into the femur. Although described with reference to an antegrade/retrograde femoral nail, it will be appreciated that a similar aiming guide may be provided with other intramedullary systems.

The nail can be nail 309, shown in FIG. 9A, nail 500, shown in FIG. 17F, nail 699, shown in FIGS. 23-26, or other suitable intramedullary nail systems. The aiming guide 601 may be used to install recon fasteners or screws, oblique fasteners or screws and/or lateral/medial locking fasteners or screws into the intramedullary nail. The aiming guide 601 is configured to set the trajectory of the fasteners or screws to interface with corresponding through holes in either or both the proximal end and the distal end of the nail. A tissue sleeve may be used to protect soft tissue during the drilling process and to help set the drill trajectory.

The aiming guide 601 may include a generally arcuate or "J-shaped" body 605 having an elongate proximal handle portion 604 and a generally arcuate distal implant alignment tip connector portion 606. The distal implant tip connector portion 606 has a distal implant alignment tip 608 that may be configured to extend along a tip axis 613 substantially parallel to a longitudinal axis 615 of the proximal handle portion 604. The distal implant alignment tip 608 may be secured to the distal implant tip connector portion 606, for example, via spring loaded friction pads (not shown) located on the distal implant tip connector portion 606 that help keep the distal implant alignment tip 608 in place. The distal implant alignment tip 608 may also be secured, for example, in the manner provided in FIG. 11A.

According to one embodiment, the aiming guide 601 including the body 605 and implant alignment tip connector portion 606 may be a unitary construction that is constructed from a single material, such as, for example carbon fiber. The distal implant alignment tip 608 may optionally be constructed from a different material, such as, for example, a metal such as steel. The metal allows for an impactor (not shown) to be directly threaded into the distal implant alignment tip connector portion 606.

Further, the distal implant alignment tip 608 may be inserted into a receiver 614 at the distal end 617 of the distal implant alignment tip connector portion 606 for a releasable connection with the distal implant alignment tip connector portion 606. The distal implant alignment tip 608 is configured to releasably retain a femoral nail, such as nail 309, a nail 500, or a nail 699, as discussed above.

Figure 19:
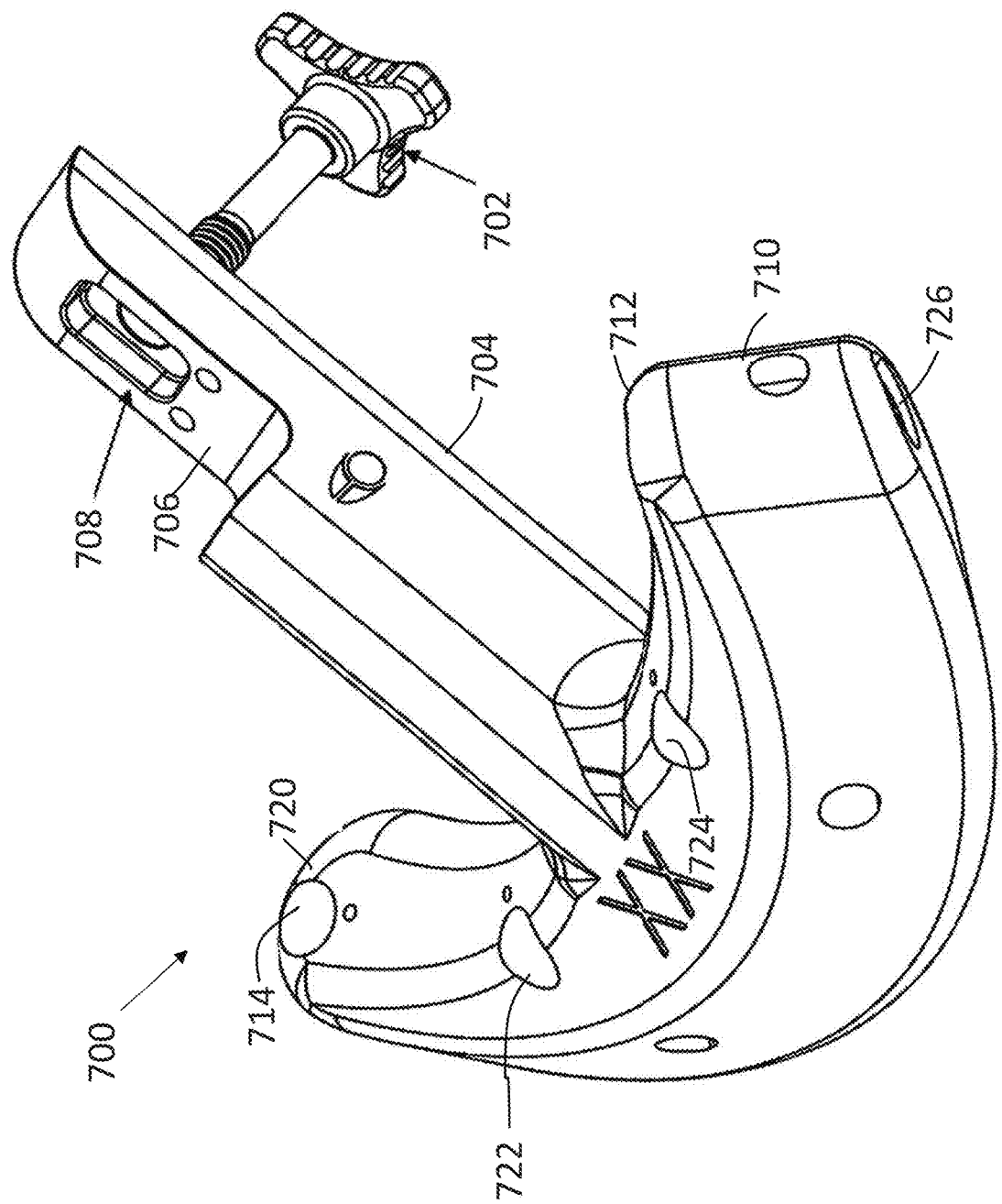
FIG. 19 is a perspective view of a recon module for releasable connection to the aiming guide of FIG. 18.

A proximal end 616 of the handle portion 604 may have a first attachment location 618 for releasably attaching a first module, such as, for example, a recon module 700, shown in FIG. 19. The first attachment location 618 includes a recessed portion 620 on an exterior side 622 of the handle portion 604. A threaded receiver 624 extends into the handle portion 604 from the recessed portion 620 and is sized to threadingly engage a thumb screw 702 on the recon module 700. A generally oblong alignment bushing 625 may surround the receiver 624.

The proximal handle portion 604 may include a hand grip 630 on an interior side 632 of the handle portion 604. The hand grip 630 includes a plurality of finger indents 634 to allow a clinician to grip the handle portion 604 and reduce the likelihood of the handle portion 604 rotating in the clinician's handle while using the aiming guide 601. The hand grip 630 has a plurality of through holes 636 extending therethrough from the exterior side 622 to the interior side 632. At least one of the through holes 636 extends along a hole axis that extends substantially perpendicular to the longitudinal axis 615 of the handle portion 604. In an exemplary embodiment, each of the through holes 636 extends along a hole axis that extends substantially perpendicular to the longitudinal axis 615 of the handle portion 604.

Figure 26:
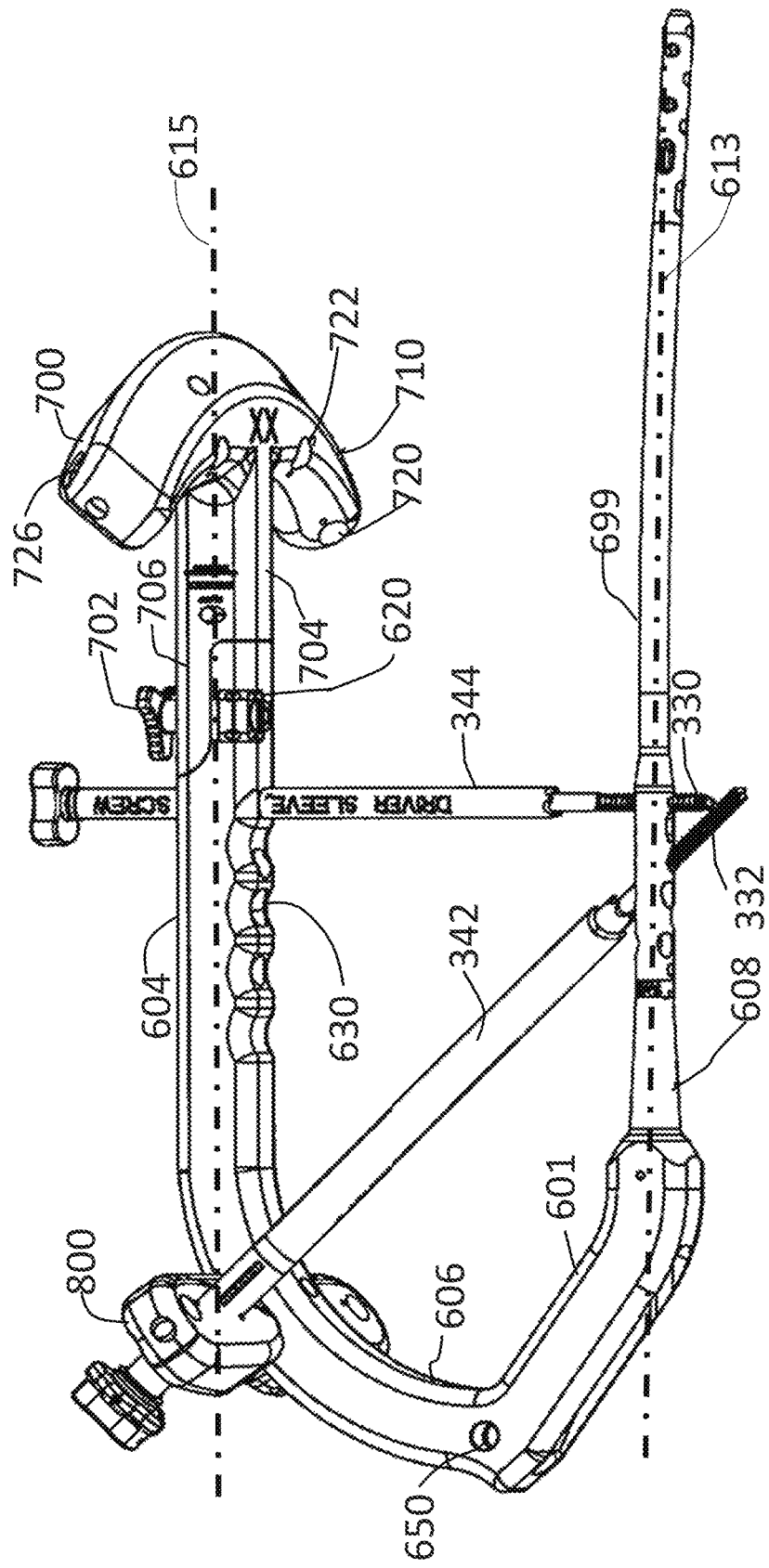
FIG. 26 is a perspective view of the aiming guide assembly of FIG. 21 with one screw inserted through the aiming guide and one screw inserted through the oblique module and into a femoral nail.

Through holes in the aiming guide and/or modules can be used to align sleeve 340, 342, 344 and screw 330, 332 with the femoral nail 699. As shown in FIG. 26, through hole 636 can align sleeve 344 and screw 330 with an opening in the femoral nail 699. The sleeve 344 can be similar to the sleeves or sheaths described herein (e.g., sheath 117) configured to protect soft tissue and allow for insertion of a drill, driver, fasteners or screws (e.g., fastener 119, fixation devices 330, 332), and the like configured to be aligned with and inserted through the openings in the intramedullary nail and into the bone.

Figure 20:
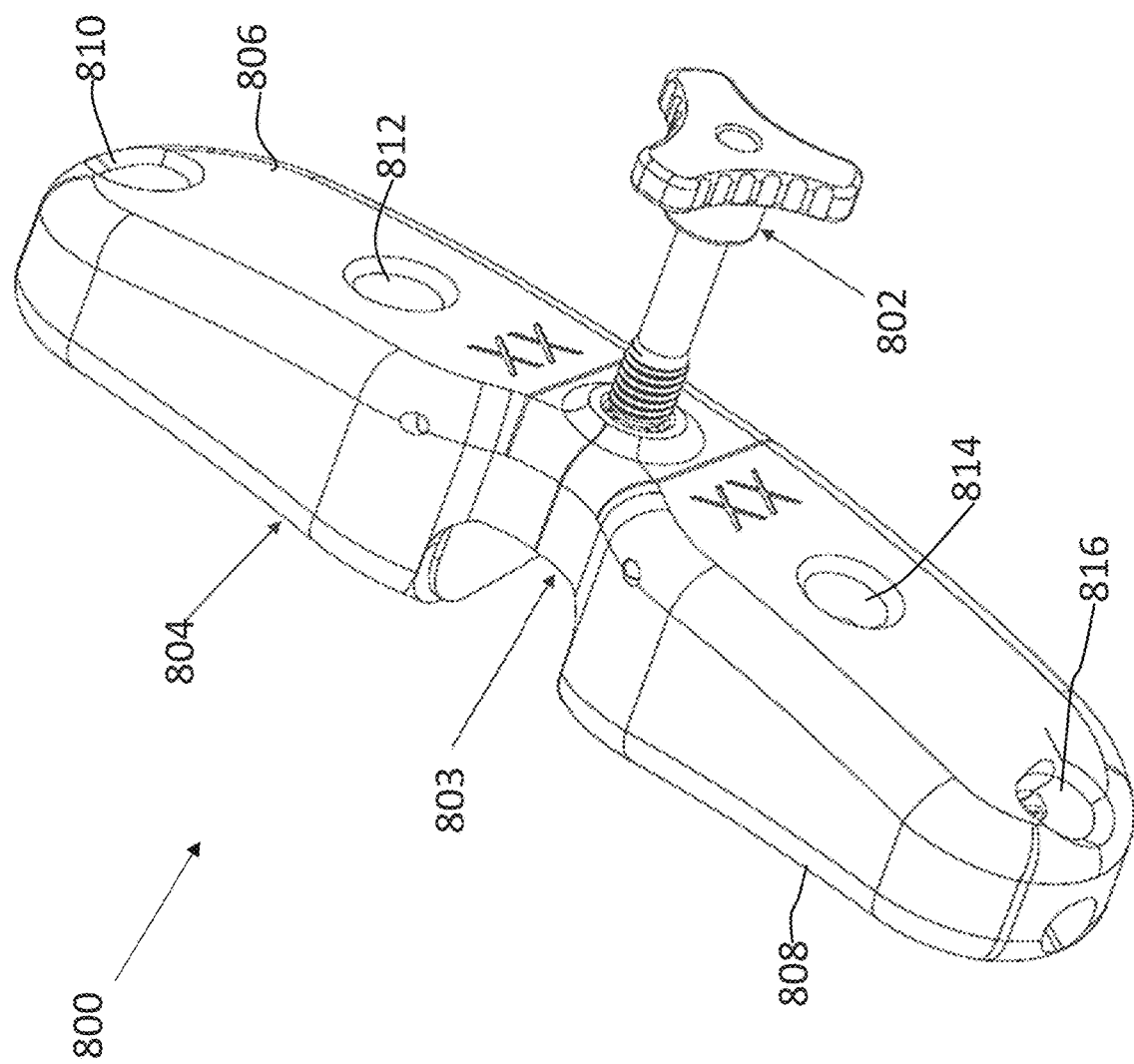
FIG. 20 is a perspective view of an oblique module for releasable connection to the aiming guide of FIG. 18.
Figure 21:
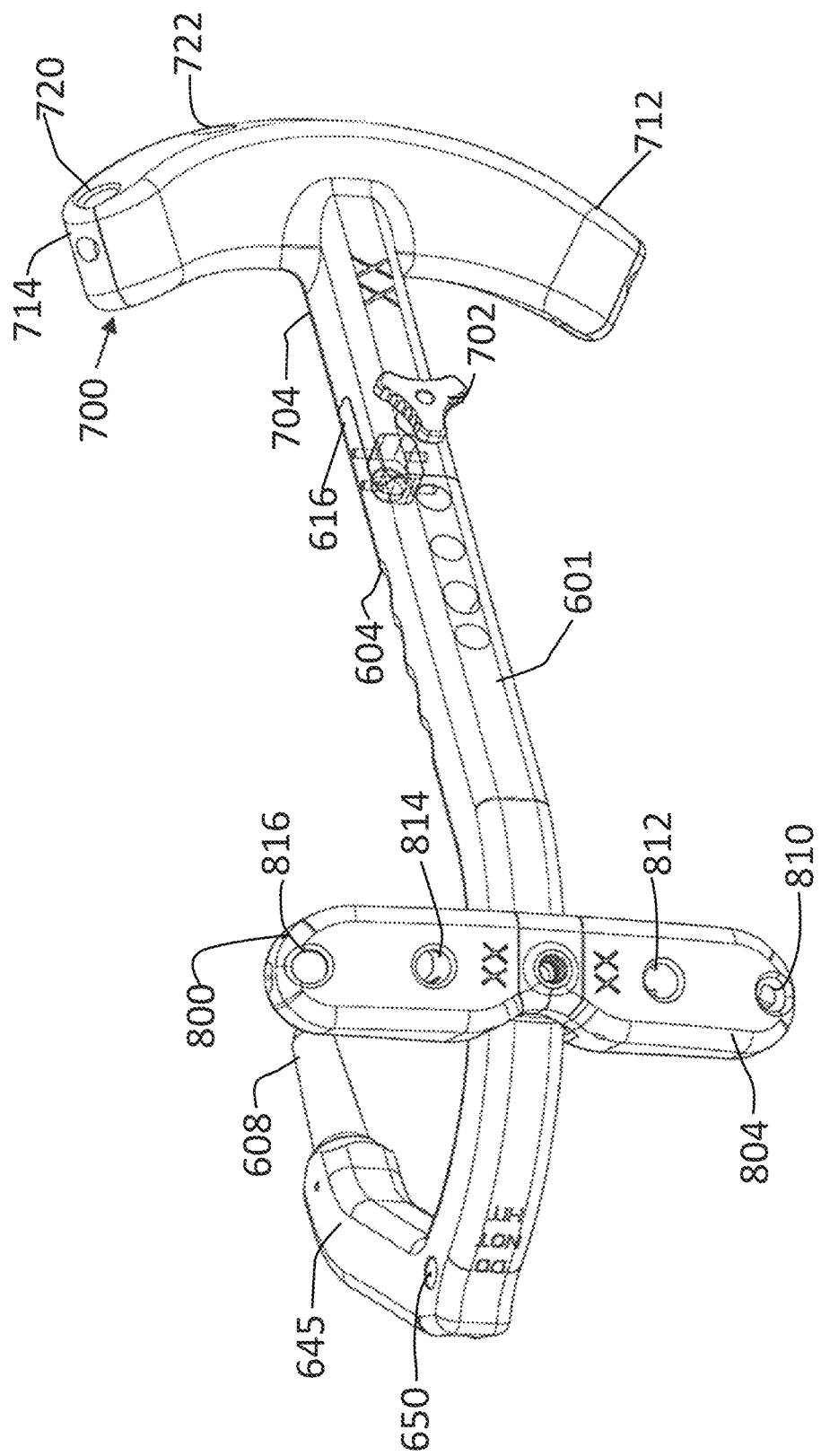
FIG. 21 is a perspective view of an aiming guide assembly including the recon module of FIG. 19 and the oblique module of FIG. 20, both connected to the aiming guide of FIG. 18.
Figure 22:
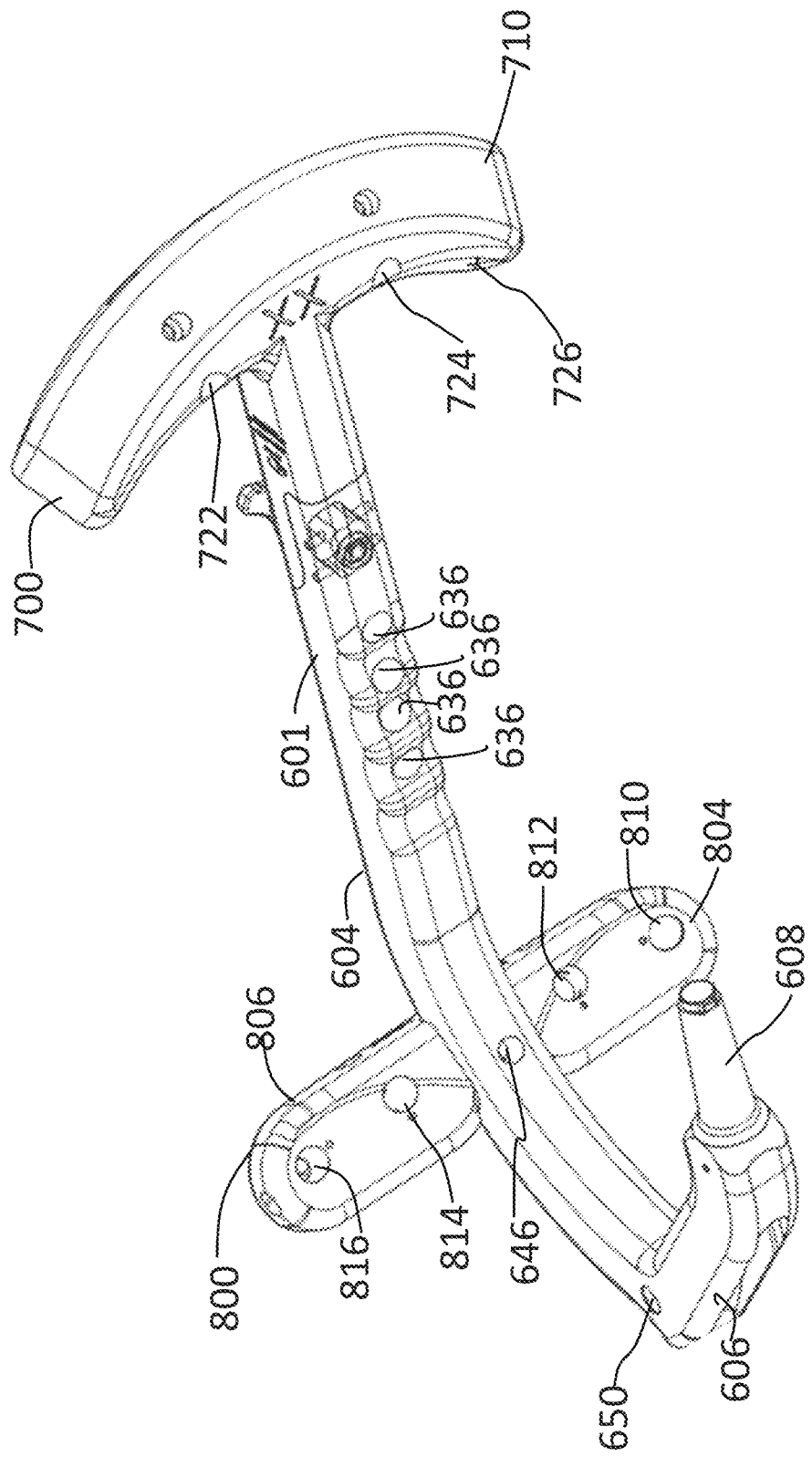
FIG. 22 is a reverse perspective view of the aiming guide assembly of FIG. 21.

Distal from the handle portion 604, the distal implant alignment tip portion 606 further includes a second attachment location 640 for releasably attaching a second module, such as, for example, an oblique module 800, shown in FIG. 20. The second attachment location 640 may include a metal alignment block 642 on each side wall 644, 645 (side wall 645 is shown in FIG. 21) of the distal implant alignment tip portion 606. The alignment blocks 642 may be used to align the oblique module 800 on the body 605. Pins 648 fit into holes 647 in the alignment blocks 642 (only one alignment block 642 is shown) to retain the alignment blocks to the body 605. A threaded receiver 646 extends through the distal implant alignment tip portion 606 between the alignment blocks 642 and is sized to threadingly engage a thumb screw 802 on the oblique module 800 (shown in FIG. 20). The distal implant alignment tip portion 606 further comprises a third attachment location 650 for releasably attaching an impactor attachment (not shown) to support the impactor discussed above. The third attachment location 650 can be a threaded opening to receive a threaded insert on the impactor attachment.

Referring to FIGS. 19 and 21, the recon module 700 may be releasably attached to the proximal end 616 of the proximal handle portion 604. The recon module 700 includes a connection piece 704 that engages the proximal end 616 of the proximal handle portion 604. The connection piece 704 includes a recessed portion 706 that mirrors the recessed portion 620 in the proximal end 616 for a secure engagement. Recessed portion 706 includes a generally oblong receiver 708 that is sized to accept the generally oblong alignment bushing 625 to prevent translation or rotation of the recon module 700 with respect to the aiming guide 601. With the generally oblong alignment bushing 625 inserted into the receiver 708, the thumb screw 702 is aligned with the threaded receiver 624 so that the recon module 700 can be releasably secured to the aiming guide 601 by threading the thumb screw 702 into the threaded receiver 624.

The recon module 700 may have an arcuate body 710 having a first recon portion 712 extending from the first side wall 644 of the proximal handle portion 604 and a second recon portion 714 extending from the second side wall 645 of the proximal handle portion 604, distal from the first side, when the recon module 700 is attached to the aiming guide 601, as shown in FIG. 21. The arcuate body 710 has a plurality of recon through holes 720, 722, 724, 726 extending therethrough, such that each of the plurality of recon through holes extends along an axis intersecting the tip axis 613.

Referring to FIGS. 20 and 21, the oblique module 800 may be releasably attached to the distal implant alignment tip portion 606. The oblique module 800 includes a generally U-shaped attachment site 803 that engages the alignment blocks 642 when the oblique module 800 is inserted onto the aiming guide 601 so that the thumb screw 802 is aligned with the threaded receiver 646. The oblique module 800 can be releasably secured to the aiming guide 601 by threading the thumb screw 802 into the threaded receiver 646.

The oblique module 800 may have an elongate body 804 having a first oblique portion 806 extending from a first side of the attachment site 803 and a second oblique portion 808 extending from a second side of the attachment site 803, distal from the first side, when the oblique module 800 is attached to the aiming guide 601, as shown in FIG. 21. The elongate body 804 has a plurality of oblique through holes 810, 812, 814, 816 extending therethrough, such that each of the plurality of oblique through holes 810, 812, 814, 816 extends along an axis intersecting the tip axis 613.

Figure 23:
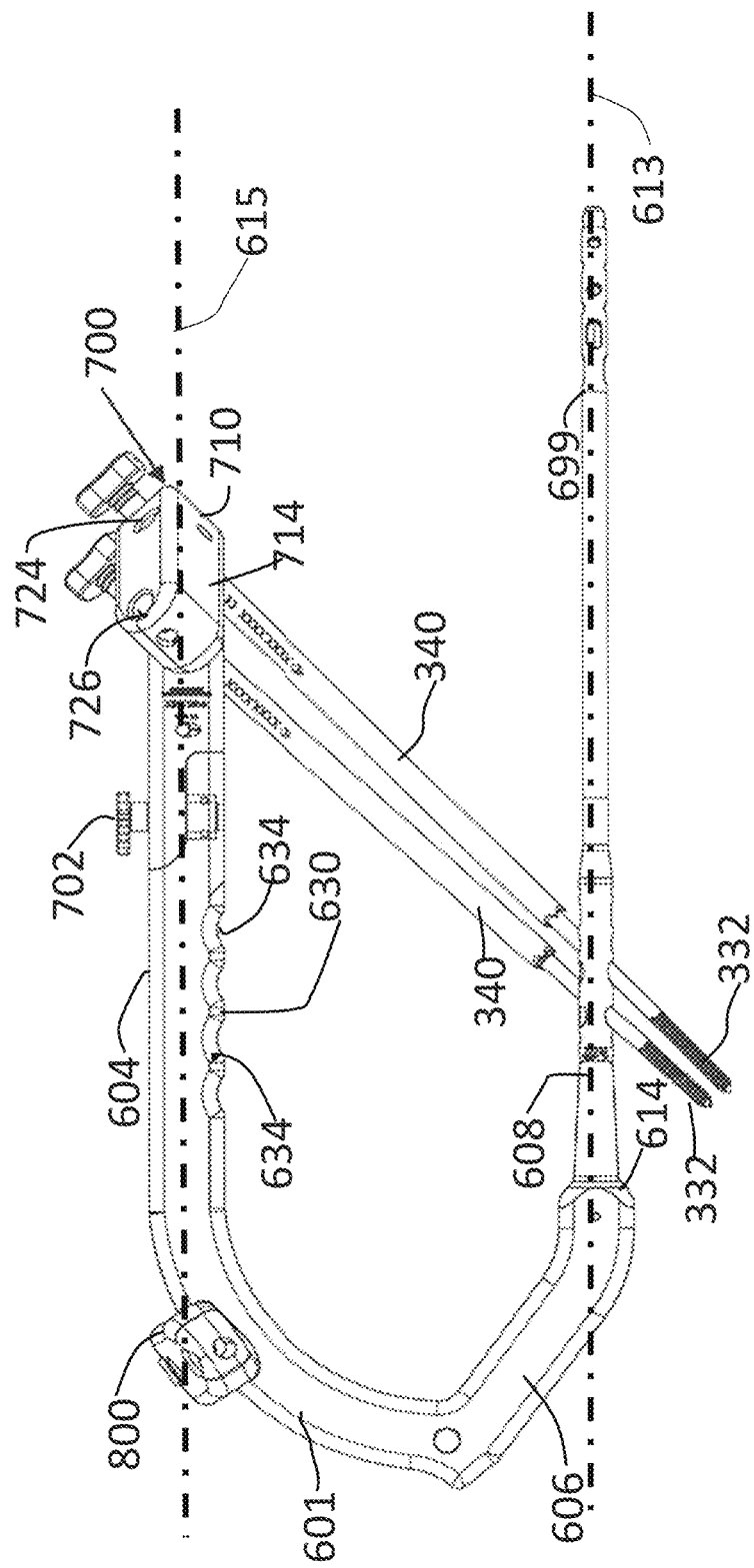
FIG. 23 is a perspective view of the aiming guide assembly of FIG. 21 with two screws inserted through the recon module and into a femoral nail.
Figure 24:
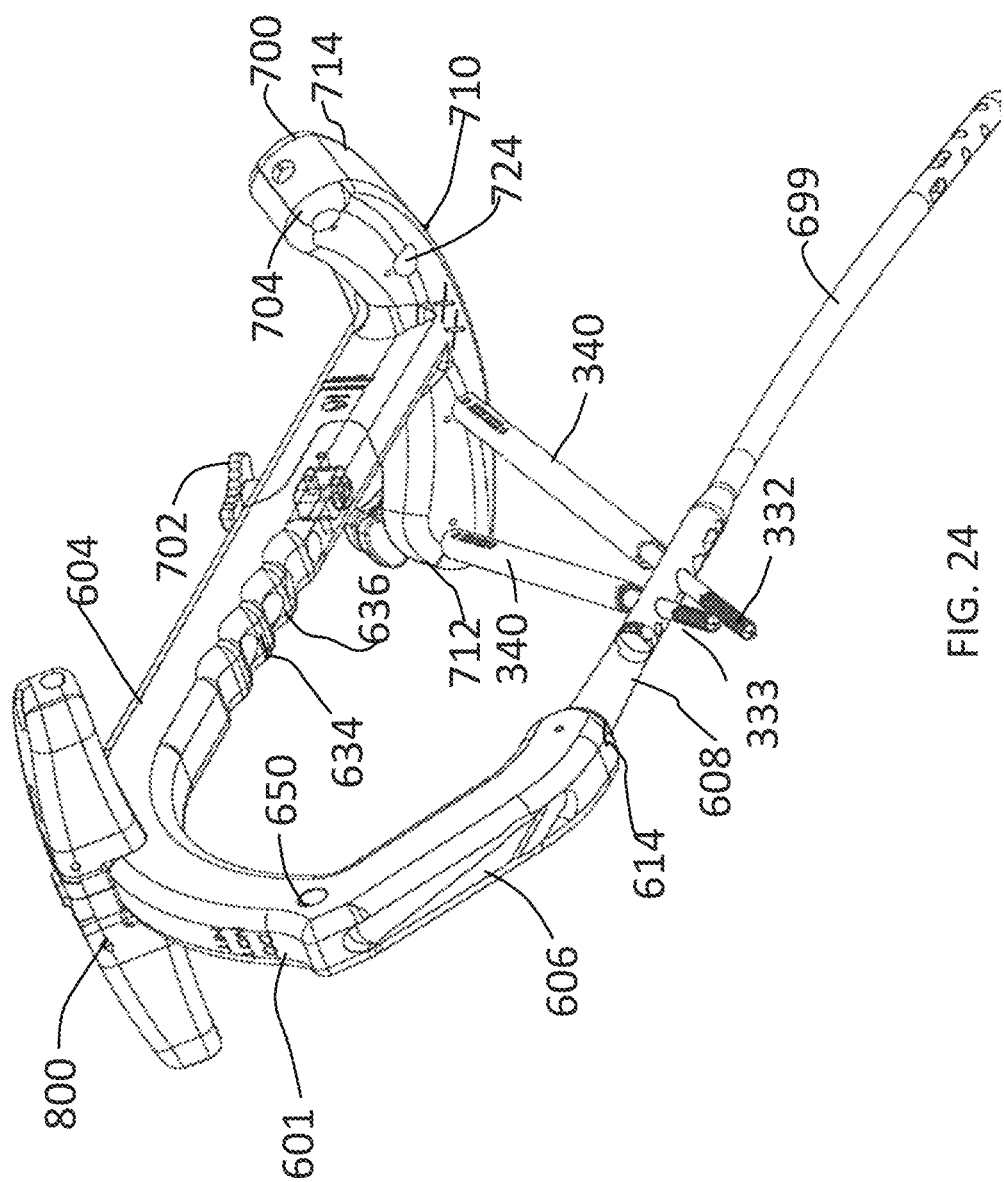
FIG. 24 is a reverse perspective view of the aiming guide assembly of FIG. 23 with two screws inserted through the recon module and into the femoral nail.
Figure 25:
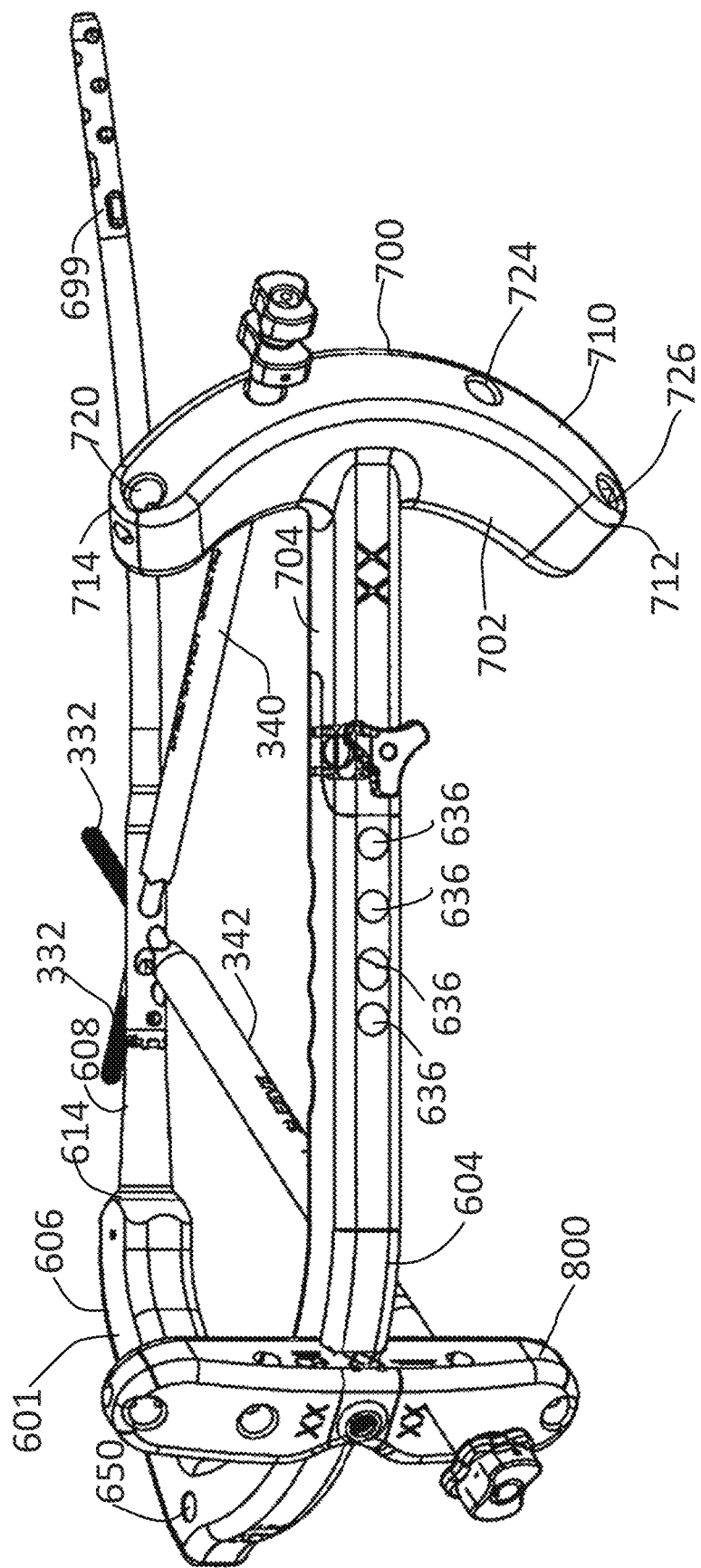
FIG. 25 is a perspective view of the aiming guide assembly of FIG. 21 with one screw inserted through the recon module and one screw inserted through the oblique module and into a femoral nail.

Aiming guide 601, recon module 700, and/or oblique module 800 may form an aiming guide assembly that supports a plurality of screws 330, 332 inserted therethrough and into femoral nail 699, as shown in FIGS. 23-26. In FIGS. 23 and 24, two recon screw sleeves 340 are shown extending through recon module 700 to align recon fasteners 332 with the intramedullary nail 699 for placement of the recon fasteners 332; in FIG. 25, a single recon screw sleeve 340 extends through recon module 700 for placement of the recon fastener or screw 332 in the femoral head, while a single oblique screw sleeve 342 extends through the oblique module 800 for placement of the oblique screw 332 through the nail 699 into the greater trochanter of the femur and preferably not the lesser trochanter of the femur; and in FIG. 26, a single oblique screw sleeve 342 extends through the oblique module 800, while a single driver screw sleeve 344 extends from the handle portion 604 of the aiming guide 601 for placement of screw 330 into the femoral nail 699. While these exemplary embodiments of screw sleeves 340, 342, 344 and screw configurations are shown, those skilled in the art will recognize that other sleeve and screw configurations can be provided with the aiming guide assembly.

While the recon module 700 and the oblique module 800 are shown with the aiming guide 601, those skilled in the art will recognize that the recon module 700 and the oblique module 800 can be used independently or omitted and just the aiming guide 601 alone can be used with the femoral nail 699 and one or more sleeves 340, 342, 344 through the aiming guide 601 for placing fasteners or screws 330, 332 into the femoral nail 699.

Figure 27:
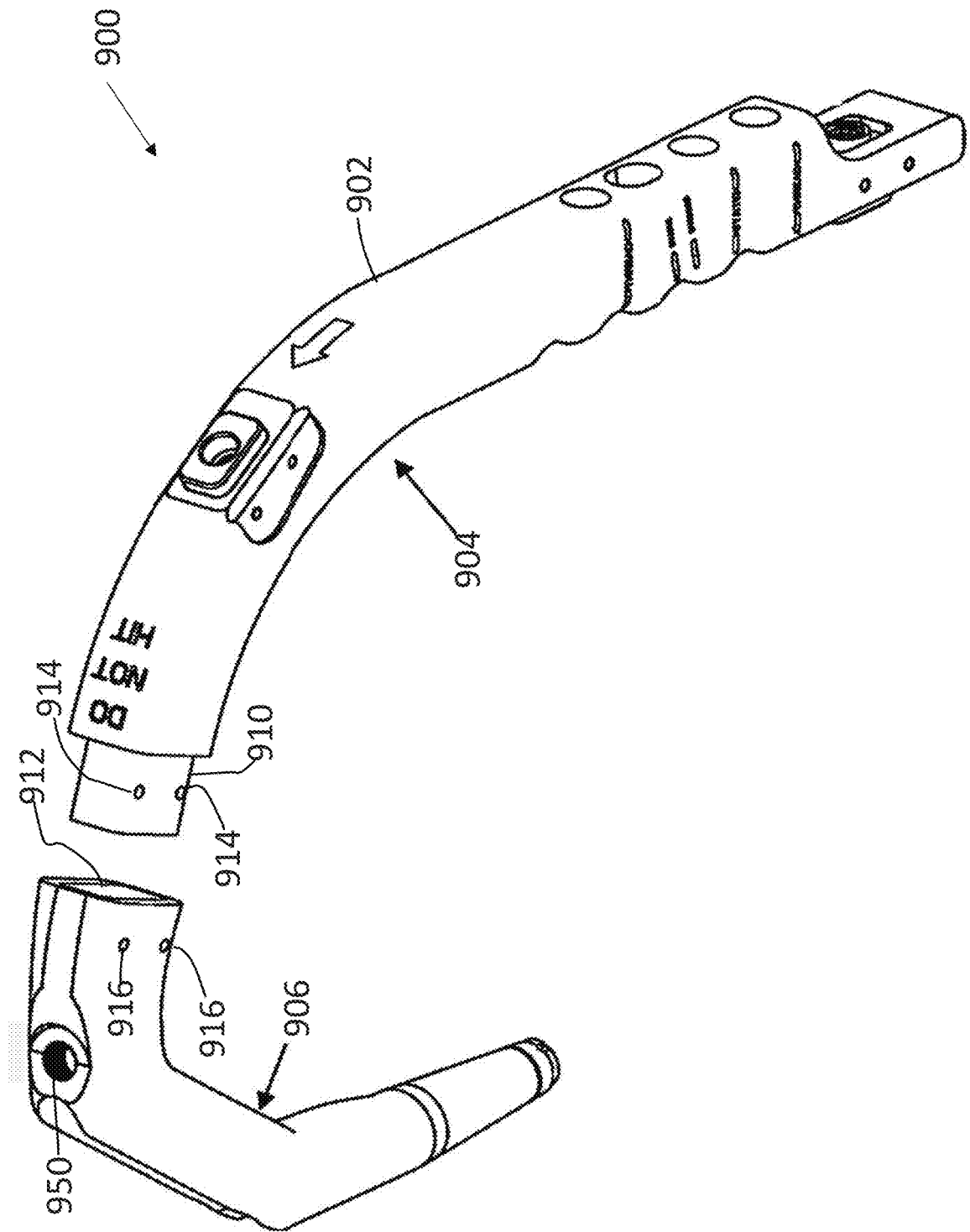
FIG. 27 is a perspective view of a femoral nail aiming guide according to another exemplary embodiment.

Referring now to FIG. 27, an alternative embodiment of an aiming guide 900 is similar to the aiming guide 601, but instead of being of unitary construction from a single material, the aiming guide 900 can be a multi-part construction body 902 with a handle portion 904 constructed from a first material, such as, for example carbon fiber, and an aiming arm portion 906 constructed from a second material, such as, for example a metal or plastic.

As shown in FIG. 27, the handle portion 904 has a generally rectangular male insert 910 that is sized and shaped to fit into a generally rectangular female receiver 912 in the aiming arm portion 906. The insert 910 has a plurality of locking holes 914 that align with a like plurality of locking holes 916 in the aiming arm portion 906 such that, when the insert 910 is inserted into the receiver 912, the locking holes 914, 916 align with each other to allow pins (not shown) to be inserted therein to secure the aiming arm portion 906 to the handle portion 904.

The aiming arm portion 906 also includes an attachment location in the form of a threaded opening 950 for directly connecting the impactor discussed above to the aiming arm portion 906.

Operation of the aiming guide 900 is similar to the operation of the aiming guide 601 as discussed above. The recon module 700 and the oblique module 800 can each be releasably secured to the aiming guide 900 to assist in aiming screw sleeves 330, 331, and 340, and corresponding screws, for example, into the nail 699.

Figure 28:
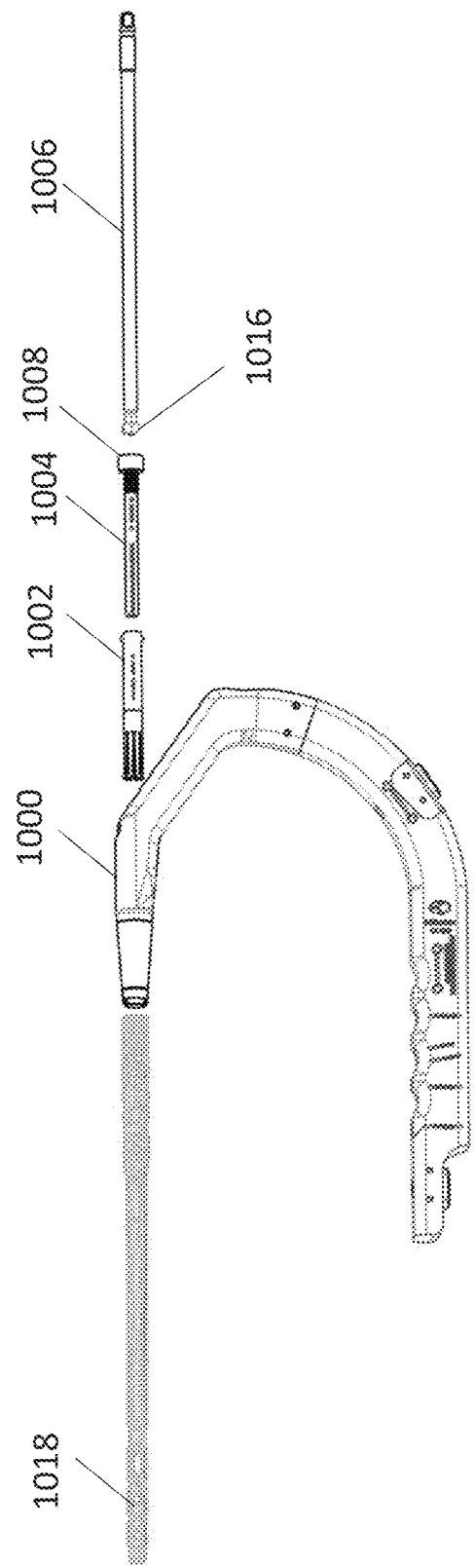
FIG. 28 is a perspective view of an exemplary aiming guide and bolt driver consistent with the principles of the present disclosure.

Referring now to FIG. 28, an exemplary aiming guide 1000 consistent with the principles of this disclosure is illustrated. Aiming guide 1000 may be similar to the aiming guides previously described. Also illustrated are collet 1002 and connection bolt 1004, which may also be similar to components previously described. In order to connect connection bolt 1004 to collet 1002 (and nail 1018 as previously described), a connection bolt driver 1006 may be used. Connection bolt 1004 may be inserted or removed from aiming guide 1000 through the use of connection bolt driver 1006. Connection bolt 1004 may be configured to be self-retaining. For example, according to an exemplary embodiment, connection bolt 1004 may be retained by bolt driver 1006 through an interference fit that allows bolt driver 1006 to be retained inside a head 1008 of connection bolt 1004.

Figures 29A, 29B:
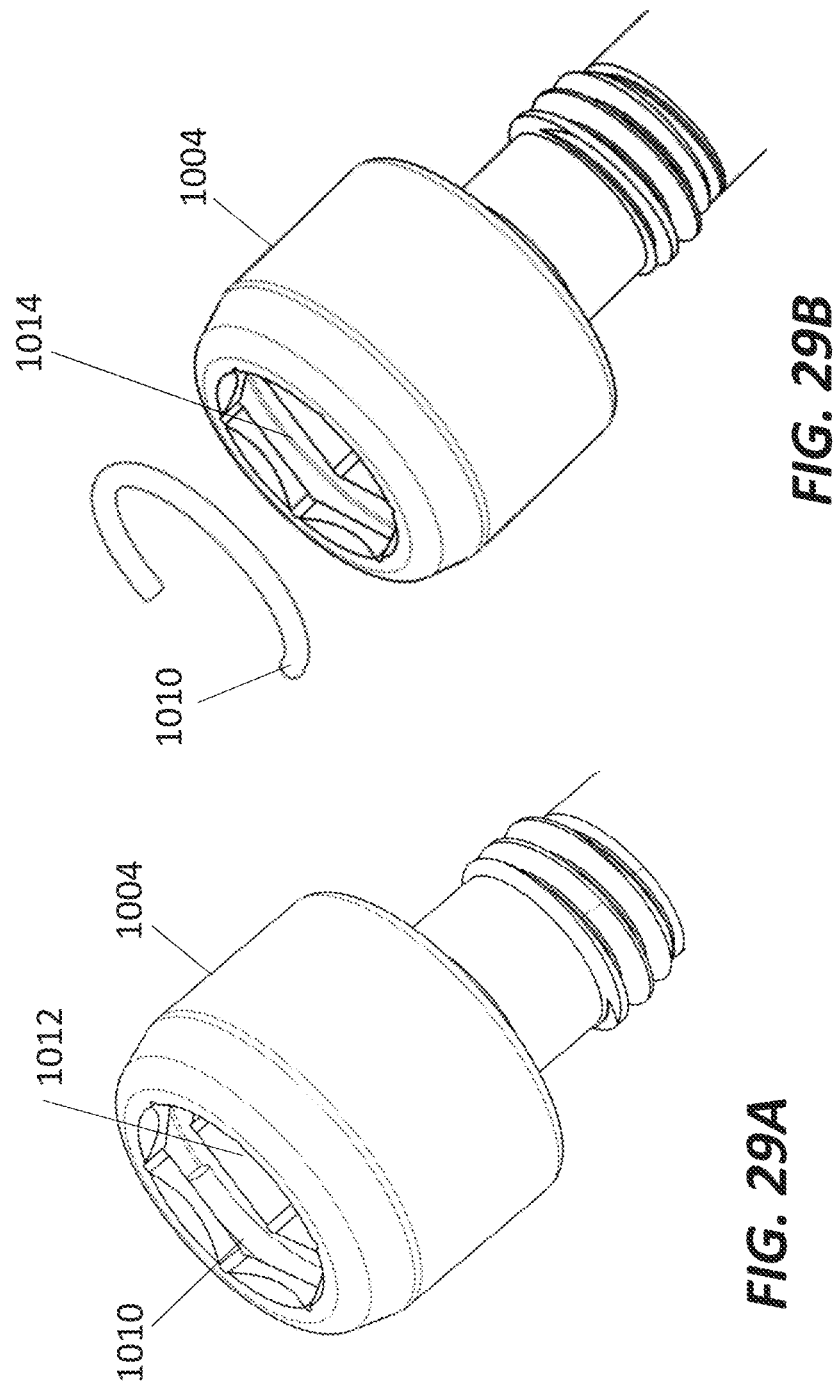
FIGS. 29A and 29B is a perspective view of an exemplary connection bolt consistent with the principles of the present disclosure.
Figure 30:
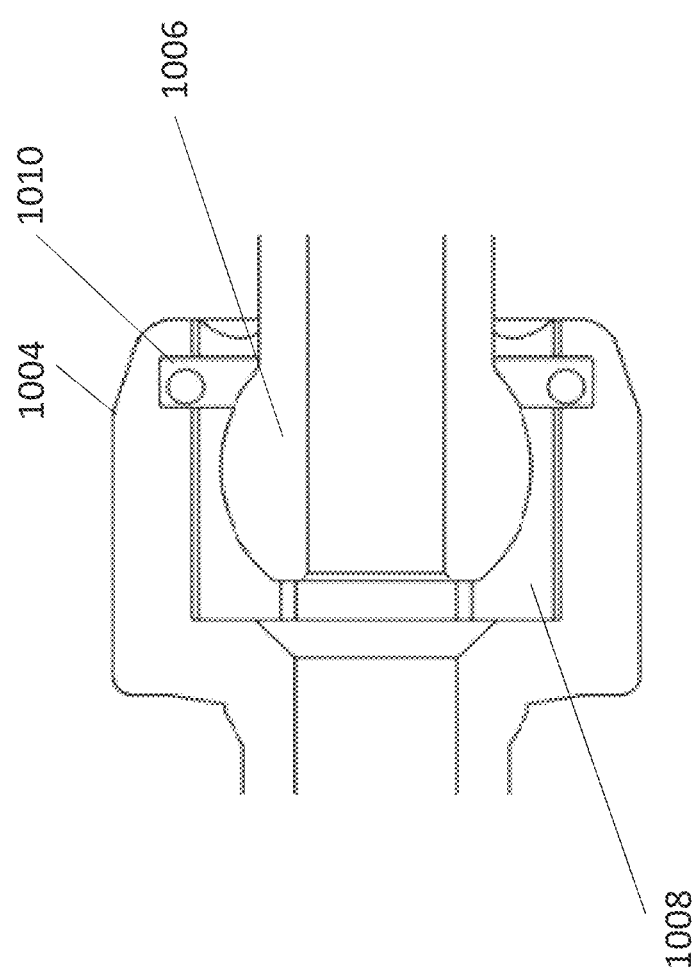
FIG. 30 is a perspective view of an exemplary connection bolt and connection bolt driver consistent with the principles of the present disclosure.

FIGS. 29A-29B illustrate an example of connection bolt 1004 that provides a self-retaining connection to bolt driver 1006. Connection bolt 1004 may include a circlip 1010 disposed inside of head 1008, which may include a hex recess 1012 configured to receive a portion of driver 1006. Connection bolt 1004 may be configured to include a radial groove 1014 into which circlip 1010 may be loaded. Circlip 1010 may then act as a spring to provide interference which retains bolt driver 1006 inside head 1008 of connection bolt 1004. Bolt driver 1006 may include a hex shaped end 1016 that inserts into hex shaped recess 1012. As bolt driver 1006 is inserted into head 1008, end 1016 may splay open circlip 1010 to seat it in groove 1014. Circlip 1010 may have a spring tension that holds bolt driver 1006 inside of head 1008 which is illustrated in FIG. 30.

As described above, the circlip feature allows for self-retention of the connecting bolt to the bolt driver. This provides easy insertion and removal of the bolt and minimizes risks of the connection bolt unintentionally falling to the ground or into soft tissue of a patient. This may also provide a user with options for an angled approach to the head of the connection bolt, which may allow easier passage around certain soft tissue structures.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and

What is claimed is:

1. A system for inserting an intramedullary nail into a bone, the system comprising:
an intramedullary nail; and
a J-shaped aiming guide comprising an elongate proximal handle portion and a distal implant alignment tip extending parallel to a longitudinal axis of the proximal handle portion, wherein the aiming guide includes:
a collet configured to engage the intramedullary nail, the collet including internal threads;
a connection bolt configured to engage the internal threads of the collet to connect the collet with the intramedullary nail; and
a connection bolt driver configured to engage the connection bolt,
wherein the connection bolt comprises a head containing a circlip, the circlip configured to splay open upon insertion of the connection bolt driver into the head and provide tension around the connection bolt driver to retain the connection bolt driver in the head of the connection bolt.

2. The system according to claim 1, wherein the collet is configured to expand to engage an opening of the intramedullary nail.

3. The system according to claim 2, wherein the collet includes a hollow body with a through passage from a proximal end to a distal end of the collet.

4. The system according to claim 3, wherein the distal end of the collet has a radially outwardly extending collar.

5. The system accordingly to claim 4, wherein the collar is configured to be received in the opening of the intramedullary nail.

6. The system accordingly to claim 5, wherein the distal end of the body contains axial slots.

7. The system accordingly to claim 6, wherein the distal end of the collet contains internal threads.

8. The system of claim 7, wherein the connection bolt engages the internal threads to expand the collet within the opening of the intramedullary nail.

9. The system of claim 1, wherein the circlip is disposed in a radial groove of the head of the connection bolt.

10. The system of claim 1, wherein the head contains a hex-shaped recess that engages the connection bolt driver.

11. A method for inserting an implant into a bone, the method comprising:
coupling an implant to a J-shaped aiming guide comprising an elongate proximal handle portion and a distal implant alignment tip extending parallel to a longitudinal axis of the proximal handle portion;
disposing the implant into a medullary canal of a patient via the aiming guide;
inserting a fixation device into the implant via the aiming guide, wherein the aiming guide further includes:
a collet configured to engage the implant;
a connection bolt configured to engage the collet to connect the collet with the implant; and a connection bolt driver configured to engage the connection bolt,
wherein the connection bolt comprises a head containing a circlip, the circlip configured to splay open upon insertion of the connection bolt driver into the head and provide tension around the connection bolt driver to retain the connection bolt driver in the head of the connection bolt.

12. The method according to claim 11, wherein the collet is configured to expand to engage an opening of the implant.

13. The method according to claim 12, wherein the collet includes a hollow body with a through passage from a proximal end to a distal end of the collet.

14. The method according to claim 13, wherein the distal end of the collet has a radially outwardly extending collar.

15. The method accordingly to claim 14, wherein the collar is configured to be received in the opening of the implant.

16. The method accordingly to claim 15, wherein the distal end of the body contains axial slots.

17. The method accordingly to claim 16, wherein the distal end of the collet contains internal threads.

18. The method of claim 17, wherein the connection bolt engages the internal threads to expand the collet within the opening of the implant.

19. The method of claim 11, wherein the circlip is disposed in a radial groove of the head of the connection bolt.

20. The method of claim 11, wherein the head contains a hex-shaped recess that engages the connection bolt driver.

* * * * *